(12) United States Patent
Maier et al.

(10) Patent No.: US 8,399,505 B2
(45) Date of Patent: Mar. 19, 2013

(54) SULFONYLPYRROLES

(75) Inventors: Thomas Maier, Constance (DE);
Thomas Beckers, Constance (DE);
Thomas Baer, Reichenau (DE); Petra Gimmnich, Constance (DE); Frank Dullweber, Constance (DE); Matthias Vennemann, Constance (DE)

(73) Assignee: 4SC AG, Planegg Martinsrid (DE)

( * ) Notice: Subject to any disclaimer, the term of this patent is extended or adjusted under 35 U.S.C. 154(b) by 53 days.

(21) Appl. No.: 12/822,606

(22) Filed: Jun. 24, 2010

(65) Prior Publication Data
US 2010/0261761 A1    Oct. 14, 2010

Related U.S. Application Data

(62) Division of application No. 10/591,477, filed on Sep. 27, 2006, now Pat. No. 7,842,820.

(30) Foreign Application Priority Data

Mar. 11, 2004 (EP) ..................... 04101003

(51) Int. Cl.
*A61K 31/40* (2006.01)
*C07D 207/34* (2006.01)
(52) U.S. Cl. ....................... 514/424; 548/542
(58) Field of Classification Search ............. 514/424; 548/542
See application file for complete search history.

(56) References Cited

U.S. PATENT DOCUMENTS

| 4,960,787 | A | 10/1990 | Wasley |
| 5,534,654 | A | 7/1996 | Ohtani et al. |
| 6,432,999 | B2 | 8/2002 | Talley et al. |
| 2002/0026052 | A1 | 2/2002 | Boschelli et al. |
| 2005/0234033 | A1 | 10/2005 | Anandan et al. |
| 2005/0288282 | A1 | 12/2005 | Delorme et al. |
| 2006/0258728 | A1 | 11/2006 | Tani et al. |
| 2007/0184979 | A1 | 8/2007 | Maier et al. |
| 2008/0176848 | A1 | 7/2008 | Maier et al. |
| 2009/0117074 | A1 | 5/2009 | Maier et al. |

FOREIGN PATENT DOCUMENTS

| EP | 0570594 | 11/1993 |
| EP | 1431267 | 6/2004 |
| WO | WO9312075 | 6/1993 |
| WO | WO0138322 | 5/2001 |
| WO | WO0138323 | 5/2001 |
| WO | WO03016254 | 2/2003 |
| WO | WO03024448 | 3/2003 |
| WO | WO2004037751 | 5/2004 |
| WO | WO2004046094 | 6/2004 |
| WO | WO2005020921 | 3/2005 |
| WO | WO2005070900 | 8/2005 |
| WO | WO2005086898 | 9/2005 |
| WO | WO2005087724 | 9/2005 |
| WO | WO2006066189 | 6/2006 |
| WO | WO2006060712 | 7/2006 |
| WO | WO2006003171 | 8/2006 |
| WO | WO2006097474 | 9/2006 |
| WO | WO2006105979 | 10/2006 |
| WO | WO2006066197 | 12/2006 |
| WO | WO2007039404 | 4/2007 |

OTHER PUBLICATIONS

Kubinyi (3D QSAR in Drug Design: Ligand-Protein Interactions and Molecular Similarity, vol. 2-3, Springer, 1998, 800 pages), TOC & pp. 243-244 provided.*
Danesi (Trends in Pharm. Sci, (2001) v. 22, n. 8, p. 420-426).*
Angle, Steven, R. and Martin L. Neitzel, "A Simple Method for the Synthesis of Substituted Benzylic Ketones: Homologation of Aldehydes via the Situ Generation of Aryldiazomethanes from Aromatic Aldehydes" (Journal of Organic Chemistry), 2000, 6458-6461, 65.
Engman, Lars and Vijay Gupta, "Tetrahydrofuran Derivatives from Epoxides via Group Transfer Cyclization or Reductive Radical Cyclization of Organotellurium and Organoselenium Intermediates", *Journal of Organic Chemistry*, 1997, 157-173,62.
Kelly, William K., et al., "Phase I Study of an Oral Histone Deacetylase Inhibitor, Suberoylanilide Hydroxamic Acid, in Patients with Advances Cancer", *Journal of Clinical Oncology*, Jun. 10, 2005, 3923-3931, 23:17.
Tyrrell, Elizabeth and Phillip Brookes, "The Synthesis and Applications of Heterocyclic Boronic Acids", *Synthesis*, 469-483, 4. (2004).
U.S. Appl. No. 11/992,015, "Novel Sulphonylpyrroles as Inhibitors of Hdac S Novel Sulphonylpyrroles" filed Mar. 14, 2008.
U.S. Appl. No. 11/992,018, "Sulphonylpyrrole Hydrochloride Salts as Histone Deacetylases Inhibitors" filed Sep. 8, 2006.
Kubinyi (3D QSAR in Drug Design: Ligand-Protein Interactions and Molecular Similarity, vol. 2-3, *Springer*, 1998, 800 pages).
J. Almenara et al. "Synergistic Induction of Mitochondrial Damage and Apoptosis in Human Leukemia Cells by Flavopiridol and the Histone Deacetylase Inhibitor Suberoylanilide Hydroxamic Acid (SAHA)" *Leukemia*, vol. 16, pp. 1331-1343, 2002.
G. Bouchain et al. "Development of Potential Antitumor Agents. Synthesis and Biological Evaluation of a New Set of Sulfonamide Derivatives as Histone Deacetylase Inhibitors", *J. Med. Chem.*, vol. 46, pp. 820-830, 2003.
Y.L. Chung et al. "A Theraputic Strategy Uses Histone Deacetylase Inhibitors to Modulate the Expression of Genes Involved in the Pathogenesis of Rheumatoid Arthritis", *Molecular Therapy*, vol. 8, pp. 707-717, 2003.
P. Dhordain et al. "The LAZ3 (BCL-6) Oncoprotein Recruits a SMRT/mSIN3A/histone Deacetylase Containing Complex to Mediate Transcriptional Repression", *Nucleic Acids Research*, vol. 26, No. 20, pp. 4645-4651, 1998.

(Continued)

*Primary Examiner* — Robert Havlin
(74) *Attorney, Agent, or Firm* — Millen, White, Zelano & Branigan, P.C.

(57) ABSTRACT

Compounds of a certain formula (I), in which R1, R2, R3, R4, R5, R6 and R7 have the meanings indicated in the description, are novel effective HDAC inhibitors.

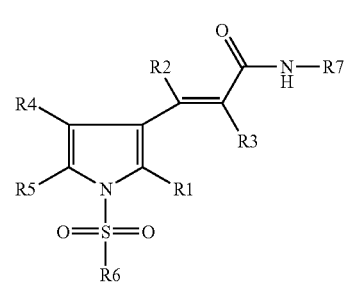

24 Claims, No Drawings

OTHER PUBLICATIONS

W. Fischle et al. "Enzymatic Activity Associated With Class II HDACs is Dependent on a Multiprotein Complex Containing HDAC3 and SMRT/N-Cor", *Molecular Cell*, vol. 9, pp. 45-58, 2002.

L. Gao et al. "Cloning and Functional Characterization of HDAC11, a Novel Member of the Human Histone Deacetylase Family", *J. Biol. Chem.*, vol. 277, No. 28, pp. 25748-25755, 2002.

P. George et al. "Combination of the Histone Deacetylase Inhibitor LBH589 and the HSP90 Inhibitor 17-AGG is Highly Active Against Human CML-BC Cells and AML Cells With Activating Mutation of FLT-3", *Blood*, vol. 105, pp. 1768-1777, 2005.

K. B. Glaser et al. "Role of Class I and Class II Histone Deacetylases in Carcinoma Cells Using siRNA", *Biochemical and Biophysical Research Communications*, vol. 310, pp. 529-536, 2003.

S. Haggarty et al. "Domain-Selective Small-Molecule Inhibitor of Histone Deacetylase 6 (HDAC6)-Mediated Tubulin Deacetylation", *J. Proc. Natl. Acad. Sci. USA*, vol. 100, No. 8, pp. 4389-4394, 2003.

L.Z. He et al. "Distinct Interactions of PML-RARα and PLZF-RARα With Co-Repressors Determine Differential Responses to RA in APL", *Nature Genetics*, vol. 18, pp. 126-135, 1998.

E. Hockly et al. "Suberoylanilide Hydroxamic Acid, A Histone Deacetylase Inhibitor, Ameliorates Motor Deficits in a Mouse Model of Huntington's Disease", *J. Proc. Natl. Acad. Sci. USA*, vol. 100, No. 4, pp. 2041-2046, 2003.

R. W. Johnstone et al. "Histone Deacetylase Inhibitors in Cancer Therapy: Is Transcription the Primary Target?", *Cancer Cell*, vol. 4, pp. 13-18, 2003.

S. Khochbin et al. "Functional Significance of Histone Deacetylase Diversity", *Current Opinion Gen. Dev.*, vol. 11, pp. 162-166, 2001.

M.S. Kim et al. "Inhibition of Histone Deacetylase Increases Cytotoxicity to Anticancer Drugs Targeting DNA", *Cancer Research*, vol. 63, pp. 7291-7300, 2003.

O. H. Kraemer et al. "Histone Deacetylase as a Therapeutic Target", *Trends in Endocrin. & Metabol*, vol. 12, No. 7, pp. 294-300, 2001.

G. Lagger et al. "Essential Fucntion of Histone Deacetylase 1 in Proliferation Control and CDK Inhibitor Repression", *EMBO*, vol. 21, pp. 2672-2681, 2002.

F. Leoni et al. "The Antitumor Histone Deacetylase Inhibitor Suberoylanilide Hydroxamic Acid Exhibits Anti-Inflammatory Properties via Suppression of Cytokines", *Proc. Natl. Acad. Sci. USA*. vol. 99, No. 5, pp. 2995-3000, 2002.

A. Mai et al. "3-(4-Aroyl-1-methyl-1 *H*-2-pyrrolyl)-*N*-Hydroxy-2-Alkylamides as a New Class of Synthetic Histone Deacetylase Inhibitors. 1. Design, Synthesis, Biological Evaluation, and Binding Mode Studies Performed Through Three Diffeent Docking Procedures", *J. Med. Chem.*, vol. 46, pp. 512-524, 2003.

P.A. Marks et al. "Histone Deacetylases and Cancer: Causes and Therapies", *Nature Reviews*, vol. 1, pp. 194-202, 2001.

T.A. Miller et al. "Patent Status of Histone Deacetylase Inhibitors", *Expert Opin. Ther. Patents*, vol. 14, No. 6, pp. 791-804, 2004.

T.A. Miller et al. "Histone Deacetylase Inhibitors", *J. of Med. Chem.*, vol. 46, No. 24, pp. 5098-5116, 2003.

N. Mishra et al. "Histone Deacetylase Inhibitors Modulate Renal Disease in the MRL-1pr Mouse", *J. Clin. Invest.*, vol. 111, pp. 539-552, 2003.

C.S. Mitsiades et al. "Transcriptional Signature of Histone Deacetylase Inhibition in Multiple Myeloma: Biological and Clinical Implications", *Proc. Natl. Acad. Sci. USA*, vol. 101, No. 2, pp. 539-552, 2004.

P.N. Munster et al. "The Histone Deacetylase Inhibitor Suberoylanilide Hydroxamic Acid Induces Differentiation of Human Breast Cancer Cells", *Cancer Research*, vol. 61, pp. 8492-8497, 2001.

T. Murata et al., "Defect of Histone Acetyltransferase Activity of the Nuclear Transcriptional Coactivator CBP in Rubinstein-Taybi Syndrome", *Human Molecular Genetics*, vol. 10, No. 10, pp. 1071-1076, 2001.

T. Nakayama et al. "Epigenetic Regulation of Androgen Receptor Gene Expression in Human Prostate Cancers", *Lab. Inv.*, vol. 80, No. 12, pp. 1789-1796, 2000.

R. Nimmanapalli et al. "Histone Deacetylase Inhibitor LAQ824 Both Lowers Expression and Promotes Proteasomal Degradation of Bcr-Abl and Induces Apoptosis of Imatinib Mesylate-Sensitive or -Refractory Chronic Myelogenous Leukemia-Blast Crisis Cells", *Cancer Research*, vol. 63, pp. 5126-5135, 2003.

K. Nishida et al. "Histone Deacetylase Inhibitor Suppression of Autoantibody-Mediated Arthritis in Mice via Regulation of p16$^{INK4a}$ and p21$^{WAF1/Cip1}$ Expression", *Arthritis Rheumatism*, vol. 50, No. 10, pp. 3365-3376, 2004.

R.L. Piekarz et al. "Inhibitor of Histone Deacetylation, Depsipeptide (FR901228), in the Treatment of Peripheral and Cutaneous T-Cell Lymphoma: a Case Report", *Blood*, vol. 98, pp. 2865, 2868, 2001.

R. Ragno et al. "3-(4-Aroyl-1-methyl-1H-pyrrol-2-y1)-N-hydroxy-2-propenamides as a New Class of Synthetic Histone Deacetylase Inhibitors. 3. Discovery of Novel Lead Compounds Through Structure-Based Drug Design and Docking Studies" *J. Med. Chem.*, vol. 47, pp. 1351-1359, 2004.

C.M. Reilly et al. "Modulation of Renal Disease in MRL/Ipr Mice by Suberoylanilide Hydroxamic Acid", *J. Immunol.*, vol. 173, pp. 4171-4178, 2004.

S.W. Remiszewski et al. "Recent Advances in the Discovery of Small Molecule Histone Deacetylase Inhibitors", *Current Opin. Drug Disc. Development*, vol. 5, No. 4, pp. 487-499, 2002.

A. J. Ruijter et al. "Histone Deacetylases (HDACs): Characterization of the Classical HDAC Family", *Biochem. J.*, vol. 370, pp. 737-749, 2003.

V. Sandor et al. "P21-Dependent $G_1$ Arrest With Downregulation of Cyclin D1 and Upregulation of Cyclin E by the Histone Deacetylase Inhibitor FR901228", *British J. of Cancer*, vol. 83, No. 6, pp. 817-825, 2000.

J. S. Steffan et al. "Histone Deacetylase Inhibitors Arrest Polyglutamine-Dependent Neurodegeneration in *Drosophila*", *Nature*, vol. 413, pp. 739-743, 2001.

B.D. Strohl et al. "The Language of Covalent Histone Modifications", *Nature*, vol. 403, pp. 41-45, 2000.

T. Tatamiya et al. "Isozyme-Selective Activity of the HDAC Inhibitor MS-275", AACR Annual Meeting [Abstract 2451], 2004.

C. Van Lint et al. "The Expression of a Small Fraction of Cellular Genes Is Changed in Response to Histone Hyperacetylation", *Gene Expression*, vol. 5, pp. 245-253, 1996.

E. Verdin et al. "Class II Histone Deacetylases: Versatile Regulators", *Trends in Genetics*, vol. 19, No.5, pp. 286-293, 2003.

J. Wang et al. "ETO, Fusion Partner in t (8;21) Acute Myeloid Leukemia, Represses Transcription by Interaction With the Human N-CoR/mSin3/HDAC1 Complex", *Proc. Natl. Acad. Sci. USA*, vol. 95, pp. 10860-10865, 1998.

X. Yang et al. "Transcriptional Activation of Estrogen Receptor α in Human Breast Cancer Cells by Histone Deacetylase Inhibition", *Cancer Research*, vol. 60, pp. 6890-6894, 2000.

P. Zhu et al. "Induction of HDAC2 Expression Upon Loss of APC in Colorectal Tumorigenesis", *Cancer Cells*, vol. 5, pp. 455-463, 2004.

A. Mai et al. "3-(4-Aroyl-1-methyl-1 *H*-2-pyrrolyl)-*N*-hydroxy-2-propenamides as a New Class of Synthetic Histone Deacetylase Inhibitors. 2. Effect of Pyrrole-$C_2$ and/or -$C_4$ Substitutions on Biological Activity", . *J. Med. Chem.*, vol. 47, pp. 1098-1109, 2004.

U.S. Appl. No. 12/822,641, filed Jun. 24, 2010.

Armeanu et al., Apoptosis on hepatoma cells but not on primary hepatocytes by histone deacetylase inhibitors valproate and ITF2357, J Hepatol., 210-217, 2005 (published online Nov. 10, 2004).

Butler et al., Suberoylanilide Hydroxamic Acid, an Inhibitor of Histone Deacetylase, Suppresses the Growth of Prostate Cancer Cells in Vitro and in Vivo, Canc. Res., 60, 5165-5170, 2000.

Butler et al., The histone deacetylase inhibitor SAHA arrests cancer cell growth, up-regulates thioredoxin-binding protein-2, and down-regulates thioredoxin, Proc. Natl. Acad. Sci., vol. 99, pp. 11700-11705, 2002.

Drummond et al., Clinical Development of Histone Deacetylase Inhibitors as Anticancer Agents, Annu. Rev. Pharm. Tox., 45:495-528, 2005 (published online Sep. 27, 2004).

Gui et al., Histone deacetylase (HDAC) inhibitor activation of p21WAF1 involves changes in promoter-associated proteins, including HDAC1, Proc. Natl. Acad. Sci., vol. 101, pp. 1241-1246, 2003.

Huang, Suberoylanilide Hydroxamic Acid as a Potential Therapeutic Agent for Human Breast Cancer Treatment, Molecular Medicine 6(10): 849-866, 2000.

Jaboin et al., MS-27-275, an Inhibitor of Histone Deacetylase, Has Marked in Vitro and in Vivo Antitumor Activity against Pediatric Solid Tumors, Canc. Res., 62:6108-6115, 2002.

Kelly et al., Histone Deacetylase Inhibitor: from target to clinical trials, Expert Opin. Invest. Drugs, 11(12), 1695-1713, 2002.

O'Neil et al., TAL1/SCL induces leukemia by inhibiting the transcriptional activity of E47/HEB, Canc. Cell, 5, 587-596, 2004.

Pasqualucci et al., Molecular Pathogenesis of Non-Hodgkin's Lymphoma: the Role of Bcl-6, Leukemia & Lymphoma, vol. 44, Supplement 3, pp. S5-S12, 2003.

Piekarz et al., Inhibitor of histone deacetylation, depsipeptide (FR901228), in the treatment of peripheral and cutaneous T-cell lymphoma: a case report, Blood, 98: 2865-2868, 2001.

Richon et al., Histone deacetylase inhibitor selectively induces p21WAF1 expression and gene-associated histone acetylation, Proc. Natl. Acad. Sci., vol. 97, pp. 10014-10019, 2000.

Rosato et al., The Histone Deacetylase Inhibitor MS-275 Promotes Differentiation or Apoptosis in Human Leukemia Cells through a Process Regulated by Generation of Reactive Oxygen Species and Induction of p21CIP1/WAF1, Canc. Res., 63, 3637-3645, Jul. 1, 2003.

Saito et al., A synthetic inhibitor of histone deacetylase, MS-27-275, with marked in vivo antitumor activity against human tumors, Proc. Natl. Acad. Sci. USA, vol. 96, pp. 4592-4597, 1999.

Sawa et al., Histone deacetylase inhibitor, FK228, induces apoptosis and suppresses cell proliferation of human glioblastoma cells in vitro and in vivo, Acta Neuropathol, 107 : 523-531, 2004.

Strait et al., Cell Cycle Blockade and Differentiation of Ovarian Cancer Cells by the Histone Deacetylase Inhibitor Trichostatin A Are Associated with Changes in p21, Rb, and Id Proteins, Mol. Cell. Canc., vol. 1, 1181-1190, 2002.

Villar-Garea, Histone Deacetylase Inhibitors: Understanding a new wave of anticancer agents, Int. J. Cancer, 112, 171-178, 2004.

Printout from Clinicaltrials.gov listing studies with search of HDAC cancer, printed Dec. 14, 2011.

* cited by examiner

SULFONYLPYRROLES

This application is a divisional of U.S. patent application Ser. No. 10/591,477 filed on Sep. 27, 2006 now U.S. Pat. No. 7,842,820.

FIELD OF APPLICATION OF THE INVENTION

The invention relates to novel N-sulphonylpyrrole derivatives, which are used in the pharmaceutical industry for the production of pharmaceutical compositions.

KNOWN TECHNICAL BACKGROUND

Transcriptional regulation in cells is a complex biological process. One basic principle is regulation by posttranslational modification of histone proteins, namely histone proteins H2A/B, H3 and H4 forming the octameric histone core complex. These complex N-terminal modifications at lysine residues by acetylation or methylation and at serine residues by phosphorylation constitute part of the so called "histone code" (Strahi & Ellis, Nature 403, 41-45, 2000). In a simple model, acetylation of positively charged lysine residues decreases affinity to negatively charged DNA, which now becomes accessible for the entry of transcription factors.

Histone acetylation and deacetylation is catalysed by histone acetyltransferases (HATs) and histone deacetylases (HDACs). HDACs are associated with transcriptional repressor complexes, switching chromatin to a transcriptionally inactive, silent structure (Marks at al. Nature Cancer Rev 1, 194-202, 2001). The opposite holds true for HATs which are associated with transcriptional activator complexes. Three different classes of HDACs have been described so far, namely class I (HDAC 1-3, 8) with Mr=42-55 kDa primarily located in the nucleus and sensitive towards inhibition by Trichostatin A (TSA), class II (HDAC 4-7, 9, 10) with Mr=120-130 kDa and TSA sensitivity and class III (Sir2 homologues) which are quite distinct by their $NAD^+$ dependency and ISA insensitivity (Ruijter at al. Biochem. J. 370, 737-749, 2003; Khochbin at al. Curr Opin Gen Dev II, 162-166, 2001; Verdin at al. Trends Gen 19, 286-293, 2003), HDAC 11 with Mr=39 kDa was cloned recently and displayed homology to class I and II family members (Gao at al. J Biol Chem 277, 25748-25755, 2002). HATs and HDACs exist in large complexes together with transcription factor and platform proteins in cells (Fischle et al. Mol Cell 9, 45-47, 2002). Surprisingly, only about 2% of all genes are regulated by histone acetylation (von Lint et al. Gene Expression 5, 245-253, 1996). New studies with SAHA in multiple myeloma cells showed that these transcriptional changes can be grouped into distinct functional gene classes important for eg regulation of apoptosis or proliferation (Mitsiades at al. Proc Natl Aoad Sci 101, pp 540, 2004). Substrates different to histone proteins exist. For HDACs these include transcription factors like p53 and TFII E/or chaperones like Hsp90 (Johnstone & Licht, Cancer Cell 4, 13-18, 2003). Therefore the correct name for HDACs would be lysine-specific protein deacetylases. As a consequence of these findings, inhibitors of HDACs effect not only chromatin structure and gone transcription but also protein function and stability by regulating protein acetylation in general. This function of HDACs in protein acetylation might also be important for understanding of immediate gene repression by treatment with HDis (von Lint et al. Gene Expression 5, 245-253, 1996). In this regard, proteins involved in oncogenic transformation and malignant cell growth are of particular importance.

Different publications highlight the importance of histone acetylation for cancer development (reviewed by Kramer et al. Trends Endocrin Metabol 12, 294-300, 2001; Marks et al. Nature Cancer Rev 1, 194-202, 2001). These diseases include
  (i) mutations of the HAT CAMP response element binding protein (COP) associated with Rubinstein-Taybi syndrome, a cancer predisposition (Murata et al. Hum Mol Genet 10, 1071-1076, 2001),
  (ii) aberrant recruitment of HDAC1 activity by transcription factors in acute promyelocytic leukemia (APL) by the PML-retinoic acid receptor cc fusion gene (He et al. Nat genet 18, 126-135, 1998)
  (iii) aberrant recruitment of HDAC activity by the overexpressed BCL6 protein in non-Hodgkins lymphoma (Dhordain et al. Nucleic Acid Res 26, 4645-4651, 1998) and finally
  (iv) aberrant recruitment of HDAC activity by the AML-ETO fusion protein in acute myelogenous leukemia (AML M2 subtype; Wang et al. Proc Natl Aced Sci USA 95, 10860-10865, 1998). In this AML subtype, the recruitment of HDAC1 activity causally leads to gene silencing, a differentiation block and oncogenic transformation.
  (v) HDAC1 gene knock-out in mice showed that HDAC1 has a profound function in embryonal stem cell proliferation by repressing cyclin-dependent kinase inhibitors $p21^{waf1}$ and $p27^{kip1}$ (Lagger et al. Embo J. 21, 2672-2681, 2002). Since $p21^{waf1}$ is induced by HDIs in many cancer cell lines, HDAC1 might be a crucial component in cancer cell proliferation as well. Initial siRNA based gene-knock down experiments in HeLa cells support this hypothesis (Glaser et al. 310, 529-536, 2003)
  (vi) HDAC2 is overexpressed in colon carcinoma upon constitutive activation of the wnt/β-catenin/TOF signalling pathay by loss of functional adenomatosis polyposis coil (APC) protein as reported by Zhu et al. recently (Cancer Cell 5, 455-463, 2004)

On the molecular level, a pleithora of published data with various HDAC inhibitors like Trichostatin A (TSA) showed that many cancer relevant genes are up- or down regulated. These include $p21^{CIP1}$, Cyclin E, transforming growth factor β (TGFβ), p53 or the von Hippel-Lindau (VHL) tumor suppressor genes, which are upregulated, whereas Bcl-XL, bcl2, hypoxia inducible factor (HIF) 1α, vascular endothelial growth factor (VEGF) and cyclin A/D are down-regulated by HDAC inhibition (reviewed by Kramer et al. Trends Endocrin Metabol 12, 294-300, 2001). HDAC inhibitors arrest cells at G1 and G2/M within the cell cycle and deplete S-phase cells, as shown for Depsipeptide as an example (Sander et al., British J Cancer 83, 817-825, 2000). HDAC inhibitory compounds induce p53 and caspase3/8 independent apoptosis and have broad anti-tumor activity. Anti-angiogenic activity was described also, which might be related to down-regulation of VEGF and HIF1α. In summary, HDAC inhibition effects tumor cells at different molecular levels and multiple cellular proteins are targeted.

Interestingly, HDAC inhibitors were found to induce cellular differentiation and this pharmacological activity might contribute to their anti-cancer activity as well. For example it was shown recently that suberoylanilide hydroxamic acid (SAHA) induces differentiation of breast cancer cell lines, exemplified by resynthesis of milk fat membrane globule protein (MFMG), milk fat globule protein and lipid (Munster et al. Cancer Res. 61, 8492, 2001).

There is growing rational for synergism of HDAC inhibitors with chemotherapeutic as well as target specific cancer drugs. For example, synergism was shown for SAHA with the kinase/cdk inhibitor flavopiridol (Alemenara at al. Leukemia 16, 1331-1343, 2002), for LAQ-824 with the bcr-abl kinase inhibitor Glivec in CML cells (Nimmanapaili at al. Cancer Ras. 63, 5126-5135, 2003) and for SAHA and Trichostatin A (TSA) with etoposide (VP16), cisplatin and doxorubicin (Kim at al. Cancer Res. 63, 7291-7300, 2003) and LBH589 with the hsp90 inhibitor 17-allyl-amino-demethoxy-geldanamycin (17-AAG; George at al. Blood online, Oct. 28, 2004). Also it was shown that HDAC inhibition causes reexpression of estrogen or androgen receptors in breast and prostate cancer cells with the potential to resensitize these tumors to anti-hormone therapy (Yang at al. Cancer Res. 60, 6890-6894, 2000; Nakayama et al. Lab Invest 80, 1789-1796, 2000).

HDAC inhibitors from various chemical classes were described in the literature with four most important classes, namely (i) hydroxamic acid analogs, (ii) benzamide analogs, (iii) cyclic peptides/peptolides and (iv) fatty acid analogs. A comprehensive summary of known HDAC inhibitors was published recently (Miller at al. J Med Chem 46, 5097-5116, 2003). There is only limited data published regarding specificity of these histone deacetylase inhibitors. In general most hydroxamate based HDI are not specific regarding class I and II HDAG enzymes. For example. TSA inhibits HDACs 1, 3, 4, 6 and 10 with $IC_K$, values around 20 nM, whereas HDAC8 was inhibited with $IC_{50}$=0.49 µM (Tatamiya at al, AACR Annual Meeting 2004, Abstract #2451). But there are exceptions like the experimental HDI Tubacin, selective for the class II enzyme HDAC 6 (Haggerty at al. Proc natl Aced Sci USA 100, 4389-4394, 2003). In addition, data on class I selectivity of benzamid HDIs are emerging. MS-275 Inhibited class I HDAC1 and 3 with $IC_{50}$=0.51 µM and 1.7 µM, respectively. In contrast class II HDACs 4, 6, 8 and 10 were inhibited with $IC_{50}$ values of >100 µM, >100 µM, 82.5 µM and 94.7 µM, respectively (Tatamiya at al, AACR Annual Meeting 2004, Abstract #2451). So far it is not clear if specificity towards HDAC class I or II enzymes or a defined single isoenzyme should be superior regarding therapeutic efficacy and index.

Clinical studies in cancer with HDAC inhibitors are ongoing, namely with SAHA (Merck Inc.), Valproic acid, FK228/Depsipeptide (Gloucester Pharmaceuticals/NCI), MS275 (Berlex-Schering), NVP LBH-589 (Novartis), PXD-101 (Topotarget/Curagen), MGCD0103 (methylgene Inc.) and Pivalayloxymethylbutyrate/Pivanex (Titan Pharmaceuticals). These studies showed first evidence of clinical efficacy, highlighted recently by partial and complete responses with FK228/Depsipeptide in patients with peripheral T-cell lymphoma (Plekarz et al. Blood, 98, 2865-2868, 2001).

Recent publications also showed possible medical use of HDAC inhibitors in disease different to cancer. These diseases include systemic lupus erythematosus (Mishra et al. J Clin Invest 111, 539-552, 2003; Reilly et al. J. Immunol. 173, 4171-4178, 2004), rheumatoid arthritis (Chung et al. Mol Therapy 8, 707-717, 2003; Nishida et al. Arthritis & Rheumatology 60, 3365-3376, 2004), inflammatory diseases (Leoni et al. Proc Natl Aced Sd USA 99, 2995-3000, 2002) and neurodegenerative diseases like Huntington's disease (Steffan et al. Nature 413, 739-743, 2001, Hockly et al. Proc Natl Aced Sci USA 100(4):2041-6, 2003).

Cancer chemotherapy was established based on the concept that cancer cells with uncontrolled proliferation and a high proportion of cells in mitosis are killed preferentially. Standard cancer chemotherapeutic drugs finally kill cancer cells upon induction of programmed cell death ("apoptosis") by targeting basic cellular processes and molecules, namely RNA/DNA (alkylating and carbamoylating agents, platin analogs and topoisomerase inhibitors), metabolism (drugs of this class are named anti-metabolites) as well as the mitotic spindle apparatus (stabilizing and destabilizing tubulin inhibitors). Inhibitors of histone deacetylases (HDIs) constitute a new class of anti cancer drugs with differentiation and apoptosis inducing activity. By targeting histone deacetylases, HDIs effect histone (protein) acetylation and chromatin structure, inducing a complex transcriptional reprogramming, exemplified by reactivation of tumor suppressor genes and repression of oncogenes. Beside effecting acetylation of N-terminal lysine residues in core histone proteins, non-histone targets important for cancer cell biology like heat-shock-protein 90 (Hsp90) or the p53 tumor suppressor protein exist. The medical use of HDIs might not be restricted to cancer therapy, since efficacy in models for inflammatory diseases, rheumatoid arthritis and neurodegeneration was shown.

Prior Art

Benzoyl or acetyl substituted pyrrolyl propenamides are described in the public literature as HDAC-inhibitors, whereas the connectivity of the acyl-group is at position 2 or 3 of the pyrrole scaffold. (Mai et. al., Journal Med. Chem. 2004, Vol. 47, No, 5, 1098-1109). Further pyrrolyl substituted hydroxamic acid derivatives are described in U.S. Pat. No. 4,960,787 as lipoxygenase inhibitors or in U.S. Pat. No. 6,432,999 as cyclooxygenase inhibitors.

Various compounds, which are said to be HDAC inhibitors, are reported in WO 01/38322; Journal Med. Chem. 2003, Vol. 46, No, 24, 5097-5116; Journal Med. Chem. 2003, Vol. 46, No. 4, 512-524; Journal Med. Chem. 2003, Vol, 46, No. 5, 820-830; and in Current Opinion Drug Discovery 2002, Vol, 5, 487-499. There remains a need in the art for new, well tolerated and more efficacious inhibitors of HDACs.

DESCRIPTION OF THE INVENTION

It has now been found that the N-sulphonylpyrrole derivatives, which are described in greater details below, differ profoundly from prior art compounds and are effective inhibitors of histone deacetylases and have surprising and particularly advantageous properties.

The invention thus relates, in a first aspect (aspect 1), to compounds of formula I

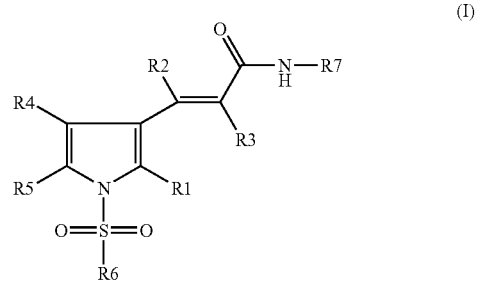

in which
R1 is hydrogen, 1-4C-alkyl, halogen, or 1-4C-alkoxy,
R2 is hydrogen or 1-4C-alkyl,
R3 is hydrogen or 1-4C-alkyl,
R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, in which
T1 is a bond, or 1-4C-alkylene,
Q1 is Ar1, Aa1, Hh1, or Ah1, in which
Ar1 is phenyl, or R61- and/or R62-substituted phenyl, in which R61 is 1-4C-alkyl, or -T2-N(R611)R612, in which
either
T2 is a bond, and
R611 is hydrogen, 1-4C-alkyl, hydroxy-2-4C-alkyl, 1-4C-alkoxy-2-4C-alkyl, phenyl-1-4C-alkyl, or Har1-1-4C-alkyl, in which
Har1 is optionally substituted by R6111 and/or R6112, and is a monocyclic or fused bicyclic 5- to 10-membered unsaturated heteroaromatic ring comprising one to three heteroatoms, each of which is selected from the group consisting of nitrogen, oxygen and sulfur, in which
R6111 is halogen, or 1-4C-alkyl,
R6112 is 1-4C-alkyl, and
R612 is hydrogen, 1-4C-alkyl, 1-4C-alkoxy-2-4C-alkyl or hydroxy-2-4C-alkyl,
or R611 and R612 together and with inclusion of the nitrogen atom, to which they are bonded, form a heterocyclic ring Het1, in which
Het1 is morpholino, thiomorpholino, S-oxo-thiomorpholino, S,S-dioxo-thiomorpholino, piperidino, pyrrolidino, piperazino, or 4N-(1-4C-alkyl)-piperazino, or
T2 is 1-4C-alkylene, or 2-4C-alkylene interrupted by oxygen, and
R611 is hydrogen, 1-4C-alkyl, hydroxy-2-4C-alkyl, 1-4C-alkoxy-2-4C-alkyl, phenyl-1-4C-alkyl, or Har1-1-4C-alkyl, in which
Har1 is optionally substituted by R6111 and/or R6112, and is a monocyclic or fused bicyclic 5- to 10-membered unsaturated heteroaromatic ring comprising one to three heteroatoms, each of which is selected from the group consisting of nitrogen, oxygen and sulfur, in which
R6111 is halogen, or 1-4C-alkyl,
R6112 is 1-4C-alkyl, and
R612 is hydrogen, 1-4C-alkyl, 1-4C-alkoxy-2-4C-alkyl or hydroxy-2-4C-alkyl,
or R611 and R612 together and with inclusion of the nitrogen atom, to which they are bonded, form a heterocyclic ring Het1, in which
Het1 is morpholino, thiomorpholino, S-oxo-thiomorpholino, S,S-dioxo-thiomorpholino, piperidine, pyrrolidino, piperazino, 4N-(1-4C-alkyl)-piperazino, imidazolo, pyrrolo or pyrazolo,
R62 is 1-4C-alkyl, 1-4C-alkoxy, halogen, cyano, 1-4C-alkoxy-1-4C-alkyl, 1-4C-alkylcarbonylamino, or 1-4C-alkylsulphonylamino,
Aa1 is a bisaryl radical made up of two aryl groups,
which are selected independently from a group consisting of phenyl and naphthyl, and
which are linked together via a single bond,
Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond,
Ah1 is a heteroaryl-aryl radical or an aryl-heteroaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond, R7 is hydroxyl, or Cyc1, in which
Cyc1 is a ring system of formula Ia

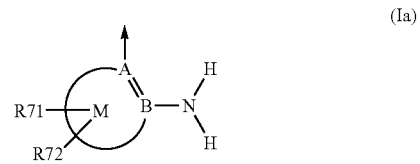

in which
A is C (carbon),
B is C (carbon),
R71 is hydrogen, halogen, 1-4C-alkyl, or 1-4C-alkoxy,
R72 is hydrogen, halogen, 1-4C-alkyl, or 1-4C-alkoxy,
M with inclusion of A and B is either a ring Ar2 or a ring Har2, in which
Ar2 is a benzene ring,
Har2 is a monocyclic 5- or 6-membered unsaturated heteroaromatic ring comprising one to three heteroatoms, each of which is selected from the group consisting of nitrogen, oxygen and sulfur,
and the salts of these compounds.

The invention relates, in a second aspect (aspect 2), to compounds of formula I
in which
R1 is hydrogen, 1-4C-alkyl, halogen, or 1-4C-alkoxy,
R2 is hydrogen or 1-4C-alkyl,
R3 is hydrogen or 1-4C-alkyl,
R4 is hydrogen, 1-4C-alkyl, halogen, or 1-4C-alkoxy,
R5 is hydrogen, 1-4C-alkyl, halogen, or 1-4C-alkoxy,
R6 is -T1-Q1, in which
T1 is a bond, or 1-4C-alkylene,
Q1 is Ar1, Aa1, Hh1, or Ah1, in which
Ar1 is phenyl, or R61- and/or R62-substituted phenyl, in which
R61 is 1-4C-alkyl, or -T2-N(R611)R612, in which
T2 is a bond, 1-4C-alkylene, or 2-4C-alkylene interrupted by oxygen,
R611 is hydrogen, 1-4C-alkyl, hydroxy-2-4C-alkyl, 1-4C-alkoxy-2-4C-alkyl, phenyl-1-4C-alkyl, or Har1-1-4C-alkyl, in which
Har1 is optionally substituted by R6111 and/or R6112, and is a monocyclic or fused bicyclic 5- to 10-membered unsaturated heteroaromatic ring comprising one to three heteroatoms, each of which is selected from the group consisting of nitrogen, oxygen and sulfur, in which
R6111 is halogen, or 1-4C-alkyl,
R6112 is 1-4C-alkyl,
R612 is hydrogen, 1-4C-alkyl, 1-4C-alkoxy-2-4C-alkyl or hydroxy-2-4C-alkyl,
R62 is 1-4C-alkyl, 1-4C-alkoxy, halogen, cyano, 1-4C-alkoxy-1-4C-alkyl, 1-4C-alkylcarbonylamino, or 1-4C-alkylsulphonylamino,
Aa1 is a bisaryl radical made up of two aryl groups,
which are selected independently from a group consisting of phenyl and naphthyl, and
which are linked together via a single bond,
Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and which are linked together via a single bond,
Ah1 is a heteroaryl-aryl radical or an aryl-heteroaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond,
R7 is hydroxyl, or Cyc1, in which
Cyc1 is a ring system of formula Ia

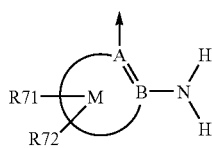

(Ia)

in which
A is C (carbon),
B is C (carbon),
R71 is hydrogen, halogen, 1-4C-alkyl, or 1-4C-alkoxy,
R72 is hydrogen, halogen, 1-4C-alkyl, or 1-4C-alkoxy,
M with inclusion of A and B is either a ring Ar2 or a ring Har2, in which
Ar2 is a benzene ring,
Har2 is a monocyclic 5- or 6-membered unsaturated heteroaromatic ring comprising one to three heteroatoms, each of which is selected from the group consisting of nitrogen, oxygen and sulfur,
and the salts of these compounds.

1-4C-alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

2-4C-Alkyl represents a straight-chain or branched alkyl radical having 2 to 4 carbon atoms. Examples which may be mentioned are the butyl, isobutyl, sec-butyl, tert-butyl, propyl, isopropyl and preferably the ethyl and propyl radicals.

1-4C-Alkylene is a branched or, particularly, straight chain alkylene radical having 1 to 4 carbon atoms. Examples which may be mentioned are the methylene (—CH$_2$—), ethylene (—CH$_2$—CH$_2$—), trimethylene (—CH$_2$—CH$_2$—CH$_2$—) and the tetramethylene (—CH$_2$—CH$_2$—CH$_2$—CH$_2$—) radical.

2-4C-Alkylene interrupted by oxygen stands for a straight chain alkylene radical having 1 to 4 carbon atoms which is suitably interrupted by an oxygen atom such as, for example, the [—CH$_2$CH$_2$—O—CH$_2$—CH$_2$—] radical.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

1-4C-Alkoxy-1-4C-alkyl represents one of the abovementioned 1-4C-alkyl radicals, which is substituted by one of the abovementioned 1-4C-alkoxy radicals. Examples which may be mentioned are the methoxymethyl, the methoxyethyl and the Isopropoxyethyl radicals, particularly the 2-methoxyethyl and the 2-isopropoxyethyl radicals.

1-4C-alkoxy-2-4C-alkyl represents one of the abovementioned 2-4C-alkyl radicals, which is substituted by one of the abovementioned 1-4C-alkoxy radicals. Examples which may be mentioned are the methoxyethyl, ethoxyethyl and the isopropoxyethyl radicals, particularly the 2-methoxyethyl, the 2-ethoxyethyl and the 2-isopropoxyethyl radicals.

Hydroxy-2-4C-alkyl represents one of the abovementioned 2-4C-alkyl radicals, which is substituted by a hydroxy radical. An example which may be mentioned is the 2-hydroxyethyl or the 3-hydroxypropyl radical.

Phenyl-1-4C-alkyl stands for one of the abovementioned 1-4C-alkyl radicals, which is substituted by a phenyl radical. Examples which may be mentioned are the benzyl and the phenethyl radicals.

Halogen within the meaning of the invention is bromine or, in particular, chlorine or fluorine.

1-4C-alkylcarbonyl represents a radical which, in addition to the carbonyl group, contains one of the abovementioned 1-4C-alkyl radicals. An example which may be mentioned is the acetyl radical.

1-4C-alkylcarbonylamino represents an amino radical which is substituted by one of the above-mentioned 1-4C-alkylcarbonyl radicals. An example which may be mentioned is the acetamido radical [CH$_3$C(O)—NH—].

1-4C-alkylsulphonylamino is, for example, the propylsulfonylamino [C$_3$H$_7$S(O)$_2$NH—], the ethylsulfonylamino [C$_2$H$_5$S(O)$_2$NH—] and the methylsulfonylamino [CH$_3$S(O)$_2$NH—] radical.

Aa1 is a bisaryl radical made up of two aryl groups,
which are selected independently from a group consisting of phenyl and naphthyl, and
which are linked together via a single bond.

Aa1 may include, without being restricted thereto, the biphenyl radical, e.g. the 1,1'-biphen-4-yl or 1,1'-biphen-3-yl radical.

Hh1 is a bisheteroaryl radical made up of two heteroaryl groups,
which are selected independently from a group consisting of monocyclic 5- or 6-membered heteroaryl radicals comprising one or two heteroatoms, each of which is selected from the group consisting of nitrogen, oxygen and sulfur, and
which are linked together via a single bond.

Hh1 may include, without being restricted thereto, the bithiophenyl, bipyridyl, pyrazolyl-pyridinyl (particularly pyrazol-1-yl-pyridinyl), imidazolyl-pyridinyl (particularly imidazol-1-yl-pyridinyl) or the pyridinyl-thiophenyl radical, e.g. the 5-(pyridin-2-yl)-thiophen-2-yl radical.

In a special detail, exemplary Hh1 radicals may include pyridinyl-thiophenyl, e.g. 5-(pyridin-2-yl)-thiophen-2-yl.

Ah1 is a heteroarylaryl radical or an arylheteroaryl radical made up of a heteroaryl group selected from a group consisting of monocyclic 5- or 6-membered heteroaryl radicals comprising one or two heteroatoms, each of which is selected from the group consisting of nitrogen, oxygen and sulfur, and an aryl group selected from a group consisting of phenyl and naphthyl, whereby said heteroaryl and aryl groups are linked together via a single bond.

The Ah1 radical can be bonded either via said heteroaryl or via said aryl moiety to the parent molecular group.

A particular embodiment of said Ah1 radicals refers to heteroaryl-phenyl radicals, e.g. 3-(heteroaryl)-phenyl or 4-(heteroaryl)-phenyl radicals.

Ah1 may include, without being restricted thereto, the phenyl-thiophenyl or phenyl-pyridyl radicals.

Alternatively, Ah1 may include, without being restricted thereto the furanyl-phenyl, pyrazolyl-phenyl (e.g. pyrazol-1-yl-phenyl or 1H-pyrazol-4-yl-phenyl), imidazolyl-phenyl (e.g. imidazol-1-yl-phenyl) or pyridinyl-phenyl radicals.

In a special detail, exemplary Ah1 radicals may include 3-(pyrazolyl)-phenyl, 4-(pyrazolyl)-phenyl, 4-(pyridinyl)-phenyl or 3-(pyridinyl)-phenyl.

In a further special detail, exemplary Ah1 radicals may include 3-(pyrazol-1-yl)-phenyl, 4-(pyrazol-1-yl)-phenyl, 4-(pyridin-4-yl)-phenyl, 3-(pyridin-4-yl)-phenyl, 4-(pyridin-3-yl)-phenyl, 3-(pyridin-3-yl)-phenyl, 3-(1H-pyrazol-4-yl)-phenyl or 4-(1H-pyrazol-4-yl)-phenyl.

It is to be stated, that each of the radicals Hh1 and Ah1 is bonded preferably via a ring carbon atom to the moiety T1.

Har1 is optionally substituted by R6111 and/or 86112, and is a monocyclic or fused bicyclic 5- to 10-membered unsaturated (heteroaromatic) heteroaryl radical comprising one to three heteroatoms, each of which is selected from the group consisting of nitrogen, oxygen and sulfur. In one detail, fused, in particular benzo-fused, bicyclic 9- or 10-membered heteroaryl radicals comprising one to three, in particular one or two, heteroatoms, each of which is selected from the group consisting of nitrogen, oxygen and sulfur, are to be mentioned. Examples of Har1 include, without being restricted thereto, thiophenyl, (uranyl, pyrrolyl, oxazolyl, isoxazolyl, pyrazolyl, imidazolyl, thiazolyl, isothiazolyl, triazolyl, oxadiazolyl, thiadiazolyl, pyridinyl, pyrimidinyl, pyrazinyl or pyridazinyl; and, in particular, the stable benzo-fused derivatives thereof, such as e.g. benzothiophenyl, benzofuranyl, indolyl, benzoxazolyl, benzothiazolyl, indazolyl, benzimidazolyl, benzisoxazolyl, benzisothiazolyl, benzofurazanyl, quinolinyl, isoquinolinyl, quinazolinyl, quinoxalinyl, phthalazinyl or cinnolinyl; and purinyl, indolizinyl, naphthyridinyl or pteridinyl.

In a special detail, exemplary Har1 radicals may include pyridinyl, benzimidazolyl, benzoxazolyl, benzofuranyl, benzothiophenyl and indolyl, such as e.g. pyridin-2-yl, pyridin-3-yl, pyridin-4-yl, benzimidazol-2-yl, benzoxazol-2-yl, benzofuran-2-yl, benzofuran-3-yl, benzothiophen-2-yl, benzothiophen-3-yl, indol-2-yl, indol-3-yl or indol-5-yl.

In a further special detail, an exemplary Har1 radical may be indolyl, such as e.g. Indol-2-yl, indol-3-yl or indol-6-yl.

Yet in a further special detail, an exemplary Har1 radical may be pyridinyl, such as e.g. pyridin-2-yl, pyridin-3-yl or pyridin-4-yl.

As further examples of Har1, the R6111- and/or R6112-substituted derivatives of the above-mentioned exemplary Har1 radicals may be mentioned.

Har1-1-4C-alkyl stands for one of the abovementioned 1-4C-alkyl radicals, such as e.g. methyl, ethyl or propyl, substituted by one of the abovementioned Har1 radicals, such as e.g. imidazolyl, benzimidazolyl, indolyl or pyrrolyl and the like or the substituted derivatives thereof. As examples may be mentioned, without being restricted thereto, pyridinylmethyl (e.g. pyridin-3-yl-methyl), imidazolylmethyl, pyrrolylmethyl, 2-imidazolylethyl (e.g. 2-imidazol-5-yl-ethyl), 2-pyridinylethyl, 3-(benzofuran-2-yl)propyl, 3-(benzimidazol-2-yl)propyl, 2-indolylethyl (e.g. 2-indol-2-yl-ethyl or 2-indol-3-yl-ethyl), indolylmethyl (e.g. indol-2-yl-methyl, indol-3-yl-methyl or indol-5-yl-methyl), 2-benzimidazolylethyl (e.g. 2-benzimidazol-2-ylethyl), benzimidazolylmethyl (e.g. benzimidazol-2-yl-methyl), and the like.

In a special detail, exemplary Har1-1-4C-alkyl radicals may include pyridinylmethyl (e.g. pyridin-3-yl-methyl, pyridin-4-yl-methyl or pyridin-4-yl-methyl), 2-pyridinylethyl (e.g. 2-pyridin-3-yl-ethyl), indolylmethyl (e.g. indol-2-yl-methyl, indol-3-yl-methyl or indol-5-yl-methyl) or 2-indolylethyl (e.g. 2-indolyl-2-yl-ethyl or 2-indolyl-3-yl-ethyl).

In a further special detail, exemplary Har1-1-4C-alkyl radicals may include pyridin-3-yl-methyl, pyridin-4-yl-methyl, 2-pyridin-3-yl-ethyl, indol-2-yl-methyl, indol-3-yl-methyl, indol-5-yl-methyl, 2-indolyl-2-yl-ethyl or 2-indolyl-3-yl-ethyl.

In the context of the radical Har1-1-4C-alkyl, it is to be stated, that the portion Har1 is bonded preferably via a ring carbon atom to the 1-4C-alkyl moiety.

One embodiment of those Har1-1-4C-alkyl radicals, in which the Har1 moiety is a fused bicyclic ring containing a benzene ring, refers to those radicals, in which the Har1 moiety is preferably bonded to the 1-4C-alkyl moiety via a carbon ring atom of the ring comprising one or more heteroatoms.

Another embodiment of those Har1-1-4C-alkyl radicals, in which the Har1 moiety is a fused bicyclic ring containing a benzene ring, refers to those radicals, in which the Har1 moiety is preferably bonded to the 1-4C-alkyl moiety via a carbon ring atom of the benzene ring:

Har2 stands for a monocyclic 5- or 6-membered unsaturated heteroaromatic ring comprising one to three heteroatoms, each of which is selected from the group consisting of nitrogen, oxygen and sulfur. Har2 may include, without being restricted thereto, thiophene, oxazole, isoxazole, thiazole, isothiazole, imidazole, pyrazole, triazole, thiadiazole, oxadiazole, pyridine, pyrimidine, pyrazine or pyridazine.

In a special detail, an exemplary Har2 radical may be pyridine.

Cyc1 stands for a ring system of formula Ia, which is bonded to the nitrogen atom of the carboxamide group via the moiety A. Cyc1 may include, without being restricted thereto, 2-aminophenyl substituted by R71 and/or R72.

Naphthyl, alone or as part of another group, includes naphthalen-1-yl and naphthalen-2-yl.

In the meaning of the present invention, it is to be understood, that, when two structural portions of the compounds according to this invention are linked via a constituent which has the meaning "bond", then said two portions are directly attached to another via a single bond.

In general, unless otherwise mentioned the heterocyclic groups mentioned herein refer to all of the possible isomeric forms thereof.

The heterocyclic groups mentioned herein refer, unless otherwise noted, in particular to all of the possible positional isomers thereof.

Thus, for example, the term pyridyl or pyridinyl, alone or as part of another group, includes pyridin-2-yl, pyridin-3-yl and pyridin-4-yl.

Constituents which are optionally substituted as stated herein, may be substituted, unless otherwise noted, at any possible position.

The carbocyclic groups, alone or as part of other groups, mentioned herein may be substituted by their given substituents or parent molecular groups, unless otherwise noted, at any substitutable ring carbon atom.

The heterocyclic groups, alone or as part of other groups, mentioned herein may be substituted by their given substituents or parent molecular groups, unless otherwise noted, at any possible position, such as e.g. at any substitutable ring carbon or ring nitrogen atom.

Rings containing quaternizable imino-type ring nitrogen atoms (—N═) may be preferably not quaternized on these imino-type ring nitrogen atoms by the mentioned substituents or parent molecular groups.

Any heteroatom of a heterocyclic ring with unsatisfied valences mentioned herein is assumed to have the hydrogen atom(s) to satisfy the valences.

When any variable occurs more than one time in any constituent, each definition is independent.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

The substituents R61 and R62 of compounds of formula I can be attached in the ortho, meta or para position with respect to the binding position in which the phenyl ring is bonded to T1, whereby preference is given to the attachment in the meta or, particularly, in the para position.

In another embodiment, Ar1 is phenyl which is mono-substituted by R61, whereby preference is given to the attachment of R61 in the meta or para position with respect to the binding position in which the phenyl ring is bonded to T1.

In yet another embodiment, Ar1 is phenyl which is mono-substituted by R61, whereby preference is given to the attachment of R61 in the para position with respect to the binding position in which the phenyl ring is bonded to T1.

In still yet another embodiment, Ar1 is phenyl which is mono-substituted by R61, whereby preference is given to the attachment of R61 in the meta position with respect to the binding position in which the phenyl ring is bonded to T1.

Compounds according to aspect 1 of the present invention more worthy to be mentioned are those compounds of formula I
in which
R1 is hydrogen, or 1-4C-alkyl,
R2 is hydrogen, or 1-4C-alkyl,
R3 is hydrogen, or 1-4C-alkyl,
R4 is hydrogen, or 1-4C-alkyl,
R5 is hydrogen, or 1-4C-alkyl,
R6 is -T1-Q1, in which
T1 is a bond, or 1-4C-alkylene,
Q1 is Ar1, Aa1, Hh1, or Ah1, in which
Ar1 is phenyl, or R61-substituted phenyl, in which
R61 is 1-4C-alkyl, or -T2-N(R611)R612, in which
either
T2 is a bond, R611 is hydrogen, 1-4C-alkyl, phenyl-1-4C-alkyl, or Har1-1-4C-alkyl, in which
Har1 is either
  a monocyclic 5-membered unsaturated heteroaromatic ring comprising one, two or three heteroatoms, each of which is selected from the group consisting of nitrogen, oxygen and sulfur, or
  a monocyclic 6-membered unsaturated heteroaromatic ring comprising one or two nitrogen atoms, or
  a fused bicyclic 9-membered unsaturated heteroaromatic ring comprising one, two or three heteroatoms, each of which is selected from the group consisting of nitrogen, oxygen and sulfur, or
  a fused bicyclic 10-membered unsaturated heteroaromatic ring comprising one or two heteroatoms, each of which is selected from the group consisting of nitrogen, oxygen and sulfur, and
R612 is hydrogen, 1-4C-alkyl, or hydroxy-2-4C-alkyl,
or R611 and R612 together and with inclusion of the nitrogen atom, to which they are bonded, form a heterocyclic ring Het1, in which
Het1 is morpholino, or
T2 is 1-4C-alkylene,
R611 is hydrogen, 1-4C-alkyl, phenyl-1-4C-alkyl, or Har1-1-4C-alkyl, in which
Har1 is either
  a monocyclic 5-membered unsaturated heteroaromatic ring comprising one, two or three heteroatoms, each of which is selected from the group consisting of nitrogen, oxygen and sulfur, or
  a monocyclic 6-membered unsaturated heteroaromatic ring comprising one or two nitrogen atoms, or
  a fused bicyclic 9-membered unsaturated heteroaromatic ring comprising one, two or three heteroatoms, each of which is selected from the group consisting of nitrogen, oxygen and sulfur, or
  a fused bicyclic 10-membered unsaturated heteroaromatic ring comprising one or two heteroatoms, each of which is selected from the group consisting of nitrogen, oxygen and sulfur, and
R612 is hydrogen, 1-4C-alkyl, or hydroxy-2-4C-alkyl,
or R611 and R612 together and with inclusion of the nitrogen atom, to which they are bonded, form a heterocyclic ring Het1, in which
Het1 is morpholino,
Aa1 is a biphenyl radical,
Hh1 is a bipyridyl, pyrazolyl-pyridinyl, imidazolyl-pyridinyl, or pyridinyl-thiophenyl radical,
Ah1 is a pyridinyl-phenyl, pyrazolyl-phenyl, or imidazolyl-phenyl radical,
R7 is hydroxyl, or 2-aminophenyl,
and the salts of these compounds.

Compounds according to aspect 2 of the present invention more worthy to be mentioned are those compounds of formula I
in which
R1 is hydrogen, or 1-4C-alkyl,
R2 is hydrogen, or 1-4C-alkyl,
R3 is hydrogen, or 1-4C-alkyl,
R4 is hydrogen, or 1-4C-alkyl,
R5 is hydrogen, or 1-4C-alkyl,
R6 is -T1-Q1, in which
T1 is a bond, or 1-4C-alkylene,
Q1 is Ar1, or Aa1, in which
Ar1 is phenyl, or R61-substituted phenyl, in which
R61 is 1-4C-alkyl, or -T2-N(R611)R612, in which
T2 is a bond, or 1-4C-alkylene, R611 is hydrogen, 1-4C-alkyl, or Har1-1-4C-alkyl, in which
Har1 is imidazolyl, benzimidazolyl, indolyl or pyrrolyl,
R612 is hydrogen, or 1-4C-alkyl,
Aa1 is a biphenyl radical,
R7 is hydroxyl, or 2-aminophenyl,
and the salts of these compounds.

Compounds according to aspect 1 of the present invention in particular worthy to be mentioned are those compounds of formula I
in which
R1 is hydrogen,
192 is hydrogen,
113 is hydrogen,
R4 is hydrogen,
R5 is hydrogen,
R6 is -T1-Q1, Aa1, Hh1, or Ah1, in which
T1 is a bond, or 1-2C-alkylene,
Q1 is Ar1, in which
Ar1 is phenyl, or R61-substituted phenyl, in which
R61 is 1-4C-alkyl, or -T2-N(R611)R612, in which either
T2 is a bond,
R611 is hydrogen, 1-4C-alkyl, phenyl-1-2C-alkyl, or Har1-1-2C-alkyl, in which
Har1 is pyridinyl, benzimidazolyl, benzoxazolyl, benzofuranyl, benzothiophenyl or indolyl, and
R612 is hydrogen, 1-4C-alkyl, or hydroxy-2-3C-alkyl,
or R611 and R612 together and with inclusion of the nitrogen atom, to which they are bonded, form a heterocyclic ring Het1, in which
Het1 is morpholino,
or
T2 is 1-2C-alkylene,
R611 is hydrogen, 1-4C-alkyl, phenyl-1-2C-alkyl, or Har1-1-2C-alkyl, in which
Har1 is pyridinyl, benzimidazolyl, benzoxazolyl, benzofuranyl, benzothiophenyl or indolyl, and
R612 is hydrogen, 1-4C-alkyl, or hydroxy-2-3C-alkyl,
or R611 and R612 together and with inclusion of the nitrogen atom, to which they are bonded, form a heterocyclic ring Het1, in which
Het1 is morpholino,
Aa1 is a biphenyl radical,
Hh1 is a bipyridyl, pyrazolyl-pyridinyl, imidazolyl-pyridinyl, or pyridinyl-thiophenyl radical,
Ah1 is a pyridinyl-phenyl, pyrazolyl-phenyl, or imidazolyl-phenyl radical,
R7 is hydroxyl, or 2-aminophenyl,
and the salts of these compounds.

Compounds according to aspect 2 of the present invention in particular worthy to be mentioned are those compounds of formula
in which
R1 is hydrogen,
R2 is hydrogen,
R3 is hydrogen,
R4 is hydrogen,
R5 is hydrogen,
R6 is -T1-Q1, or biphenyl, in which
T1 is a bond, or 1-2C-alkylene,
Q1 is Ar1, in which
Ar1 is phenyl, or R61-substituted phenyl, in which
R61 is 1-4C-alkyl, or -T2-N(R611)R612, in which
T2 is a bond, or 1-2C-alkylene,
R611 is 1-4C-alkyl, or Har1-1-2C-alkyl, in which
Har1 is benzimidazolyl or indolyl,
R612 is 1-4C-alkyl,
R7 is hydroxyl, or 2-aminophenyl,
and the salts of these compounds.

Compounds according to aspect 1 of the present invention in more particular worthy to be mentioned are those compounds of formula I
in which
R1 is hydrogen,
R2 is hydrogen,
R3 is hydrogen,
R4 is hydrogen,
R5 is hydrogen,
R6 is -T1-Q1, Aa1, Hh1, Ah1, or benzyl, in which
T1 is a bond,
Q1 is Ar1, in which
Ar1 is phenyl, or R61-substituted phenyl, in which
R61 is 1-4C-alkyl, or -T2-N(R611)R612, in which either
T2 is a bond,
R611 is 1-4C-alkyl, and
R612 is 1-4C-alkyl,
or
T2 is 1-2C-alkylene,
R611 is hydrogen, 1-4C-alkyl, phenyl-1-2C-alkyl, or Har1-1-2C-alkyl, in which
Har1 is pyridinyl, or indolyl, and
R612 is hydrogen, 1-4C-alkyl, or hydroxy-2-3C-alkyl,
or R611 and R612 together and with inclusion of the nitrogen atom, to which they are bonded, form a heterocyclic ring Het1, in which
Het1 is morpholine,
Aa1 is 1,1-biphen-4-yl or 1,1'-biphen-3-yl,
Hh1 is a pyridinyl-thiophenyl radical,
Ah1 is a 3-(pyridinyl)-phenyl, 3-(pyrazolyl)-phenyl, 4-(pyridinyl)-phenyl or 4-(pyrazolyl)-phenyl radical,
R7 is hydroxyl, or 2-aminophenyl,
and the salts of these compounds.

Compounds according to aspect 2 of the present invention in more particular worthy to be mentioned are those compounds of formula I
in which
R1 is hydrogen,
R2 is hydrogen,
R3 is hydrogen,
R4 is hydrogen,
R5 is hydrogen,
R6 is -T1-Q1, biphenyl, or benzyl, in which
T1 is a bond,
is Ar1, in which
Ar1 is R61-substituted phenyl, in particular 4-(R61)-phenyl, in which
R61 is methyl, dimethylamino, or -T2-N(R611)R612, in which
T2 is methylene,
R611 is methyl or 2-(indol-2-yl)ethyl,
R612 is methyl,
R7 is hydroxyl, or 2-aminophenyl,
and the salts of these compounds.

Compounds according to aspect 1 of the present invention to be emphasized are those compounds of formula I
in which
R1 is hydrogen,
R2 is hydrogen,
R3 is hydrogen,
R4 is hydrogen,
R5 is hydrogen,
R6 is -T1-Q1, Aa1, Hh1, Ah1, or benzyl, in which
T1 is a bond,
Q1 is Ar1, in which
Ar1 is phenyl, 3-(R61)-phenyl, or 4-(R61)-phenyl, in which R61 is methyl, or -T2-N(R611)R612, in which
either
T2 is a bond,
R611 is methyl, and
R612 is methyl,
or
T2 is methylene,
R611 is hydrogen, methyl, isobutyl, benzyl, Har1-methyl, or
   2-(Har1)-ethyl in which
Har1 is pyridinyl or indolyl, and
R612 is hydrogen, methyl, or 2-hydroxy-ethyl,
or R611 and R612 together and with inclusion of the nitrogen
   atom, to which they are bonded, form a heterocyclic ring
   Het1, in which
Het1 is morpholino,
Aa1 is 1,1'-biphen-4-yl or 1,1'-biphen-3-yl,
Hh1 is a pyridinyl-thiophenyl radical,
Ah1 is a 3-(pyridinyl)-phenyl, 3-(pyrazolyl)-phenyl, 4-(pyridinyl)-phenyl or 4-(pyrazolyl)-phenyl radical,
R7 is hydroxyl, or 2-aminophenyl,
and the salts of these compounds.

Compounds according to aspect 1 of the present invention to be more emphasized are those compounds of formula I
in which
R1 is hydrogen,
R2 is hydrogen,
R3 is hydrogen,
R4 is hydrogen,
R5 is hydrogen,
R6 is -T1-Q1, Aa1, Hh1, Ah1, or benzyl, in which
T1 is a bond,
is Ar1, in which
Ar1 is phenyl, 3-(R61)-phenyl, or 4-(R61)-phenyl, in which
R61 is methyl, or -T2-N(R611)R612, in which
either
T2 is a bond,
R611 is methyl, and
R612 is methyl,
or
T2 is methylene,
R611 is hydrogen, methyl, isobutyl, benzyl, Har1-methyl, or
   2-(Har1)-ethyl in which
Har1 is pyridin-3-yl, pyridin-4-yl, indol-2-yl, indol-3-yl or
   indol-5-yl, and
R612 is hydrogen, methyl, or 2-hydroxy-ethyl,
or R611 and 8612 together and with inclusion of the nitrogen
   atom, to which they are bonded, form a heterocyclic ring
   Het1, in which
Het1 is morpholino,
Aa1 is 1,1'-biphen-4-yl or 1,1'-biphen-3-yl,
Hh1 is 5-(pyridin-2-yl)-thiophen-2-yl,
Ah1 is 3-(pyridin-3-yl)-phenyl, 3-(pyridin-4-yl)-phenyl,
   3-(pyrazol-1-yl)-phenyl, 3-(1H-pyrazol-4-yl)-phenyl,
   4-(pyridin-3-yl)-phenyl, 4-(pyridin-4-yl)-phenyl, 4-(pyrazol-1-yl)-phenyl or 4-(1H-pyrazol-4-yl)-phenyl,
R7 is hydroxyl, or 2-aminophenyl,
and the salts of these compounds.

Compounds according to aspect 1 of the present invention to be in particular emphasized are those compounds of formula I
in which
R1 is hydrogen,
R2 is hydrogen,
R3 is hydrogen,
R4 is hydrogen,
R5 is hydrogen,
R6 is -T1-Q1, Aa1, Hh1; Ah1, or benzyl, in which
T1 is a bond,
Q1 is Ar1, in which
Ar1 is phenyl, 3-(R61)-phenyl, or 4-(R61)-phenyl, in which
R61 is methyl, or -T2-N(R611)R612, in which
either
T2 is a bond,
R611 is methyl, and
R612 is methyl,
or
T2 is methylene,
R611 is hydrogen, isobutyl, benzyl, Har1-methyl, or
   2-(Har1)-ethyl, in which
Har1 is pyridin-3-yl, pyridin-4-yl, indol-2-yl, indol-3-yl or
   indol-5-yl, and
R612 is hydrogen,
or
T2 is methylene,
R611 is methyl, or 2-(Har1)-ethyl, in which
Har1 is indol-2-yl, and
R612 is methyl,
or
T2 is methylene,
R611 is 2-(Har1)-ethyl, in which
Har1 is indol-2-yl, and
R612 is 2-hydroxy-ethyl,
or
T2 is methylene, and
R611 and R612 together and with inclusion of the nitrogen
   atom, to which they are bonded, form a heterocyclic ring
   Het1, in which
Het1 is morpholino,
Aa1 is 1,1'-biphen-4-yl or 1,1'-biphen-3-yl,
Hh1 is 5-(pyridin-2-yl)-thiophen-2-yl,
Ah1 is 3-(pyridin-3-yl)-phenyl, 3-(pyridin-4-yl)-phenyl,
   3-(pyrazol-1-yl)-phenyl, 3-(1H-pyrazol-4-yl)-phenyl,
   4-(pyridin-3-yl)-phenyl, 4-(pyridin-4-yl)-phenyl, 4-(pyrazol-1-0)-phenyl or 4-(1H-pyrazol-4-yl)-phenyl,
R7 is hydroxyl,
and the salts of these compounds.

Yet compounds according to aspect 1 of the present invention to be in particular emphasized are those compounds of formula I
in which
R1 is hydrogen,
R2 is hydrogen,
R3 is hydrogen,
R4 is hydrogen,
R5 is hydrogen,
R6 is -T1-Q1, Aa1, Hh1, Ah1, or benzyl, in which
T1 is a bond,
Q1 is Ar1, in which
Ar1 is phenyl, 3-(R61)-phenyl, or 4-(R61)-phenyl, in which
R61 is methyl, or -T2-N(R611)R612, in which
either
T2 is a bond,
R611 is methyl, and
R612 is methyl,
or
T2 is methylene,
R611 is hydrogen, isobutyl, benzyl, Har1-methyl, or
   2-(Har1)-ethyl, in which
Har1 is pyridin-3-yl, pyridin-4-yl, indol-3-yl, or indol-5-yl,
   and
R612 is hydrogen,
or
T2 is methylene,
R611 is methyl, or 2-(Har1)-ethyl, in which Har1 is indol-2-yl, and
R612 is methyl,
or
T2 is methylene,
R611 is 2-(Har1)-ethyl, in which
Har1 is indol-2-yl, and
R612 is 2-hydroxy-ethyl,
or
T2 is methylene, and
R611 and R612 together and with inclusion of the nitrogen atom, to which they are bonded, form a heterocyclic ring Het1, in which
Het1 is morpholino,
Aa1 is 1,1'-biphen-4-yl or 1,1'-biphen-3-yl,
Hh1 is 5-(pyridin-2-yl)-thiophen-2-yl,
Ah1 is 3-(pyridin-3-yl)-phenyl, 3-(pyridin-4-yl)-phenyl, 3-(pyrazol-1-yl)-phenyl, 3-(1H-pyrazol-4-yl)-phenyl, 4-(pyridin-3-yl)-phenyl, 4-(pyridin-4-yl)-phenyl, 4-(pyrazol-1-yl)-phenyl or 4-(1H-pyrazol-4-yl)-phenyl,
R7 is 2-aminophenyl,
and the salts of these compounds.

A special interest in the compounds according to the present invention refers to those compounds of this invention which are included—within the scope of this invention—by one or, when possible, a combination of more of the following embodiments:

An embodiment of the compounds according to the present invention relates to those compounds of formula I, in which R1, R2, R3, R4 and R5 are all hydrogen.

A further embodiment of the compounds according to the present invention relates to those compounds of formula I, in which R7 is hydroxyl.

A further embodiment of the compounds according to the present invention relates to those compounds of formula I, in which R7 is Cyc1, whereby in a subembodiment thereof. Cyc1 is 2-phenyl.

A further embodiment of the compounds according to the present invention relates to those compounds of formula I, in which R7 is 2-aminophenyl.

A further embodiment of the compounds according to the present invention relates to those compounds of formula I, in which R6 is Aa1.

A further embodiment of the compounds according to the present invention relates to those compounds of formula I, in which R6 is Ar1 or —CH$_2$—Ar1.

A further embodiment of the compounds according to the present invention relates to those compounds of formula I, in which Ar1 is R161-substituted phenyl.

A further embodiment of the compounds according to the present invention relates to those compounds of formula I, in which Ar1 is phenyl monosubstituted by R61 in the meta position with respect to the binding position in which the phenyl ring is bonded to T1.

A further embodiment of the compounds according to the present invention relates to those compounds of formula I, in which Ar1 is phenyl monosubstituted by R61 in the para position with respect to the binding position in which the phenyl ring is bonded to T1.

A further embodiment of the compounds according to the present invention relates to those compounds of formula I, in which R6 is Hh1.

A further embodiment of the compounds according to the present invention relates to those compounds of formula I, in which R6 is Ah1.

A further embodiment of the compounds according to the present invention relates to those compounds of formula I, in which T2 is a bond.

A further embodiment of the compounds according to the present invention relates to those compounds of formula I, in which T2 is 1-4C-alkylene, such as e.g. methylene.

A further embodiment of the compounds according to the present invention relates to those compounds of formula I, in which
R6 is Ar1, in which
Ar1 is R61-substituted phenyl, in which
R61 is -T2-N(R611)R612, in which
T2 is a bond.

A further embodiment of the compounds according to the present invention relates to those compounds of formula I, in which
R6 is Ar1, in which
Ar1 is R61-substituted phenyl, in which
R61 is -T2-N(R611)R612, in which
T2 is 1-4C-alkylene, such as e.g. methylene.

A further embodiment of the compounds according to the present invention relates to those compounds of formula I, in which
R1, R2, R3, R4 and R5 are all hydrogen, and
R6 is Ar1, in which
Ar1 is any one selected from the group consisting of
3-methyl-phenyl, 4-methyl-phenyl,
3-dimethylamino-phenyl, 4-dimethylamino-phenyl,
3-aminomethyl-phenyl, 4-aminomethyl-phenyl,
3-(morpholin-4-yl-methyl)-phenyl, 4-(morpholin-4-yl-methyl)-phenyl,
3-(N-benzylamino-methyl)-phenyl, 3-(N-isobutylamino-methyl)-phenyl,
4-(N-benzylamino-methyl)-phenyl, 4-(N-Isobutylamino-methyl)-phenyl,
3-[N-(pyridinylmethyl)amino-methyl]-phenyl, 3-[N-(indolylmethyl)amino-methyl]-phenyl,
4-[N-(pyridinylmethyl)amino-methyl]-phenyl, 4-[N-(indolylmethyl)amino-methyl]-phenyl,
3-(N,N-dimethylamino-methyl)-phenyl, 4-(N,N-dimethylamino-methyl)-phenyl,
3-[N,N-(2-indolylethyl)-methyl-amino-methyl]-phenyl, 4-[N,N-(2-indolylethyl)-methyl-amino-methyl]-phenyl,
3-[N,N-(2-indolylethyl)-(2-hydroxyethyl)-amino-methyl]-phenyl, and 4-[N,N-(2-indolylethyl)-(2-hydroxyethyl)-amino-methyl]-phenyl.

A further embodiment of the compounds according to the present invention relates to those compounds of formula I, in which
R1, R2, R3, R4 and R5 are all hydrogen, and
R6 is Aa1, in which
Aa1 is a biphenyl radical.

A further embodiment of the compounds according to the present invention relates to those compounds of formula I, in which
R1, R2, R3, R4 and R5 are all hydrogen, and
R6 is Ha1, in which
Ha1 is a pyridinyl-thiophenyl radical.

A further embodiment of the compounds according to the present invention relates to those compounds of formula I, in which
R1, R2, R3, R4 and R5 are all hydrogen, and
R6 is Ah1, in which
Ah1 is a 3-(pyrazolyl)-phenyl, 4-(pyrazolyl)-phenyl, 4-(pyridinyl)-phenyl, or 3-(pyridinyl)-phenyl radical.

A further embodiment of the compounds according to the present invention relates to those compounds of formula I, in which R1, R2, R3, R4 and R5 are all hydrogen, and R7 is hydroxyl.

A further embodiment of the compounds according to the present invention relates to those compounds of formula I, in which R1, R2, R3, R4 and R5 are all hydrogen, and R7 is Cyc1.

A further embodiment of the compounds according to the present invention relates to those compounds of formula I, in which R1, R2, R3, R4 and R5 are all hydrogen, and R7 is 2-aminophenyl.

A further embodiment of the compounds according to the present invention relates to those compounds of formula I, in which R1, R2, R3, R4 and R5 are all hydrogen, and R7 is aminopyridyl.

A special embodiment of the compounds according to the present invention relates to those compounds of formula I, in which
R1, R2, R3, R4 and R5 are all hydrogen, and
R6 is Ar1, in which
Ar1 is any one selected from the group consisting of
3-methyl-phenyl, 4-methyl-phenyl,
3-dimethylamino-phenyl, 4-dimethylamino-phenyl,
3-aminomethyl-phenyl, 4-aminomethyl-phenyl,
3-(morpholin-4-yl-methyl)-phenyl, 4-(morpholin-4-yl-methyl)-phenyl,
3-(N-benzylamino-methyl)-phenyl, 3-(N-isobutylamino-methyl)-phenyl,
4-(N-benzylamino-methyl)-phenyl, 4-(N-isobutylamino-methyl)-phenyl,
3-[N-(pyridin-3-yl-methyl)amino-methyl]-phenyl, 3-[N-(pyridin-4-yl-methyl)amino-methyl]-phenyl,
3-[N-(indol-5-yl-methyl)amino-methyl]-phenyl, 3-[N-(indol-3-yl-methyl)amino-methyl]-phenyl,
4-[N-(pyridin-3-yl-methyl)amino-methyl]-phenyl, 4-[N-(pyridin-4-yl-methyl)amino-methyl]-phenyl,
4-[N-(indol-5-yl-methyl)amino-methyl]-phenyl, 4-[N-(indol-3-yl-methyl)amino-methyl]-phenyl,
3-(N,N-dimethylamino-methyl)-phenyl, 4-(N,N-dimethylamino-methyl)-phenyl,
3-{N,N-[2-(indol-2-yl)-ethyl]-methyl-amino-methyl}-phenyl, 4-{N,N-[2-(indol-2-yl)-ethyl]-methyl-amino-methyl}-phenyl,
3-{N,N-[2-(indol-2-yl)-ethyl]-(2-hydroxyethyl)-amino-methyl}-phenyl, and 4-{N,N-[2-(indol-2-yl)-ethyl]-(2-hydroxyethyl)-amino-methyl}-phenyl, and
R7 is hydroxyl,
and the salts thereof.

Another special embodiment of the compounds according to the present invention relates to those compounds of formula I, in which
R1, R2, R3, R4 and R5 are all hydrogen, and
R6 is Aa1, in which
Aa1 is 1,1'-biphen-4-yl or 1,1'-biphen-3-yl, and
R7 is hydroxyl,
and the salts thereof.

Another special embodiment of the compounds according to the present invention relates to those compounds of formula I, in which
R1, R2, R3, R4 and R5 are all hydrogen, and
R6 is Ha1, in which
Ha1 is 5-(pyridin-2-yl)-thiophen-2-yl, and
R7 is hydroxyl,
and the salts thereof.

Another special embodiment of the compounds according to the present invention relates to those compounds of formula I, in which
R1, R2, R3, R4 and R5 are all hydrogen, and
R6 is Ah1, in which
Ah1 is 3-(pyrazol-1-yl)-phenyl, 4-(pyrazol-1-yl)-phenyl, 4-(pyridin-4-yl)-phenyl, 3-(pyridin-4-yl)-phenyl, 4-(pyridin-3-yl)-phenyl, 3-(pyridin-3-yl)-phenyl, 3-(1H-pyrazol-4-yl)-phenyl or 4-(1H-pyrazol-4-yl)-phenyl,
R7 is hydroxyl,
and the salts thereof.

Another special embodiment of the compounds according to the present invention relates to those compounds of formula I, in which
R1, R2, R3, R4 and R5 are all hydrogen, and
R6 is Ar1, in which
Ar1 is any one selected from the group consisting of
3-methyl-phenyl, 4-methyl-phenyl,
3-dimethylamino-phenyl, 4-dimethylamino-phenyl,
3-aminomethyl-phenyl, 4-aminomethyl-phenyl,
3-(morpholin-4-yl-methyl)-phenyl, 4-(morpholin-4-yl-methyl)-phenyl,
3-(N-benzylamino-methyl)-phenyl, 3-(N-isobutylamino-methyl)-phenyl,
4-(N-benzylamino-methyl)-phenyl, 4-(N-isobutylamino-methyl)-phenyl,
3-[N-(pyridin-3-yl-methyl)amino-methyl]-phenyl, 3-[N-(pyridin-4-yl-methyl)amino-methyl]-phenyl,
3-[N-(indol-5-yl-methyl)amino-methyl]-phenyl, 3-[N-(indol-3-yl-methyl)amino-methyl]-phenyl,
4-[N-(pyridin-3-yl-methyl)amino-methyl]-phenyl, 4-[N-(pyridin-4-yl-methyl)amino-methyl]-phenyl,
4-[N-(indol-5-yl-methyl)amino-methyl]-phenyl, 4-[N-(indol-3-yl-methyl)amino-methyl]-phenyl,
3-(N,N-dimethylamino-methyl)-phenyl, 4-(N,N-dimethylamino-methyl)-phenyl,
3-{N,N-[2-(Indol-2-yl)-ethyl]-methyl-amino-methyl}-phenyl, 4-{N,N-[2-(indol-2-yl)-ethyl]-methyl-amino-methyl}-phenyl,
3-{N,N-[2-(indol-2-yl)-ethyl]-(2-hydroxyethyl)-amino-methyl}-phenyl, and 4-{N,N-[2-(indol-2-yl)-ethyl]-(2-hydroxyethyl)-amino-methyl}-phenyl, and
R7 is 2-aminophenyl,
and the salts thereof.

Another special embodiment of the compounds according to the present invention relates to those compounds of formula I, in which
R1, R2, R3, R4 and R5 are all hydrogen, and
R6 is Aa1, in which
Aa1 is 1,1'-biphen-4-yl or 1 µl'-biphen-3-yl, and
R7 is 2-aminophenyl,
and the salts thereof.

Another special embodiment of the compounds according to the present invention relates to those compounds of formula I, in which
R1, R2, R3, R4 and R5 are all hydrogen, and
R6 is Ha1, in which
Ha1 is 5-(pyridin-2-yl)-thiophen-2-yl, and
R7 is 2-aminophenyl,
and the salts thereof.

Another special embodiment of the compounds according to the present invention relates to those compounds of formula I, in which
R1, R2, R3, R4 and R5 are all hydrogen, and
R6 is Ah1, in which
Ah1 is 3-(pyrazol-1-yl)-phenyl, 4-(pyrazol-1-yl)-phenyl, 4-(pyridin-4-yl)-phenyl, 3-(pyridin-4-yl)-phenyl, 4 (pyridin-3-yl)-phenyl, 3-(pyridin-3-yl)-phenyl, 3-(1H-pyrazol-4-yl)-phenyl or 4-(1H-pyrazol-4-yl)-phenyl,
R7 is 2-aminophenyl,
and the salts thereof.

Exemplary compounds according to this invention may include any one selected from
1. (E)-N-Hydroxy-3-[1-(toluene-4-sulfonyl)-1-H-pyrrol-3-yl]-acrylamide
2. N-Hydroxy-3-(1-phenylmethanesulfonyl-1H-pyrrol-3-yl)-acrylamide
3. (E)-3-[1-(Biphenyl-4-sulfonyl)-1H-pyrrol-3-yl]-N-hydroxy-acrylamide
4. (E)-3-[1-(4-Dimethylamino-benzenesulfonyl)-1H-pyrrol-3-yl]-N-hydroxy-acrylamide
5. (E)-N-(2-Amino-phenyl)-3-[1-(toluene-4-sulfonyl)-1-pyrrol-3-yl]-acrylamide
6. (E)-N-(2-Amino-phenyl)-3-(1-phenylmethanesulfonyl-1H-pyrrol-3-yl)-acrylamide
7. (E)-N-(2-Amino-phenyl)-3-[1-(biphenyl-4-sulfonyl)-1-pyrrol-3-yl]-acrylamide
8. (E)-N-(2-Amino-phenyl)-3-[1-(4-dimethylamino-benzenesulfonyl)-1H-pyrrol-3-yl]-acrylamide
9. (E)-N-Hydroxy-3-(1-[4-(([2-(1H-indol-2-yl)-ethyl]-methyl-amino)-methyl)-benzene sulfonyl]-1H-pyrrol-3-yl)-acrylamide
10. (E)-3-[1-(4-Dimethylaminomethyl-benzenesulfonyl)-1H-pyrrol-3-yl]-N-hydroxy-acrylamide
11. (E)-N-Hydroxy-3-[1-(4-{[pyridin-3-ylmethyl)-amino]-methyl}-benzenesulfonyl)-1H-pyrrol-3-yl]-acrylamide
12. (E)-N-Hydroxy-3-[1-(4-{[(1H-indol-3-ylmethyl)-amino]-methyl}-benzenesulfonyl)-1H-pyrrol-3-yl]-acrylamide
13. (E)-3-{1-[4-(Benzylamino-methyl)-benzenesulfonyl]-1H-pyrrol-3-yl}-N-hydroxy-acrylamide
14. (E)-N-Hydroxy-3-{1-[4-(isobutylamino-methyl)-benzenesulfonyl]-1H-pyrrol-3-yl}-acrylamide,
15. (E)-N-Hydroxy-3-[1-(4-{[(1H-indol-5-ylmethyl)-amino]-methyl}-benzenesulfonyl)-1H-pyrrol-3-yl]-acrylamide
16. (E)-N-Hydroxy-3-[1-(4-{[(pyridin-4-ylmethyl)-amino]-methyl}-benzenesulfonyl)-1H-pyrrol-3-yl]-acrylamide
17. (E)-3-[1-(4-Aminomethyl-benzenesulfonyl)-1H-pyrrol-3-yl]-N-hydroxy-acrylamide
18. (E)-N-Hydroxy-3-[1-(4-pyridin-4-yl-benzenesulfonyl)-1H-pyrrol-3-yl]-acrylamide
19. (E)-N-Hydroxy-3-{1-[4-(1H-pyrazol-4-yl)-benzenesulfonyl]-1H-pyrrol-3-yl}-acrylamide
20. (E)-N-(2-Amino-phenyl)-3-[1-(4-pyridin-4-yl-benzenesulfonyl)-1H-pyrrol-3-yl]-acrylamide
21. (E)-N-(2-Amino-phenyl)-3-[1-(4-pyridin-3-yl-benzenesulfonyl)-1H-pyrrol-3-yl]-acrylamide
22. (E)-N-(2-Amino-phenyl)-3-{1-[4-(1H-pyrazol-4-yl)-benzenesulfonyl]-1H-pyrrol-3-yl}-acrylamide
23. (E)-3-[1-(Biphenyl-3-sulfonyl)-1H-pyrrol-3-yl]-N-hydroxy-acrylamide
24. (E)-N-Hydroxy-3-[1-(5-pyridin-2-yl-thiophene-2-sulfonyl)-1H-pyrrol-3-yl]-acrylamide
25. (E)-N-Hydroxy-3-[1-(4-pyrazol-1-yl-benzenesulfonyl)-1H-pyrrol-3-yl]-acrylamide
26. (E)-N-(2-Amino-phenyl)-3-[1-(5-pyridin-2-yl-thiophene-2-sulfonyl)-1H-pyrrol-3-yl]-acrylamide
27. (E)-N-Hydroxy-3-[1-(4-morpholin-4-ylmethyl-benzenesulfonyl)-1H-pyrrol-3-yl]-acrylamide
28. (E)-N-Hydroxy-3-{1-[4-({(2-hydroxy-ethyl)-[2-(1H-indol-2-yl)-ethyl]-amino}-methyl)-benzenesulfonyl]-1H-pyrrol-3-yl}-acrylamide
29. (E)-N-Hydroxy-3-[1-(3-pyridin-4-yl-benzenesulfonyl)-1H-pyrrol-3-yl]-acrylamide
30. (E)-N-(2-Amino-phenyl)-3-[1-(3-pyridin-4-yl-benzenesulfonyl)-1H-pyrrol-3-yl]-acrylamide
31. (E)-N-(2-Amino-phenyl)-3-[1-(3-pyridin-3-yl-benzenesulfonyl)-1H-pyrrol-3-yl]-acrylamide
32. (E)-N-Hydroxy-3-{1-[3-(1H-pyrazol-4-yl)-benzenesulfonyl]-1H-pyrrol-3-yl}-acrylamide and
33. (E)-N-(2-Amino-phenyl)-3-{1-(3-(1H-pyrazol-4-yl)-benzenesulfonyl)-1H-pyrrol-3-yl}-acrylamide,
and the salts thereof.

The compounds according to the present invention can be prepared, for example, as shown in the reaction schemes below and according to the reaction steps specified as follows, or, particularly, in a manner as described by way of example in the following examples, or analogously or similarly thereto using preparation procedures and synthesis strategies known to the person skilled in the art.

In reaction scheme 1 the carbon chain of compounds of formula V, in which R1, R2, R4 and R5 have the meanings mentioned above, is lengthened, for example, by a condensation reaction (with a malonic acid derivative) or by a Wittig or Julia reaction or, particularly in the case when R2 is hydrogen, by a Horner Wadsworth-Emmons reaction (with a 6-(alkoxycarbonyl)-phosphonic acid dialkyl ester) to obtain compounds of formula IV, in which R1, R2, R3, R4 and R5 have the meanings mentioned above and PG1 stands for a suitable temporary protective group for the carboxyl group, for example tert-butyl or one of those art-known protective groups mentioned in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

Reaction scheme 1

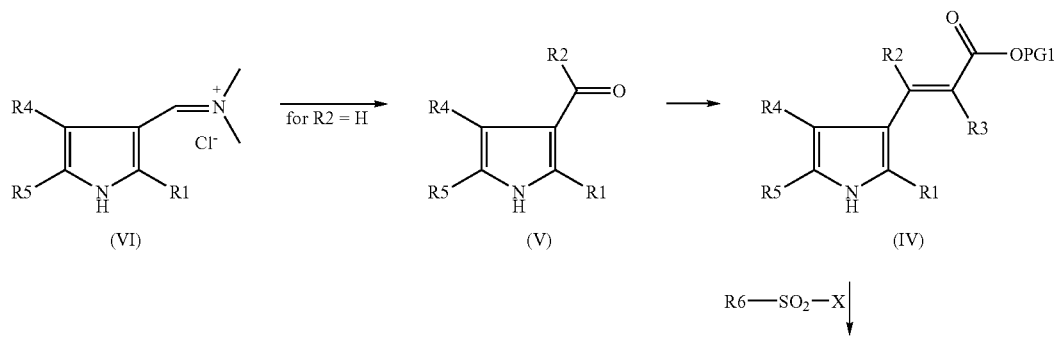

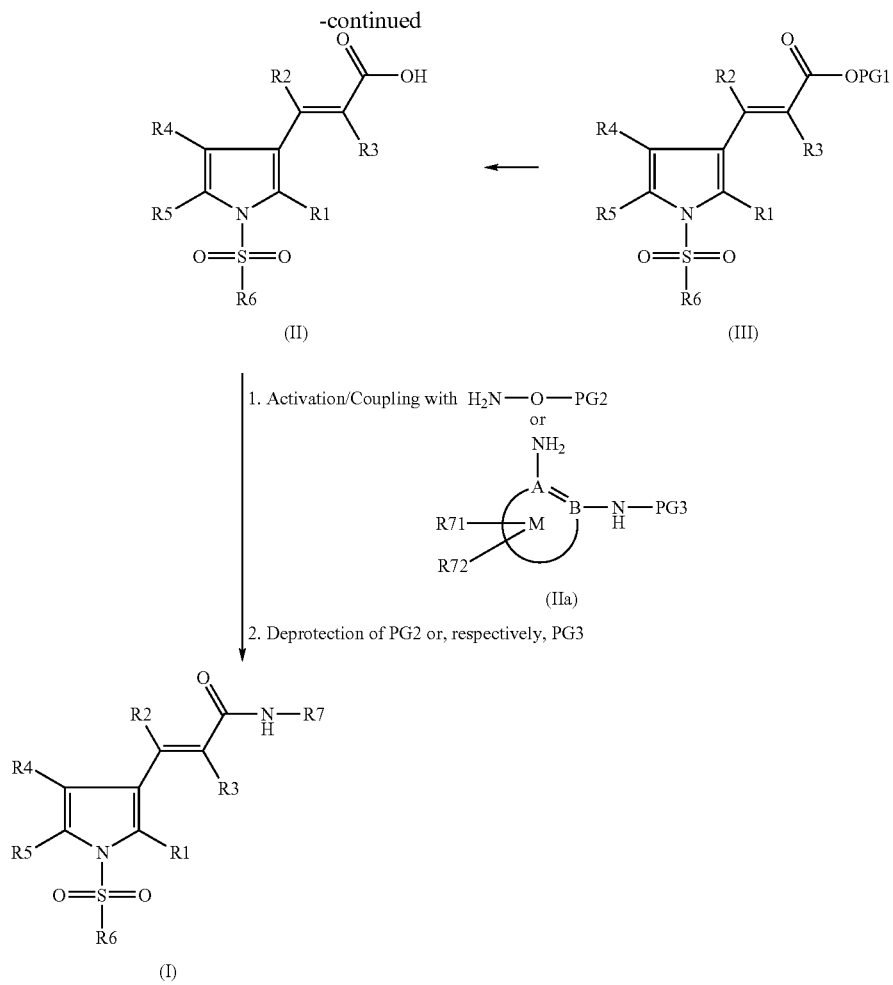

Compounds of formula V, in which R1, R2, R4 and R5 have the meanings mentioned above, are known, or can be prepared according to art-known procedures, or can be obtained as described in the following examples for the case that R2 is hydrogen from compounds of formula VI.

Compounds of formula VI are known or are accessible in a known manner or as described in the following examples.

Compounds of formula IV, in which R1, R2, R3, R4 and R5 have the meanings mentioned above and PG1 stands for a said suitable protective group, can be reacted with compounds of formula R6—SO$_2$—X, in which R6 has the meanings mentioned above and X is a suitable leaving group, such as e.g. chlorine, to give the corresponding compounds of formula III.

In the next reaction step, the protective group PG1 of compounds of formula III can be removed in a manner as described in the following examples or according to an art-known manner to afford compounds of formula II.

Compounds of formula R6-SO$_2$—X are known or can be prepared in a known manner.

Compounds of formula II, in which R1, R2, R3, R4, R5 and R6 have the meanings given above, can be coupled with compounds of formulae H$_2$N—O-PG2, in which PG2 is a suitable oxygen protective group such as e.g. a suitable silyl or tetrahydropyran-2-yl protective group, or IIa, in which PG3 stands for a suitable nitrogen protective group such as e.g. the tert-butyloxycarbonyl protective group, by reaction with amide bond linking reagents optionally in the presence of coupling additives known to the person skilled in the art.

Exemplary amide bond linking reagents known to the person skilled in the art which may be mentioned are, for example, carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N', N'-tetramethyluronium tetrafluoroborate or O-(benzotriazol-1yl)-N,N,N',,'-tetramethyl-uronium-hexafluorophosphate] and N,N'-carbonyldiimidazole.

Alternatively, compounds of formula II can be activated prior to the coupling reaction by forming an acid halide or acid anhydride optionally in an in-situ procedure without isolating the acid halide or acid anhydride.

Compounds of formulae H$_2$N—O-PG2 or IIa are known or can be prepared according to art-known processes.

Removal of the protective groups PG2 or PG3 can be obtained in a manner known for the person skilled in the art or as described in the following examples to give compounds of formula I, in which R1, R2, R3, R4, R5, R6 and R7 have the meanings mentioned above.

Compounds of formula I, in which T2 is 1-4C-alkylene, particularly methylene, can be prepared as outlined in the following reaction schemes 2 to 5, and specified below, or as described by way of example in the following examples, or analogously or similarly thereto.

As shown in reaction scheme 2 compounds of formula VII, in which T2 is 1-4C-alkylene, particularly methylene, and Y1 is a suitable leaving group, such as e.g. iodine, chlorine or, particularly, bromine, and PG4 stands for a suitable temporary protective group for the carboxyl group, for example tert-butyl, can be reacted with compounds of formula HN(R611)R612 to give in an art-known nucleophilic substitution reaction corresponding amino compounds, which are deprotected by removal of PG4 to give corresponding free acids of formula VIII, which can be coupled with compounds of formulae H₂N—O-PG2 or IIa as described above to give, after removal of PG2 and PG3, corresponding compounds of formula Ia.

Reaction scheme 2:

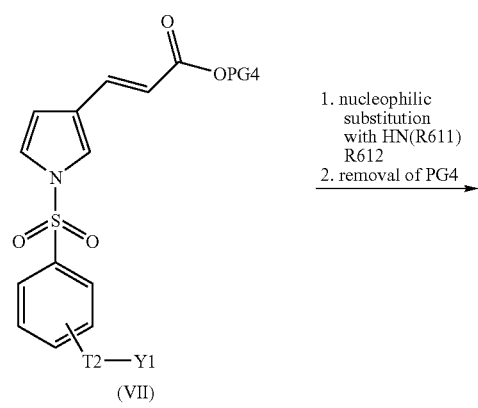

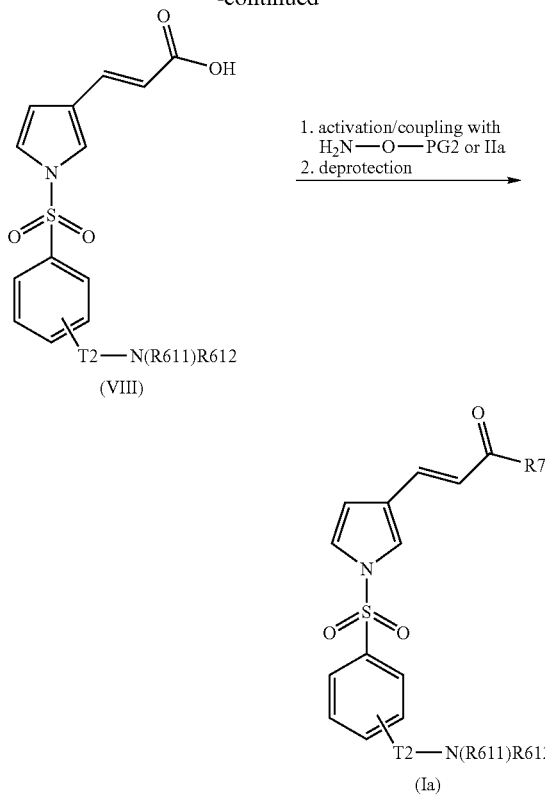

Alternatively, as shown in reaction scheme 3, compounds of formula VII, in which T2 is 1-4C-alkylene, particularly methylene, and Y1 is a suitable leaving group, such as e.g. iodine, chlorine or, particularly, bromine, and PG4 stands for a suitable temporary protective group for the carboxyl group, for example tert-butyl, can be reacted with a temporarily protected amine (a primary or, particularly, a secondary one), such as e.g. phthalimide, to give in an art-known nucleophilic substitution reaction corresponding amino compounds, which are deprotected by removal of PG4 to give corresponding free acids of formula IX, which can be coupled with compounds of formulae H₂N—O-PG2 or IIa as described above to give corresponding compounds of formula X.

Reaction scheme 3:

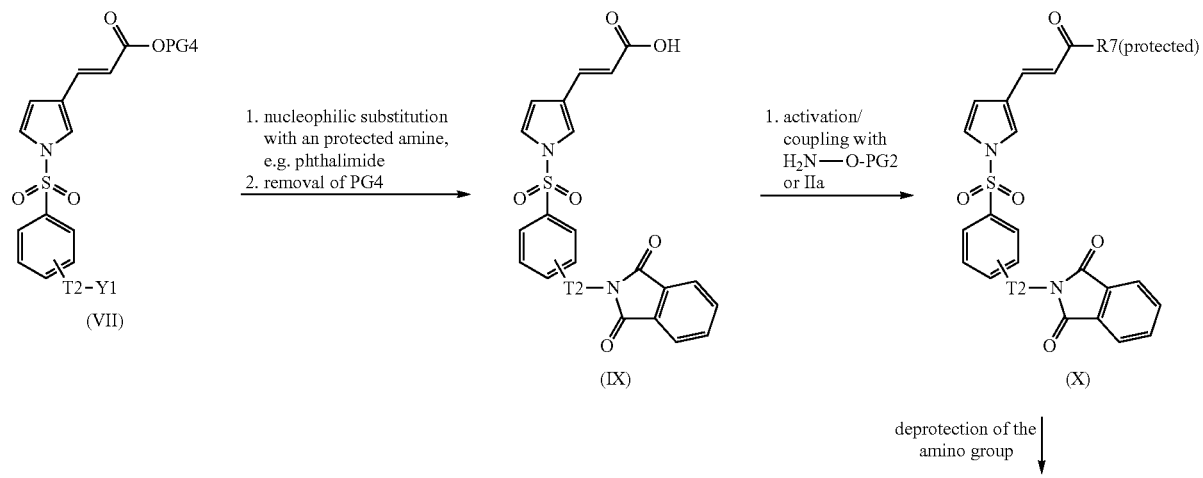

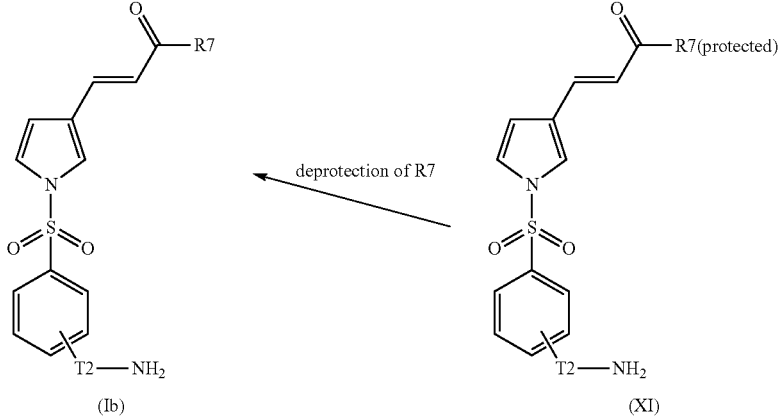

The amino moiety of compounds of formula X can be deprotected in an art-known manner to give corresponding compounds of formula XI, such as e.g. when the phthalimido protective group is used, this can be removed in a manner customary per se to the skilled person, e.g. with the aid of hydrazine.

Compounds of formula XI can be deprotected to give corresponding compounds of formula Ib.

Alternatively, as shown in reaction scheme 4, compounds of formula XI can be reacted with compounds of formula R611-Y1 and/or R612-Y2, in which R611 and 8612 have the meanings given above and are different from hydrogen and Y1 and Y2 are suitable leaving groups such as e.g. chlorine, bromine, iodine or a sultanate (e.g. triflate) leaving group, to give in an art-known nucleophilic substitution reaction corresponding compounds of formula XII or XII'.

Compounds of formula XII or XII' can be deprotected to give corresponding compounds of formula is or Id, respectively.

Reaction scheme 4:

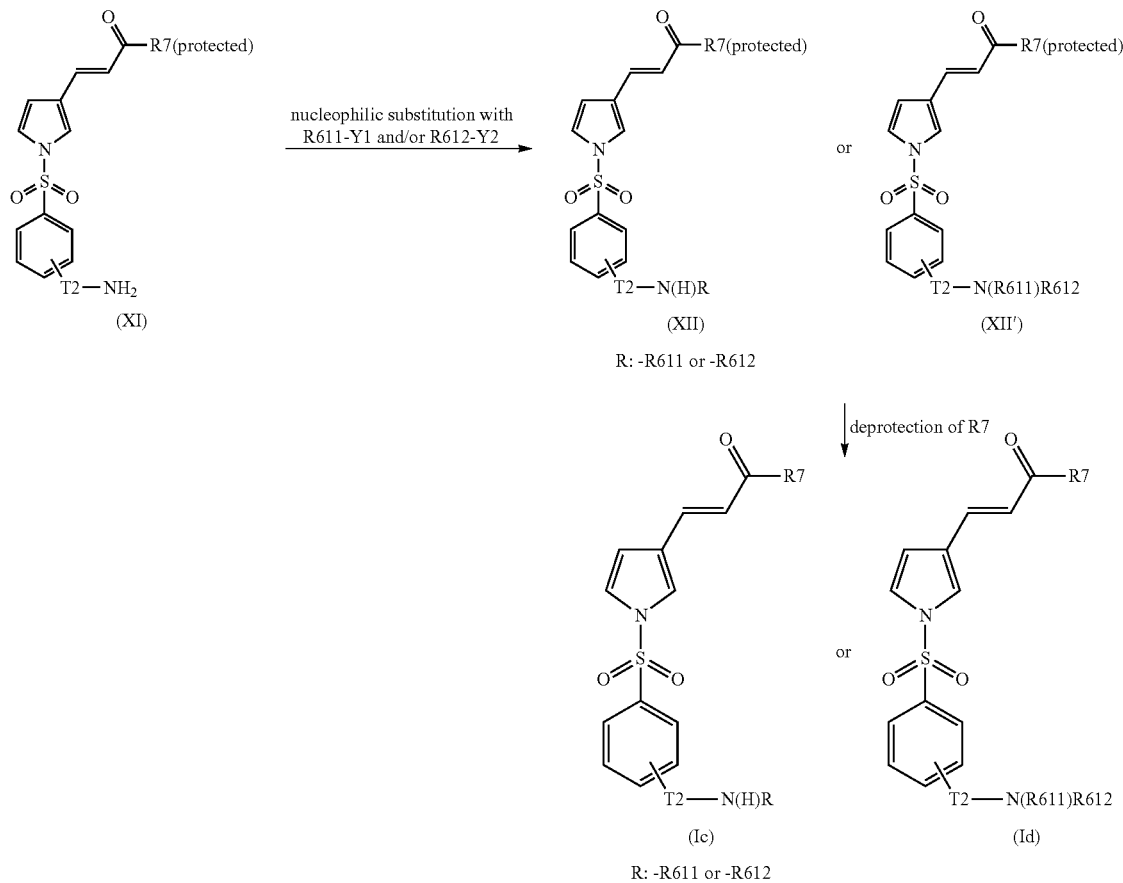

Yet alternatively, as shown in reaction scheme 5, compounds of formula XI can be reacted with aldehydes or ketones in an reductive amination reaction, such as e.g. compounds of formula XI can be reacted with benzaldehyde, or compounds of formulae 1-3C-alkyl-CHO or Har1 -CHO, in which Har1 has the meanings given above, to give in an art-known reductive amination reaction corresponding compounds of formula XIII.

Compounds of formula XIII can be deprotected to give corresponding compounds of formula Ie.

Reaction scheme 5:

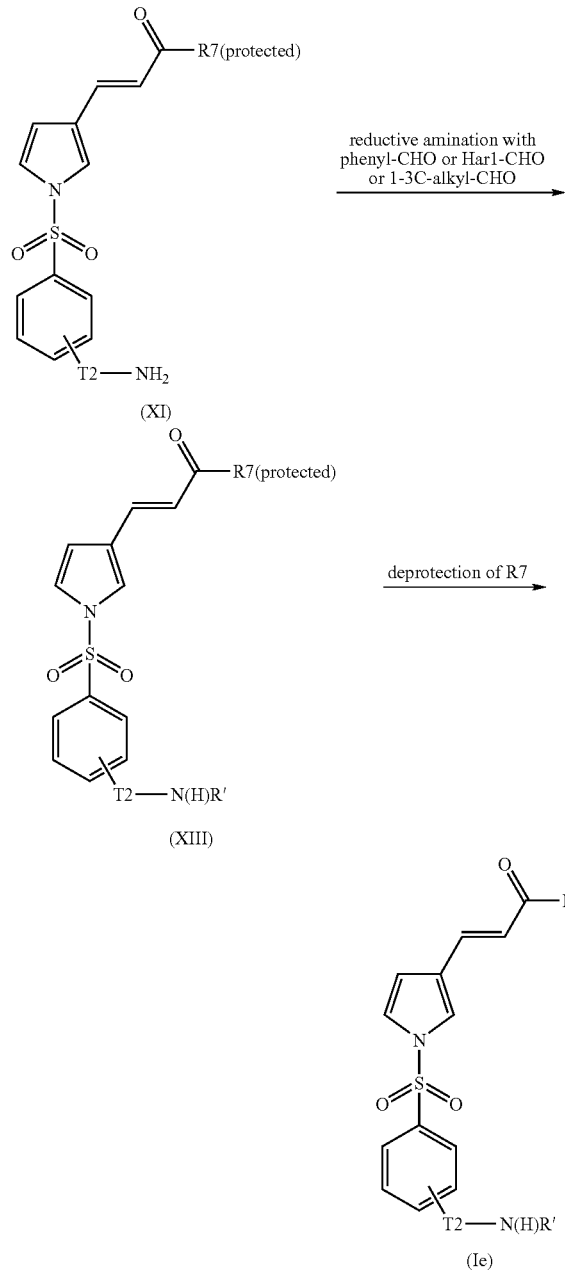

R': benzyl or —CH$_2$-Har1 or 1-4C-alkyl

Compounds of formula VII can be obtained according to the synthesis route shown in reaction scheme 1 and described above.

The abovementioned-compounds of formulae HN(R611)R612, R611-Y1, R612-Y2, 1-3C-alkyl-CHO or Har1-CHO are known or can be obtained according to art-known procedures.

Compounds of formula I, in which R6 is Aa1 or Ah1, can be prepared as outlined in the following reaction scheme 6, and specified below, or as described by way of example in the following examples, or analogously or similarly thereto.

Reaction scheme 6:

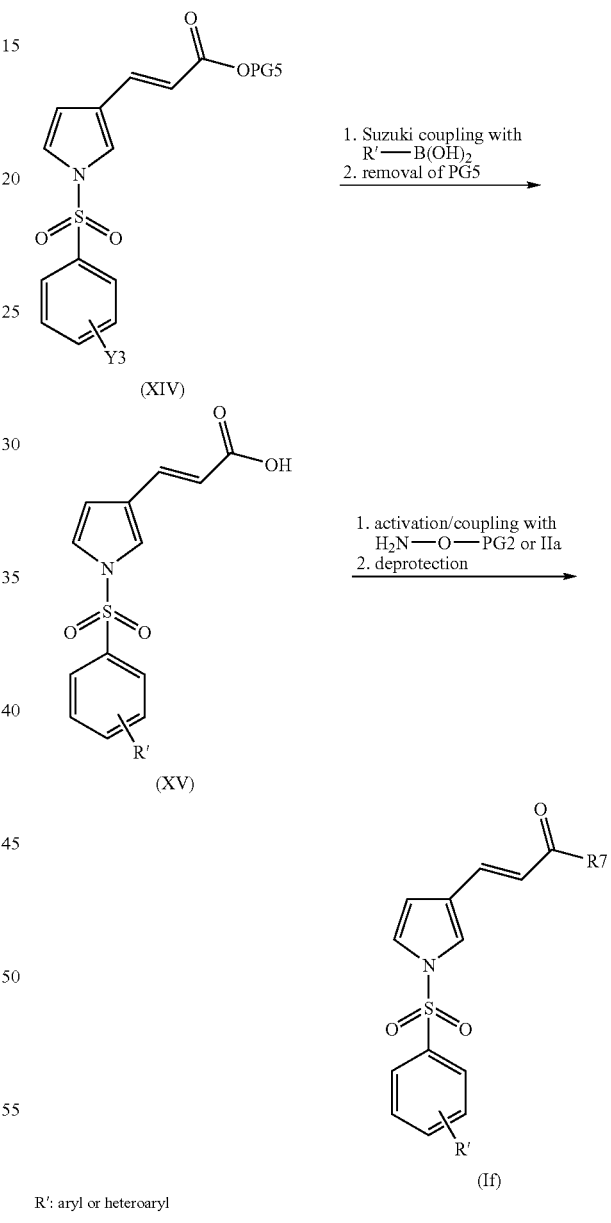

R': aryl or heteroaryl

As shown in reaction scheme 6 compounds of formula XIV, in which Y3 is a suitable leaving group, such as e.g. iodine or bromine, and PG5 stands for a suitable temporary protective group for the carboxyl group, for example tea-butyl, can be reacted with boronic acids of formula R'—B(OH)$_2$, in which R' is the terminal aryl or heteroaryl moiety of the abovementioned Aa1 or Ha1 radicals, or the boronic acid esters (e.g. the pinacol esters) thereof, to give in an art-known Suzuki reaction the corresponding CC-coupled compounds, which are deprotected by removal of PG5 to give corresponding free acids of formula XV, which can be coupled with compounds of formulae H₂N—O-PG2 or IIa as described above to give, after removal of PG2 and PG3, corresponding compounds of formula II.

Alternatively, as shown in reaction scheme 7 compounds of formula XIV, in which Y3 is a suitable leaving group, such as e.g. iodine or bromine, and PG5 stands for a suitable temporary protective group for the carboxyl group, for example tert-butyl, can be deprotected by removal of PG5, and the free carboxylic acid can be then coupled with compounds of formulae H₂N—O-PG2 or IIa as described above to give corresponding compounds of formula XVI. Compounds of formula XVI are reacted with boronic acids of formula R'—B(OH)₂, in which R' is the terminal aryl or heteroaryl moiety of the abovementioned Aa1 or Ha1 radicals, or the boronic acid esters (e.g. the pinacol esters) thereof, to give in an art-known Suzuki reaction the corresponding CC-coupled compounds, which are deprotected by removal of PG2 or PG3 to give corresponding compounds of formula If.

Reaction scheme 7:

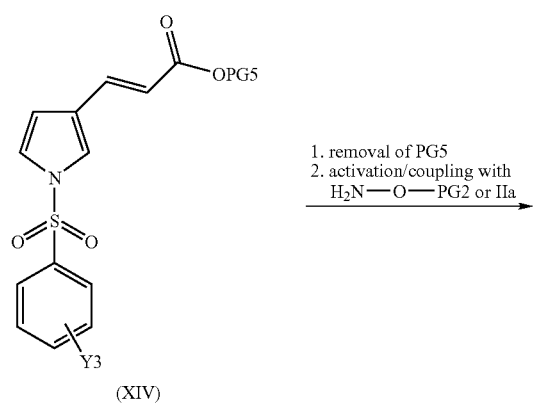

(XIV)

1. removal of PG5
2. activation/coupling with H₂N—O—PG2 or IIa

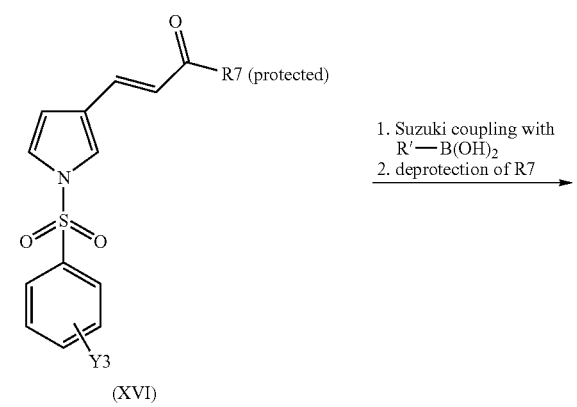

(XVI)

1. Suzuki coupling with R'—B(OH)₂
2. deprotection of R7

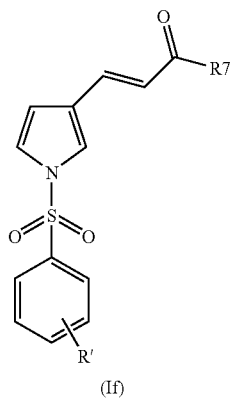

(If)

R': aryl or heteroaryl

The Suzuki reaction can be carried out in a manner habitual per se to the skilled person or as described in the following examples, or analogously or similarly thereto.

Compounds of formula XIV can be obtained according to the synthesis route shown in reaction scheme 1 and described above.

The abovementioned compounds of formula R'—B(OH)₂ are known or can be obtained according to art-known procedures.

The reactions mentioned above can be expediently carried out analogously to the methods known to the person skilled in the art or as described by way of example in the following examples.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The Isolation and purification of the substances according to the invention is carried out in a manner known per se, e.g. by distilling off the solvent in vacuo and recrystallizing the resulting residue from a suitable solvent or subjecting it to one of the customary purification methods, such as, for example, column chromatography on suitable support material.

Optionally, compounds of formula I can be converted into their salts, or, optionally, salts of the compounds of formula I can be converted into the free compounds.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of the formula I. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples serve to illustrate the invention further without restricting it. Likewise, further compounds of the formula I, whose preparation is not explicitly described, can be prepared in an analogous manner or in a manner familiar per se to the person skilled in the art using customary process techniques.

Any or all of the compounds which are mentioned as final products in the following examples as well as their salts are a preferred subject of the present invention.

in the examples, MS stands for mass spectrum, M for molecular ion, TSP for Thermospray Ionization, ESI for Electrospray ionization, EI for Electron Ionization, h for hours, min for minutes. Other abbreviations used herein have the meanings customary per se to the person skilled in the art.

EXAMPLES

Final Products

1. (E)-N-Hydroxy-3-[1-(toluene-4-sulfonyl)-1-H-pyrrol-3-yl]-acrylamide 0.231 g of (E)-3-[1-(toluene-4-sulfonyl)-1H-pyrrol-3yl]-acrylic acid (compound A1) are dissolved in 8 ml of dichloromethane at room temperature. Then 50 μl of N,N-dimethylformamide (DMF) are added, 0.275 g of oxalic acid chloride dissolved in 2 ml of dichloromethane are added dropwise and stirred for 1.5 hour. To the solution are added 0.439 g of O-(trimethylsilyl)hydroxylamine and stirred for 15 minutes. Then 20 ml of aqueous hydrochloric acid (1 M strength) are added and extracted with ethyl acetate. The combined organic phase is dried over sodium sulfate. Afterwards it is filtered and evaporated under vacuo. The crude product is purified by silica gel flash chromatography using a gradient of dichloromethane and methanol from 98:2 to 6:4 to yield 0.050 g of the title compound as a white solid.

MS (TSP): 307.0 (MH$^+$, 100%)
$^1$H-NMR (DMSO-d6): $^1$H-NMR (DMSO-d6): 2.37 (s, 3H); 6.12 (d, J=15.9 Hz, 1H); 6.54 (m, 1H); 7.25 (m, J=16.1 Hz, 2H); 7.42 (d, J=8.1 Hz, 2H); 7.79 (m, 1H); 7.85 (d, J=8.2 Hz, 2H); 8.96 (bs, exchangeable, 1H); 10.61 (bs, exchangeable, 1H)

2. N-Hydroxy-3-(1-phenylmethanesulfonyl-1H-pyrrol-3-yl)-acrylamide 0.189 g of (E)-3-(1-phenylmethanesulfonyl-1H-pyrrol-3-yl)-N-(tetrahydropyran-2-yloxy)-acrylamide (compound A2) are dissolved in 50 ml of a methanol/water (3/2) solution. Then 0.102 g of the acidic ion exchange resin amberlyst IR15 are added and the mixture is stirred for 91 hours at ambient temperature. The mixture is filtered. The filtrate is evaporated. The residue is crystallized from methanol to give 0.144 g of the title compound as white crystals.

MS (TSP): 307.0 (MH$^+$, 100%)
$^1$H-NMR (DMSO-d6): 5.00 (s, 2H); 6.11 (d, J=15.7 Hz, 1H); 6.50 (m, 1H); 6.96 (m, 1H); 7.11 (m, 2H); 7.32 (m, J=17 Hz, 5H); 8.90 (s, exchangeable, 1H); 10.60 (s, exchangeable, 1H)

3. (E)-3-[1-(Biphenyl-4-sulfonyl)-1H-pyrrol-3-yl]-N-hydroxy-acrylamide

The method used for preparation of this compound is analogous to the method described for compound 2. Starting materials: (E)-3-(1-(biphenyl-4-sulfonyl)-1H-pyrrol-3-yl)-N-(tetrahydro-pyran-2-yloxy)-acrylamide (compound A3) (0.150 g), methanol/water 3/2 (50 ml), amberlyst IR15 (0.300 g). Reaction conditions: room temperature, 34 hours.

Yield: 0.041 g, pale grey crystals
MS (ESI): 381.1 (MH$^+$—CH$_3$NO$_2$, 100%)
$^1$H-NMR (DMSO-d6): 6.14 (d, J=15.8 Hz, 1H); 6.58 (m, 1H); 7.31 (d, J=15.7 Hz, 1H); 7.43 (m, J=6.9 Hz, 4H); 7.70 (m, J=6.6 Hz, 3H); 7.91 (d, J=8.0 Hz, 2H); 8.02 (d, J=8.1 Hz, 2H); 8.92 (s, exchangeable, 1H); 10.60 (s, exchangeable, 1H)

4. (E)-3-[1-(4-Dimethylamino-benzenesulfonyl)-1H-pyrrol-3-yl]-N-hydroxy-acrylamide The method used for preparation of this compound is analogous to the method described for compound 2. Starting materials: (E)-3-[1-(4-dimethylamino-benzene sulfonyl)-1H-pyrrol-3-yl]-N-(tetrahydro-pyran-2-yloxy)-acrylamide (compound A4) (0200 g), methanol/water 3/2 (50 ml), amberlyst IR15 (0.402 g).

Reaction conditions: room temperature, 34 hours.
Yield: 0.098 g, pale red crystals
MS (ESI): 336.0 (MH$^+$, 100%)
$^1$H-NMR (DMSO-d6): 6.10 (m, J=16.5 Hz 1H); 6.49 (m, 1H); 6.75 (d, J=9.2 Hz, 2F-1); 7.24 (m, 2H); 7.64 (m, J$_1$=8.6 Hz, J$_2$=17.7 Hz, 3H); 8.89 (bs, exchangeable, 1H), 10.59 (bs, exchangeable, 1H)

5. (E)-N-(2-Amino-phenyl)-3-[1-(toluene-4-sulfonyl)-1H-pyrrol-3-yl]-acrylamide 0.116 g of (2-{(E)-3-[1-(toluene-4-sulfonyl)-1-H-pyrrol-3-yl]-allanoylamino}-phenyl)-carbamic acid tert-butyl ester (compound A5) are dissolved in 20 ml of dichloromethane at ambient temperature. 2 ml of trifluoroacetic acid (TFA) are added and the solution is stirred for 93 hour. The solvent is evaporated to dryness and to the residue are added 25 ml of water. The water phase is extracted exhaustively with ethyl acetate. Afterwards the combined organic phases are dried over sodium sulfate and filtered. The filtrate is evaporated under vacuo. Then the residue is crystallized from methanol to give 0.050 g of the title compound as white crystals.

MS (ESI): 382.0 (MH$^+$, 100%)
$^1$H-NMR (DMSO-d6): 2.38 (s, 3H); 4.48 (s, exchangeable, 2H); 6.55 (m, 3H); 6.71 (m, 1H); 6.90 (m, 1H); 7.40 (m, J=8.1 Hz, 5H); 7.70 (m, 1H); 7.89 (d, J=8.3 Hz, 2H); 9.20 (s, exchangeable, 1H)

6. (E)-N-(2-Amino-phenyl)-3-(1-phenylmethanesulfonyl-1H-pyrrol-3-yl)-acrylamide The method used for preparation of this compound is analogous to the method described for compound 5 with the exception that the product is purified by silica gel flash chromatography using a gradient of dichloromethane/methanol from 99:1 to 95:5.

Starting materials: {2-[(E)-3-[1-(phenylmethanesulfonyl-1-H-pyrrol-3-yl)-allanoylamino]-phenyl}-carbamic acid tert-butyl ester (compound A6) (0.146 g), CH$_2$Cl$_2$ (20 ml), TFA (2 ml). Reaction conditions: room temperature, 65 hours.

Yield: 0.037 g, white crystals
MS (ESI): 382.0 (MH$^+$)
$^1$H-NMR (DMSO-d6): 4.90 (s, 2H); 5.01 (s, exchangeable, 1H); 6.58 (m, J=5.7 Hz, 3H); 6.74 (m, J=6.7 Hz, 2H); 6.90 (m, 1H); 7.01 (m, 1H); 7.11 (m, J=5.6, 2H); 7.34 (m, J$_1$=5.7 Hz, J$_2$=6.7 Hz, 5H); 9.25 (s, exchangeable, 1H)

7. (E)-N-(2-Amino-phenyl)-3-[1-(biphenyl-4-sulfonyl)-1H-pyrrol-3-yl]-acrylamide The method used for preparation of this compound is analogous to the method described for compound 5. Starting materials: (2-{(E)-3-[1-(biphenyl-4-sulfonyl)-1H-pyrrol-3-yl]-allanoylamino}-phenyl)-carbamic acid tert-butyl ester (compound A7) (0.460 mmol), CH$_2$Cl$_2$ (50 ml), TFA (5 ml). Reaction conditions: room temperature, 18 hours.

Yield: 0.061 g, white crystals
MS (ESI): 444.0 (MH$^+$)
$^1$H-NMR (DMSO-d6): 4.90 (bs, exchangeable, 2H); 6.58 (m, J$_1$=51.4 Hz, J$_2$=7.5 Hz, 3H); 6.71 (m, J$_1$=1.4 Hz, J$_2$=6.6 Hz, 1H); 6.90 (m, J$_1$=1.4 Hz, J$_2$=6.6 Hz, 1H); 7.40 (m, J$_1$=7.5 Hz, J$_2$=7.7 Hz, 6H); 7.78 (m, J=7.7 Hz, 3H); 7.95 (d, J=8.6 Hz, 2H); 8.08 (d, J=8.8 Hz, 2H); 9.23 (s, exchangeable, 1H)

8. (E)-N-(2-Amino-phenyl)-3-[1-(4-dimethylamino-benzenesulfonyl)-1H-pyrrol-3-yl]-acrylamide The method used for preparation of this compound is analogous to the method described for compound 5 with the exception that the product is purified by crystallization from ethyl acetate.

Starting materials: (2-[(E)-3-[1-(4-dimethylamino-benzenesulfonyl)-1H-pyrrol-3-yl]-allanoylamino]-phenyl)-carbamic acid tert-butyl ester (compound A8) (0.141 g), CH$_2$Cl$_2$ (10 ml), TFA (1 ml). Reaction conditions: room temperature, 20 hours.

Yield: 0.109 g, pale red crystals
MS (ESI): 411.0 (MH$^+$, 100%)
$^1$H-NMR (DMSO-d6): 3.00 (s, 6H); 3.97 (s, exchangeable, 2H); 6.79 (m, J=15.4 Hz, 2H); 6.79 (d, J=9.2 Hz, 2H); 7.04 (m, J$_1$=2.7 Hz, J$_2$=8.7 Hz, J$_3$=15.5 Hz, 3H); 7.40 (m, J$_1$=15.6 Hz, J$_2$=8.6 Hz, 3H) 7.70 (m, J$_1$=2.9 Hz, J$_2$=9.2 Hz, 3H) 9.74 (s, exchangeable, 1H)

9. (E)-N-Hydroxy-3-(1-[4-(([2-(1H-indol-2-yl)-ethyl]-methyl-amino)-methyl)-benzene sulfonyl]-1H-pyrrol-3-yl)-acrylamide 81 mg of (E)-3-(1-[4-(([2-(1H-indol-2-yl)-ethyl]-methyl-amino)-benzenesulfonyl]-1H-pyrrol-3-yl)-N-(tetrahydropyran-2-yloxy)-acrylamide (compound A9) are dissolved in 5 ml of methanol. After addition of 15 ml of 0.1 N hydrochloric acid the mixture is stirred for 21 hour. Then the reaction mixture is evaporated. The residue is washed with ethyl acetate and dried under vacuum at −50° C.

Yield: 55 mg, pale yellow solid

10. (E)-3-[1-(4-Dimethylaminomethyl-benzenesulfonyl)-1H-pyrrol-3-yl]-N-hydroxy-acrylamide The method used for to preparation of this compound is analogous to the method described for compound 9.

Starting material: (E)-3-[1-(4-Dimethylaminomethyl-benzenesulfonyl)-1H-pyrrol-3-yl]-N-tetrahydro-pyran-2-yloxy)-acrylamide (compound A10)

11. (E)-N-Hydroxy-3-[1-(4-{[(pyridin-3-ylmethyl)-amino]-methyl}-benzenesulfonyl)-1H-pyrrol-3-yl]-acrylamide Starting from compound A11, the method which can be used for the preparation is analogous to the method described for compound 9. The crude product is pure enough for biological testing.
MH+=413.0

12. (E)-N-Hydroxy-3-[1-(4-{[(1H-indol-3-ylmethyl)-amino]-methyl}-benzenesulfonyl)-1H-pyrrol-3-yl]-acrylamide Starting from compound A12, the method which can be used for the preparation is analogous to the method described for compound 9. The crude product is pure enough for biological testing.
MH+=449.0

13. (E)-3-{1-[4-(Benzylamino-methyl)-benzenesulfonyl]-1H-pyrrol-3-yl}-N-hydroxy-acrylamide Starting from compound A13, the method which can be used for the preparation is analogous to the method described for compound a
MH+=412.1

14. (E)-N-Hydroxy-3-{1-[4-(isobutylamino-methyl)-benzenesulfonyl]-1H-pyrrol-3-yl}-acrylamide Starting from compound A14, the method which can be used for the preparation is analogous to the method described for compound 9.
MH+=378.1

15. (E)-N-Hydroxy-3-[1-(4-{[1H-indol-5-ylmethyl)-amino]-methyl}-benzenesulfonyl)-1H-pyrrol-3-yl]-acrylamide Starting from compound A15, the method which can be used for the preparation is analogous to the method described for compound 9.
MH$^+$=449.1

16. (E)-N-Hydroxy-3-[1-(4-{[(pyridin-4-ylmethyl)-amino]-methyl}-benzenesulfonyl)-1H-pyrrol-3-yl]-acrylamide Starting from compound A16, the method which can be used for the preparation is analogous to the method described for compound 9.
MH+=413.1

17. (E)-3-[1-(4-Aminomethyl-benzenesulfonyl)-1H-pyrrol-3-yl]-N-hydroxy-acrylamide Starting from compound 136, the method which can be used for the preparation is analogous to the method described for compound 9. The crude product is purified by washing with methanol. A solid is obtained in 69% yield.
Melting point: 227.0-228.6° C.

18. (E)-N-Hydroxy-3-[1-(4-pyridin-4-yl-benzene-sulfonyl)-1H-pyrrol-3-yl]acrylamide Starting from compound A17, the method which can be used for the preparation is analogous to the method described for compound 9. The reaction mixture is partly evaporated and the resulting suspension is filtered. The product is isolated as colorless solid.
Melting point: 219.3-221.4° C.

19. (E)-N-Hydroxy-3-{1-[4-(1H-pyrazol-4-yl)-benzenesulfonyl]-1H-pyrrol-3-yl}-acrylamide Starting from compound A18, the method which can be used for the preparation is analogous to the method described for compound 9.
Melting point: 203.8-211.9° C.

20. (E)-N-(2-Amino-phenyl)-3-[1-(4-pyridin-4-yl-benzenesulfonyl)-1H-pyrrol-3-yl]-acrylamide Starting from compound A19, the method which can be used for the preparation is analogous to the method described for compound 21.
Melting point: 244.2-246.5° C.

21. (E)-N-(2-Amino-phenyl)-3-[1-(4-pyridin-3-yl-benzenesulfonyl)-1H-pyrrol-3-yl]-acrylamide The compound is prepared by treatment of (2-{(E)-3-[1-(4-pyridin-3-yl-benzenesulfonyl)-1H-pyrrol-3-yl]-allanoylamino}-phenyl)-carbamic acid tert-butyl ester (compound A20) in dioxane with HCl. After the reaction is finished, the product precipitates from the reaction mixture.
Melting point: 199.7-202.3° C.

22. (E)-N-(2-Amino-phenyl)-3-{1-[4-(1H-pyrazol-4-yl)-benzenesulfonyl]-1H-pyrrol-3-yl}-acrylamide Starting from compound A21, the method which can be used for the preparation is analogous to the method described for compound 21.
Melting point: 232.3-240.9° C.

23. (E)-3-[1-(Biphenyl-3-sulfonyl)-1H-pyrrol-3-yl]-N-hydroxy-acrylamide

Starting from compound A22, the method which can be used for the preparation is analogous to the method described for compound 9.
Melting point: 114-159.4° C. Sinter at 83° C.

24. (E)-N-Hydroxy-3-[1-(5-pyridin-2-yl-thiophene-2-sulfonyl)-1H-pyrrol-3-yl]-acrylamide Starting from compound A23, the method which can be used for the preparation is analogous to the method described for compound 9. The product crystallizes from the reaction mixture.
Melting point: 181.3-182° C.

25. (E)-N-Hydroxy-3-[1-(4-pyrazol-1-yl-benzene-sulfonyl)-1H-pyrrol-3-yl]-acrylamide Starting from compound A24, the method which can be used for the preparation is analogous to the method described for compound 9. The crude product is purified by washing with dichloromethane.
Melting point: 160.7-166.6° C.

26. (E)-N-(2-Amino-phenyl)-3-[1-(5-pyridin-2-yl-thiophene-2-sulfonyl)-1H-pyrrol-3-yl]-acrylamide Starting from compound A25, the method which can be used for the preparation is analogous to the method described for compound 21. The product is purified by washing the crude product with ethyl acetate.
Melting point: 1713-174.7° C.

27. (E)-N-Hydroxy-3-[1-(4-morpholin-4-ylmethyl-benzenesulfonyl)-1H-pyrrol-3-yl]-acrylamide Starting from compound A26, the method which can be used for the preparation is analogous to the method described for compound 9. The title compound is isolated by freeze-drying methods.
Melting point: 168-170° C.

28. (E)-N-Hydroxy-3-{1-[4-({(2-hydroxy-ethyl)-[2-(1H-indol-2-yl)-ethyl]-amino}-methyl)-benzene-sulfonyl]-1H-pyrrol-3-yl}-acrylamide Starting from compound A 27, the method which can be used for the preparation is analogous to the method described for compound 9. The reaction mixture is evaporated and the title compound is isolated as an oil.
MH+509.1

Starting from compound D6, the following compounds may be prepared via synthesis routes which are analogous to the synthesis routes resulting to the Examples 18 to 22.

29. (E)-N-Hydroxy-3-[1-(3-pyridin-4-yl-benzene-sulfonyl)-1H-pyrrol-3-yl]-acrylamide 30. (E)-N-(2-Amino-phenyl)-3-[1-(3-pyridin-4-yl-bertzenesultonyl)-1H-pyrrol-3-yl]-acryiamide 31. (E)-N-(2-Amino-phenyl)-3-O-(3-pyridin-3-O-benzenesulfonyl)-1H-pyrrol-3-yikacrylamide 32. (E)-N-Hydroxy-3-{1-[3-(1H-pyrazol-4-yl)-benzenesulfonyl]-1H-pyrrol-3-yl}-acrylamide 33. (E)-N-(2-Amino-phenyl)-3-{1-[3-(1H-pyrazol-4-yl)-benzenesulfonyl]-1H-pyrrol-3-yl}-acrylamide Starting Materials A1 (E)-3-[1-(Toluene-4-sulfonyl)-1H-pyrrol-3yl]-acrylic acid 1.60 g of (E)-3-[1-(toluene-4-sulfonyl)-1H-pyrrol-3yl]-acrylic acid tert-butyl ester (compound C1) are dissolved in 70 ml of dichloromethane at ambient temperature. Then 7 ml of trifluoroacetic acid (TFA) are added and stirred for 4 hours. The solvent is evaporated to dryness and to the residue are added 30 ml of water. The water phase is extracted exhaustively with ethyl acetate. Then the organic phase is dried over sodium sulfate. The filtrate is evaporated and dried under vacuo to give 0.951 g of the title compound as a pale grey solid.
MS (TSP): 290.0 (M-H+, 100%)

¹H-NMR (DMSO-d6): 2.36 (s, 3H); 6.20 (d, J=15.9 Hz, 1H); 6.74 (m, J=3.1 Hz, 1H); 7.41 (m, J₁=3.1 Hz, J₂=8.2 Hz, J₃=16.1 Hz, 4H); 7.78 (m, 1H), 7.87 (d, J=8.4 Hz, 2H); 11.80 (bs, exchangeable, 1H)

A2 (E)-3-(9-Phenylmethanesulfonyl-1H-pyrrol-3-yl)-N-(tetrahydropyran-2-yloxy)-acrylamide 0.295 g of (E)-3-(1-phenylmethanesulfonyl-1H-pyrrol-3-yl)-acrylic acid (compound B1), 0.152 g of N-hydroxybenzotriazole hydrate (HOBt?H₂O) and 561 µl of triethylamine are dissolved in 20 ml of N,N-dimethylformamide (DMF) at room temperature. Afterwards it is added 0.601 g of N-(3-dimethylaminopropyl)-N'-ethylcarbodiimide hydrochloride (EDO?HCl) and stirred for 1 hour at room temperature. Then is added 0.152 g of O-(tetrahydro-2H-pyran-2-yl)-hydroxylamine and stirred for 2 hour. The DMF is evaporated under high vacuo. Water is added and the mixture was extracted with ethyl acetate. The organic phase is dried over sodium sulfate. Then it is filtered and evaporated under vacuo. The crude product is purified by silica gel flash chromatography using a gradient of dichloromethane/methanol from 99:1 to 98:2 to give 0.189 g of the title compound as a pale grey solid.

MS (ESI): 390.9 (MH⁺, 100%)

¹H-NMR (DMSO-d6): 1.60 (m, OH); 3.51 (m, 1H); 3.91 (m, 1H); 4.89 (m, 1H); 5.00 (s, 2H); 6.18 (d, J=15.3 Hz, 1H); 6.50 (s, 1H); 6.96 (m, J=6.2 Hz, 1H); 7.10 (m, J₁=7.3 Hz, J₂=7.9 Hz, 2H); 7.30 (m,₁=5.1 Hz, J₂=7.3 Hz, J₃=8.1 Hz, J₄=8.1 Hz, J₅=16.2 Hz, 5H); 10.60 (s, exchangeable, 1H); 11.08 (bs, exchangeable, 1H)

A3 (E)-3-(1-(Biphenyl-4-sulfonyl)-1H-pyrrol-3-yl)-N-(tetrahydro-pyran-2-yloxy)-acrylamide The method used for preparation of this compound is analogous to the method described for compound A2 with the exception that the product is purified by crystallization from water and methanol. Starting materials: (E)-3-[1-(biphenyl-4-sulfonyl)-1H-pyrrol-3-yl]-acrylic acid (compound 62) (0.300 g), HOBt?H₂O (0.130 g), triethylamine (668 µl), DMF (20 ml), EDC?HCl (0.508 g), O-(tetrahydro-2H-pyran-yl) hydroxylamine (0.089 g). Reaction conditions: room temperature, 1 hour; room temperature, 18 hours.

Yield: 0.345 g, pale grey solid

MS (ESI): 452.8 (MH⁺); 369.0 (MH⁺—C₅H₉O, 100%)

¹H-NMR (DMSO-d6): 1.61 (m, 6); 3.50 (m, 1H); 3.92 (m, 1H); 4.87 (m, 1H); 6.21 (d, J=14.7 Hz, 1H); 6.60 (s, 1H); 7.48 (m, J=6.9 Hz, 5H); 7.72 (m, J₁=7.0 Hz, J₂=14.7 Hz, 3H); 7.98 (d, J=8.5 Hz, 2H); 8.06 (d, J=8.6 Hz, 2H); 11.06 (bs, exchangeable, 1H)

A4 (E)-3-[1-(4-Dimethylamino-benzenesulfonyl)-1H-pyrrol-3-yl]-N-(tetrahydro-pyran-2-yloxy)-acrylamide The method used for preparation of this compound is analogous to the method described for compound A2 with the exception that the product is purified by silica gel flash chromatography using a gradient of dichloromethane and methanol from 99:1 to 98:2.

Starting materials: (E)-3-[1-(4-dimethylamino-benzenesulfonyl)-1H-pyrrol-3-yl]-acrylic acid (compound B3) (0.150 g), HOBt?H₂O (0.072 g), triethylamine (259 µl), DMF (10 ml), EDC?HCl (0.269 g), O-(tetrahydro-2H-pyran-2-yl) hydroxylamine (0.049 g). Reaction conditions: room temperature, 1 hour; room temperature, 17 hours.

Yield: 0.187 g, pale red solid

MS (ESI): 419.2 (MH⁺); 336.0 (MH⁺—C₅H₉O, 100%)

¹H-NMR (DMSO-d6): 1.61 (m, 6); 3.02 (s, 6H); 3.50 (m, 1H); 3.92 (m, 1H); 4.85 (m, 1H); 6.19 (m, 1H); 6.50 (m, 1H); 6.75 (m, J=9.2 Hz, 2H); 7.31 (m, 2H); 7.64 (m, J=9.2 Hz, 3H); 11.01 (bs, exchangeable, 1H)

A5 (2-{(E)-3-[1-(Toluene-4-sulfonyl)-1-H-pyrrol-3-yl]allanoylamino}-phenyl)-carbamic acid tert-butyl ester The method used for preparation of this compound is analogous to the method described for compound A2 with the exception that the product is purified by silica gel flash chromatography using a gradient of dichloromethane and methanol from 99:1 to 98:1.

Starting materials: (E)-3-[1-(toluene-4-sulfonyl)-1H-pyrrol-3yl]-acrylic acid (compound A1) (0.400 g), HOBt?H₂O (0.285 g), triethylamine (652 µl), DMF (25 ml), EDC?HCl (0.698 g), N—BOC-1,2,-phenylenediamine (0.286 g). Reaction conditions: room temperature, 1 hour; room temperature, 2 hours.

Yield: 0.609 g, pale grey solid

MS (ESI): 481.7 (MH⁺, 100%)

¹H-NMR (DMSO-d6): 1.40 (m, 9H); 2.39 (s, 3H); 6.61 (m, J₁=1.7 Hz, J₂=2.2 Hz, J₃=5.0 Hz, 2H); 7.09 (m, J₁=1.8 Hz, J₂=2.3 Hz, 2H); 7.37 (m, J₁=2.0 Hz, J₂=5.0 Hz, J₃=8.0 Hz, 4H); 7.64 (m, 1H); 7.88 (d, J=8.4 Hz, 2H); 8.41 (s, exchangeable, 1H); 9.57 (s, exchangeable, 1H)

A6 {2-[(E)-3-[1-(Phenylmethanesulfonyl-1-H-pyrrol-3-yl)-allanoylamino]-phenyl}-carbamic acid tert-butyl ester The method used for preparation of this compound is analogous to the method described for compound A2 with the exception that the product is purified by silica gel flash chromatography using a gradient of dichloromethane and methanol from 99:1 to 95:5.

Starting materials: (E)-3-(1-phenylmethanesulfonyl-1H-pyrrol-3-yl)-acrylic acid (compound B1) (0.180 g), HOBt?H₂O (0.090 g), triethylamine (295 µl), DMF (10 ml), EDC?HCl (0.315 g), N—BOC-1,2,-phenylenediamine (0.081.g). Reaction conditions: room temperature, 1 hour; room temperature, 17 hours.

Yield: 0.218 g, pale grey solid

MS (ESI): 504.0 (MNa⁺, 100%); 481.8 (MH⁺)

¹H-NMR (DMSO-d6): 1.42 (m, 9H); 5.04 (s, 2H); 6.56 (m, J₁=2.2 Hz, J₂=10.2 Hz, 2H); 7.14 (m, J₁=2.2 Hz, J₂=5.5 Hz, J₃=10.1 Hz, 4H); 7.36 (m, J₁=5.5 Hz, J₂=7.2 Hz, 4H); 7.52 (m, J₁=2.2 Hz, J₂=7.2 Hz, 2H); 8.49 (s, exchangeable, 1H); 9.67 (s, exchangeable, 1H)

A7 (2-{(E)-3-1-(Biphenyl-4-sulfonyl)-1H-pyrrol-3-yl]-allanoylamino}-phenyl)-carbamic acid tert-butyl ester The method used for preparation of this compound is analogous to the method described for compound A2 with the exception that the product is purified by silica gel flash chromatography using a gradient of toluene/ethyl acetate from 99:1 to 9:1.

Starting materials: (E)-3-[1-(biphenyl-4-sulfonyl)-1H-pyrrol-3-yl)-acrylic acid (compound B2) (0.300 g), HOBt?H₂O (0.130 g), triethylamine (668 µl), DMF (20 ml), EDC?HCl (0.508 g), N—BOC-1,2,-phenylenediamine (0.176 g). Reaction conditions: room temperature, 1 hour; room temperature, 17 hours.

Yield: 0.285 g, pale grey solid

MS (ESI): 543.8 (MH$^+$); 487.9 (MH$^+$—C$_4$H$_8$); 336.1 (MH$^+$—C$_{11}$H$_{14}$N$_2$O$_2$, 100%)

$^1$H-NMR (DMSO-d6): 1.47 (m, 9H); 6.50 (m, J=5.4 Hz, 1H); 6.64 (m, J=7.7 Hz, 2H); 7.10 (m, J$_1$=5.4 Hz, J$_2$=7.7 Hz, 3H); 7.51 (m, J$_1$=J$_2$=J$_3$=3.6 Hz, 5H); 7.73 (m, 2H); 7.81 (m, 1H); 7.96 (d, J=8.6 Hz, 2H); 8.08 (d, J=8.6 Hz, 2H); 8.41 (s, exchangeable, 1H); 8.59 (s, exchangeable, 1H)

A8 (2-{(E)-3-[1-(4-Dimethylamino-benzenesulfonyl)-1H-pyrrol-3-yl]-allanoylamino}-phenyl)-carbamic acid tent butyl ester The method used for preparation of this compound is analogous to the method described for compound A2 with the exception that the product is purified by crystallization from ethyl acetate.

Starting materials: (E)-3-[1-(4-dimethylamino-benzenesulfonyl)-1H-pyrrol-3-yl)-acrylic acid (compound B3) (0.150 g), HOBt?H$_2$O (0.072 g), triethylamine (259 μl), DMF (10 ml), EDC?HCl (0.269 g), N—BOC-1,2-phenylenediamine (0.049 g). Reaction conditions: room temperature, 1 hour; room temperature, 21 hours.

Yield: 0.142 g, pale red solid

MS (ESI): 510.9 (MH$^+$, 100%)

$^1$H-NMR (DMSO-d6): 1.42 (m, 9H); 3.00 (s, 6H); 6.51 (m, 2H) 6.79 (d, J=9.2 Hz, 2H); 7.09 (m, J=5.5 Hz, 2H); 7.36 (m, 2H); 7.50 (m, J=5.5 Hz, 2H); 7.70 (m, J=9.2 Hz, 2H); 8.41 (s, exchangeable, 1H); 9.55 (s, exchangeable, 1H)

A9 (E)-3-(1-[4-(([2-(1H-indol-2-yl)-ethyl]-methyl-amino)-benzenesulfonyl]-1H-pyrrol-3-yl)-N-(tetrahydropyran-2-yloxy)-acrylamide 825 mg of (E)-3-(1-[4-(([2-(1H-indol-2-yl)-ethyl]-methyl-amino)-benzenesulfonyl]-1H-pyrrol-3-yl)-acrylic acid (compound B4), 165 mg of HOBt?H$_2$O and 1.24 ml of triethylamine are dissolved in 70 ml of DMF at room temperature. Afterwards it is added 726 mg of EDC?HCl and stirred for 1 hour. Then 140 mg of O-(tetrahydro-2H-pyran-2-yl)-hydroxylamine are added and stirred for 18 hour. The DMF is evaporated under high vacuum. Then water is added to the residue and extracted with ethyl acetate. The organic phase is dried over sodium sulfate and evaporated under vacuum. Then the mixture is evaporated and the crude product is purified by silica gel flash chromatography using a gradient of dichloromethane and methanol 98:2-9:1.

Yield: 289 mg, pale red solid

A10 (E)-3-[1-(4-Dimethylaminomethyl-benzenesulfonyl)-1H-pyrrol-3yl]-N-tetrahydro-pyran-2-yloxy)-acrylamide The method used for to preparation of the title compound is analogous to the method described for compound A9.

Starting materials: (E)-3-[1-(4-Dimethylaminomethyl-benzenesulfonyl)-1H-pyrrol-yl]-acrylic acid (compound B5) (1.78 g), HOBt?H$_2$O (366 mg), triethylamine (2.1 ml), DMF (80 ml), EDO?HCl (1.54 g), 0-(tetrahydro-2H-pyran-2-yl)-hydroxylamine (306 mg). Reaction condition: room temperature, 1 hour; room temperature, 48 hours.

Yield: 836 mg, pale yellow solid

A11 (E)-3-[1-(4-{[(Pyridin-3-ylmethyl)-amino]-methyl}-benzenesulfonyl)-1H-pyrrol-3-yl]-N-(tetrahydro-pyran-2-yloxy)-acrylamide A mixture of compound B6, sodium triacetoxyborohydride, methanol and 3-pyridinecarboxaldehyde is stirred at ambient temperature overnight. The reaction mixture is evaporated and partitioned between dichloromethane and water. The crude product is purified by silica gel flash chromatography. A nearly colorless oil is obtained.

Starting from compound B6 and the appropriate aldehyde the following compounds A12 to A16 can be obtained according to compound A11.

A12 (E)-3-[1-(4-{[(1H-indol-3-ylmethyl)-amino]-methyl}-benzenesulfonyl)-1H-pyrrol-3-yl]-N-(tetrahydro-pyran-2-yloxy)-acrylamide

A13 (E)-3-{1-[4-(Benzylamino-methyl)-benzenesulfonyl]-1H-pyrrol-3-yl}-N-(tetrahydro-pyran-2-yloxy)-acrylamide

A14 (E)-3-{1-[4-(Isobutylamino-methyl)-benzenesulfonyl]-1H-pyrrol-3-yl}-N-(tetrahydro-pyran-2-yloxy)-acrylamide

A15 (E)-3-[1-(4-{[(1H-Indol-5-ylmethyl)-amino]-methyl}-benzenesulfonyl)-1H-pyrrol-3-yl]-N-(tetrahydro-pyran-2-yloxy)-acrylamide

A16 (E)-3-[1-(4-{[(Pyridin-4-ylmethyl)-amino]-methyl}-benzenesulfonyl)-1H-pyrrol-3-yl]-N-(tetrahydro-pyran-2-yloxy)-acrylamide

A17 (E)-3-[1-(4-Pyridin-4-ylphenylsulfonyl)-1H-pyrrol-3-yl]-N-(tetrahydropyran-2-yloxy)-acrylamide Starting from compound B7 the title compound can be obtained according to compound A2.

A18 (E)-3-{1-(4-(1H-Pyrazol-4-yl)-phenylsulfonyl]-1H-pyrrol-3-yl}-N-(tetrahydropyran-2-yloxy)-acrylamide Starting from compound B8 the title compound can be obtained according to compound A2.

A19 [2-((E)-3-{1-[4-Pyridin-4-yl-benzenesulfonyl]-1H-pyrrol-3-yl}-allanoylamino)-phenyl]-carbamic acid tert-butyl ester Starting from compound B7 the title compound can be obtained according to compound A5.

A20 [2-((E)-3-{1-[4-Pyridin-3-yl-benzenesulfonyl]-1H-pyrrol-3-yl}-allanoylamino)-phenyl]carbamic acid tert-butyl ester Starting from compound B9 the title compound can be obtained according to compound A5.

A21 [2-((E)-3-{1-[4-(1H-Pyrazol-4-yl)-benzene-sulfonyl]-1H-pyrrol-3-yl}-allanoylamino)-phenyl]-carbamic acid tert-butyl ester Starting from compound B8 the title compound can be obtained according to compound A5.

A22 (E)-3-(1-(Biphenyl-3-sulfonyl)-1H-pyrrol-3-yl)-N-(tetrahydro-pyran-2-yloxy)-acrylamide Starting from compound B10 the title compound can be obtained according to compound A2.

A23 (E)-3-(1-(5-Pyridin-2-yl-thiophene-2-sulfonyl)-1H-pyrrol-3-yl)-N-(tetrahydro-pyran-2-yloxy)-acrylamide Starting from compound B11 the title compound can be obtained according to compound A2.

A24 (E)-3-(1-(4-Pyrazol-1-yl-benzenesulfonyl)-1H-pyrrol-3-yl)-N-(tetrahydro-pyran-2-yloxy)-acrylamide Starting from compound B12 the title compound can be obtained according to compound A2.

A25 (2-{(E)-3-[1-(5-Pyridin-2-yl-thiophene-2-yl-sulfonyl)-1H-pyrrol-3-yl]-allanoylamino}-phenyl)-carbamic acid tert-butyl ester Starting from compound B11 the title compound can be obtained according to compound A5.

A26 (E)-3-{1-[4-(Morpholin-4-yl-methyl)benzene-sulfonyl]-1H-pyrrol-3yl}-N-tetrahydro-pyran-2-yloxy)-acrylamide Starting from compound 1313 the title compound can be obtained according to compound A2.

A27 (E)-3-{1-[4-({[2-hydroxy-ethyl]-[2-(1H-indol-3-yl)-ethyl]-amino}-methyl)-benzenesulfonyl]-1H-pyrrol-3-yl}-N-(tetrahydro-pyran-2-yloxy)-acrylamide (E)-3-{1-[4-({[2-(tert-Butyl-dimethyl-silanyloxy)-ethyl]-[2-(1H-indol-3-yl)-ethyl]-amino}-methyl)-benzenesulfonyl]-1H-pyrrol-3-yl}-N-(tetrahydro-pyran-2-yloxy)-acrylamide (compound B 14) (120 mg, 0.169 mmol) is dissolved in THF (20 ml). Then it is added tetrabutylammonium fluoride (203 µl, 0.203, 1M in THF) and triethylamine (47 µl, 0.338 mmol) and the mixture is stirred for 17 hours. After addition of water (50 ml) and extraction with ethyl acetate the organic phase is dried over sodium sulfate, filtrated and evaporated. The crude product is purified by a silica gel flash chromatography using dichloromethane-methanol eluent.

B1 (E)-3-(1-Phenylmethanesulfonyl-1H-pyrrol-3-yl)-acrylic acid

The method used for preparation of this compound is analogous to the method described for compound A1 with the exception that the product is isolated by crystallization from a mixture of aceton (29.7 g), water (10.8 g) and HCl ($C_{(HCl)}$=1 mol/l, 5.3 g).

Starting materials: (E)-3-(1-phenylmethanesulfonyl-1H-pyrrol-3-yl)-acrylic acid tert-butylester (compound C2) (1.45 g), $CH_2Cl_2$ (80 ml), TFA (8 ml). Reaction conditions: room temperature, 2 hours.

Yield: 0.660 g, pale grey crystals
MS (TSP): 289.9 (M-H$^+$, 100%)
$^1$H-NMR (DMSO-d6): 5.00 (s, 2H); 6.21 (d, J=15.9 Hz, 1H); 6.72 (m, $J_1$=1.1.9 Hz, $J_2$=3.4 Hz, 1H); 7.01 (m, J=5.3, 1H); 7.10 (m, J=1.6 Hz, 2H); 7.31 (m, 7.41 (m, $J_1$=1.6 Hz, $J_2$. 1.9 Hz, $J_3$=3.4 Hz, $J_4$=5.3 Hz, $J_5$=16.1 Hz, 4H)

B2 (E)-3-[1-(Biphenyl-4-sulfonyl)-1H-pyrrol-3-yl]-acrylic acid

The method used for preparation of this compound is analogous to the method described for compound A1.

Starting materials: (E)-3-[1-(biphenyl-4-sulfonyl)-1H-pyrrol-3-yl)-acrylic acid tert-butyl ester (compound C3) (1.05 g), $CH_2Cl_2$ (100 ml), TFA (10 ml). Reaction conditions: room temperature, 21 hours.

Yield: 0.710 g, pale yellow solid
MS (ESI): 728.7 (2MNa$^+$, 100%); 354.1 (MH$^+$)
$^1$H-NMR (DMSO-d6): 6.29 (d, J=16.0 Hz, 1H); 6.81 (m, $J_1$=1.2 Hz, $J_2$=1.8 Hz, $J_3$=3.0 Hz, 1H); 7.49 (m, $J_1$=3 Hz, $J_2$=7.7 Hz, $J_0$=16.0 Hz, 5H); 7.75 (m, $J_1$=1.3 Hz, $J_2$=1.8 Hz, $J_3$=7.7 Hz, 2H); 7.85 (s, 1H); 7.95 (d, J=8.6 Hz, 2H); 8.09 (d, J=8.6 Hz, 2H); 12.17 (bs, exchangeable, 1H)

B3 (E)-3-[1-(4-Dimethylamino-benzensulfonyl)-1H-pyrrol-3-yl)-acrylic acid

The method used for preparation of this compound is analogous to the method described for compound A1.

Starting materials: (E)-3-[1-(4-dimethylamino-benzensulfonyl)-1H-pyrrol-3-yl)-acrylic acid tert-butyl ester (compound C4) (0.801 g), $CH_2Cl_2$ (100 ml), TFA (10 ml). Reaction conditions: room temperature, 16 hours.

Yield: 0.550 g, pale red solid
MS (ESI): 662.7 (2MNa$^+$, 100%); 321.0 (MH$^+$)
$^1$H-NMR (DMSO-d6): 2.98 (s, 6H); 6.16 (d, J=15.8 Hz, 1H); 6.68 (m, J=3.2 Hz, 1H); 6.75 (m, J=92 Hz, 2H); 7.29 (m, J=2.9 Hz, 1H); 7.43 (d, J=15.9 Hz, 1H); 7.70 (m, J=9.1 Hz, 3H); 12.11 (bs, exchangeable, 1H)

B4 (E)-3-(1-[4-(([2-(1H-indol-2-yl)-ethyl]methyl-amino)-benzenesulfonyl]-1H-pyrrol-3-yl)-acrylic acid 1.01 g of (E)-3-(1-[4-(([2-(1H-indol-2-yl)-ethyl]-methyl-amino)-benzenesulfonyl]-1H-pyrrol-3-yl)-acrylic acid tert-butyl ester (compound C5) are dissolved in 100 ml of dichloromethane and stirred for 5 minutes. It is added 10 ml of TFA and the mixture stirred for 19 hour. The solution is evaporated under vacuum. Then is added toluene to the residue (small amount to purify the TFA salt) and evaporated under vacuum.

Yield: 1.32 g, Pale brown solid

B5 (E)-3-[1-(4-Dimethylaminomethyl-benzenesulfonyl)-1H-pyrrol-yl]-acrylic acid The method used for to preparation of this compound is analogous to the method described for compound 84.

Starting materials: (E)-3-[1-(4-Dimethylaminomethyl-benzenesulfonyl)-1H-pyrrol-yl]-acrylic acid tert-butyl ester (compound C6) (2.13 g), TFA (10 ml); 24 hour.

Yield: 3.21 g (with 3 TFA salt), pale brown solid

B6 (E)-3-[1-(4-Aminomethyl-benzenesulfonyl)-1H-pyrrol-3-yl]-N-(tetrahydro-pyran-2-yloxy)-acrylamide To a mixture of 1 g of compound C7 and 50 ml ethanol is added 0.57 ml hydrazine hydrate (80%). The mixture is refluxed for 2.5 h. Afterwards, the reaction mixture is cooled to ambient temperature and the resulting white suspension is filtered. The product in the filtrate is purified by silica gel flash chromatography.

B7 (E)-3-[1-(4-Pyridin-4-ylphenylsulfonyl)-1H-pyrrol-3-yl]-acrylic acid

Starting from compound C8 the title compound can be obtained according to compound A1.

B8 (E)-3-{1-[4-(1H-Pyrazol-4-yl)-phenylsulfonyl]-1H-pyrrol-3-yl}-acrylic acid Starting from compound C9 the title compound can be obtained according to compound A1.

B9 (E)-3-[1-(4-Pyridin-3-ylphenylsulfonyl)-1H-pyrrol-3-yl]-acrylic acid

Starting from compound C10 the title compound can be obtained according to compound A1.

B10 (E)-3-(1-(Biphenyl-3-sulfonyl)-1H-pyrrol-3-yl)-acrylic acid

Starting from compound C11 the title compound can be obtained according to compound A1.

B11 (E)-3-(1-(5-Pyridin-2-yl-thiophene-2-sulfonyl)-1H-pyrrol-3-yl)-acrylic acid Starting from compound C12 the title compound can be obtained according to compound A1.

B12 (E)-3-(1-(4-Pyrazol-1-yl-benzenesulfonyl)-1H-pyrrol-3-yl)-acrylic acid

Starting from compound C13 the title compound can be obtained according to compound A1.

B13 (E)-3-{1-[4-(Morpholin-4-yl-methyl)-benzenesulfonyl]-1H-pyrrol-3yl}-acrylic acid Starting from compound C14 the title compound can be obtained according to compound A1.

B14 (E)-3-{1-[4-({[2-(tert-Butyl-dimethyl-silanyloxy)-ethyl]-[2-(1H-indol-3-yl)-ethyl]-amino}-methyl)-benzenesulfonyl]-1H-pyrrol-3-yl}-N-(tetrahydro-pyran-2-yloxy)-acrylamide (E)-3-{1-[4-({[2-(tert-Butyl-dimethyl-silanyloxy)-ethyl]-(2-(1H-indol-3-yl)-ethyl]-amino}-methyl)-benzenesulfonyl]-1H-pyrrol-3-yl}-acrylic acid (compound C15) (1.15 g, 1.16 mmol), HOBtH$_2$O (171 mg, 1.16 mmol) and triethylamine (2 ml) is dissolved in DMF (100 ml) at room temperature. After addition of EDCl.HCl (786 mg, 3.48 mmol) the mixture is stirred for 1.5 hours. Then it is added O-(tetrahydro-2H-pyran-2-yl)-hydroxylamine (136 mg, 1.16 mmol) and stirred for 17 hours. After evaporation and addition of 200 ml water the mixture is extracted with ethyl acetate. The organic phase is dried over sodium sulfate. Then it is filtrated and evaporated. The crude product is purified by a silica gel flash chromatography using dichloromethane-methanol eluent.

C1 (E)-3-[1-(Toluene-4-sulfonyl)-1H-pyrrol-3yl]-acrylic acid tert-butyl ester 0.230 g of sodium hydride (60%) is suspended in 6 ml of tetrahydrofurane under nitrogen at −30° C. 1.01 g of (E)-3-(1H-pyrrol-3-yl)acrylic acid tert-butyl ester (compound D1) are added to the suspension and warmed slowly to room temperature and stirred for 30 minutes. Afterwards it is recooled to −30° C. and 1.19 g of p-toluenesulfonylchloride are added and stirred for 2.5 hours. The suspension is warmed slowly at room temperature and 40 ml of saturated aqueous sodium chloride solution are added. The mixture is extracted with ethyl acetate. The combined organic phase is dried over sodium sulfate (Na$_2$SO$_4$). Afterwards it is filtered and evaporated under vacuo. The crude product is purified by silica gel flash chromatography using a gradient of hexane-ethyl acetate from 9:1 to 1:1 to give 1.60 g of the title compound as a pale yellow solid.

MS (ESI): 347.6 (MH$^+$); 291.9 (MH$^+$—C$_4$H$_2$, 100%)

$^1$H-NMR (DMSO-d6): 1.43 (s, 9H); 2.37 (s, 3H); 6.21 (d, J=15.9 Hz, 1H); 6.74 (m, J=3.1 Hz, 1H); 7.40 (m, J$_1$=15.9 Hz, J$_2$=12.7 Hz, J$_3$=3.2 Hz, 4H); 7.82 (m, J=12.6 Hz, 3H)

C2 (E)-3-(1-Phenylmethansulfonyl-1H-pyrrol-3-yl)-acrylic acid tert-butylester The method used for preparation of this compound is analogous to the method described for compound C1 with the exception that the product is purified by silica gel flash chromatography using gradient of hexane/ethyl acetate from 8:1 to 5:1.

Starting materials: sodium hydride 60% (0.240 g), (E)-3-(1H-pyrrol-3-yl)-acrylic acid tert-butyl ester (compound D1) (1.01 g), α-toluenesulfonylchloride (1.19 g). Reaction conditions: −30° C., 30 min; 30° C., 2.5 hours.

Yield: 1.45 g, pale yellow solid

MS (TSP): 346.3 (M-H$^+$, 100%)

$^1$H-NMR (DMSO-d6): 1.47 (s, 9H); 5.00 (s, 2H); 6.21 (d, J=15.8 Hz, 1H); 6.72 (m, J$_1$=1.8 Hz, J$_2$=3.3 Hz, 1H); 6.98 (m, J=5.3, 1H); 7.09 (m, J$_1$=2.1 Hz, J$_2$=7.8 Hz, 2H); 7.31 (m, J$_1$=1.9 Hz, J$_2$=3.5 Hz, J$_3$=5.4 Hz, J$_4$=7.7 Hz, J$_5$=15.7 Hz, 5H)

C3 (E)-3-[1-(Biphenyl-4-sulfonyl)-1H-pyrrol-3-yl]-acrylic acid tert-butyl ester The method used for preparation of this compound is analogous to the method described for compound C1 with the exception that the product is purified by silica gel flash chromatography using a gradient of petroleum ether/diethylether from 7:1 to 1:1.

Starting materials: sodium hydride 60% (0.207 g), (E)-3-(1H-pyrrol-3-yl)-acrylic acid tert-butyl ester (compound D1) (0.531 g), 4-biphenylsulphonylchloride (0.834 g). Reaction conditions: −30° C., 10 min; 30° C., 30 min.

Yield: 1.05 g, pale yellow solid

MS (ESI): 354.0 (MH$^+$—C$_4$H$_9$, 100%)

$^1$H-NMR (DMSO-d6): 1.45 (s, 9H); 6.26 (d, J=15.9 Hz, 1H); 6.80 (m, J=1.7 Hz, 1H); 7.47 (m, J=15.7 Hz, 5H); 7.72 (m, J=1.8 Hz, 2H); 7.87 (m, 1H); 7.92 (d, J=8.7 Hz, 2H); 8.09 (d, J=8.6 Hz, 2H)

C4 (E)-3-[1-(4-Dimethylamino-benzensulfonyl)-1H-pyrrol-3-yl]-acrylic acid ten-butyl ester The method used for preparation of this compound is analogous to the method described for compound C1 with the exception that the product is purified by silica gel flash chromatography using a gradient of petroleum ether/diethylether from 7:1 to 1:1.

Starting materials: sodium hydride 60% (0.031 g), (E)-3-(1H-pyrrol-3-yl)-acrylic acid tert-butyl ester (compound D1) (0.100 g), 4-dimethylamino-benzenesulfonyl chloride (0.145 g). Reaction conditions: 30° C., 45 min; −30° C., 2.5 hours.

Yield: 0.160 g, pale red solid

MS (ESI): 376.8 (MH$^+$); 321.0 (MH$^+$—C$_4$H$_9$, 100%)

$^1$H-NMR (DMSO-d6): 1.42 (s, 9H); 3.00 (s, 6H); 6.19 (d, J=15.8 Hz, 1H); 6.72 (m, J=9.2 Hz, 3H); 7.25 (m, 1H); 7.37 (d, J=15.8 Hz, 1H); 7.69 (m, J=9.1 Hz, 3H)

C5 (E)-3-(1-[4-(([2-(1H-indol-2-yl)-ethyl]-methyl-amino)-benzenesulfonyl]-1H-pyrrol-3-yl)-acrylic acid tert-butyl ester 1.50 g of (E)-3-[1-(4-bromomethyl-benzenesulfonyl)-1H-pyrrol-3-yl]-acrylic acid tert-butyl ester (compound D2) are dissolved in 70 ml of ethanol at room temperature. After addition of 0.486 ml of triethylamine and 696 mg of omega-methyltryptamine it is stirred for 21 hour. Then the solution is evaporated under vacuum. The crude product is purified by silica gel flash chromatography using a gradient of hexane and ethyl acetate from 5:1-2:1.

Yield: 1.08 g, pale yellow solid

C6 (E)-3-[1-(4-Dimethylaminomethyl-benzenesulfonyl)-1H-pyrrol-yl]-acrylic acid tert-butyl ester The method used for to preparation of this compound is analogous to the method described for compound C5 with the exception that the product was crystallized in ethanol.

Starting materials: (E)-3-[1-(4-Bromomethyl-benzenesulfonyl)-1H-pyrrol-3-yl]-acrylic acid tert-butyl ester (compound D$_2$) (3.94 g), ethanol (150 ml), dimethylamine (1.89 g)

Yield: 2.19 g, pale yellow solid

C7 (E)-3-{1-[4-(1,3-Dioxo-1,3-dihydro-isoindol-2-ylmethyl)-benzenesulfonyl]-1H-pyrrol-3-yl}-acrylic acid Starting from compound D3 the method which can be used for this preparation is analogous to the method described for the compound B4. The title compound is purified by washing with toluene.

Starting from (E)-3-[1-(4-bromo-benzenesulfonyl)-1H-pyrrol-3-yl]-acrylic acid tert-butyl ester (compound D4) and the appropriate boronic acid derivative the following compounds C8 and C9 can be obtained according to compound C10.

C8 (E)-3-[1-(4-Pyridin-4-ylphenylsulfonyl)-1H-pyrrol-3-yl]-acrylic acid tert-butyl ester

C9 (E)-3-{1-[4-(1H-Pyrazol-4-yl)-phenylsulfonyl]-1H-pyrrol-3-yl}-acrylic acid tert-butyl ester

C10 (E)-3-[1-(4-Pyridin-3-ylphenylsulfonyl)-1H-pyrrol-3-yl]-acrylic acid tert-butyl ester 0.18 g (E)-3-[1-(4-bromo-benzenesulfonyl)-1H-pyrrol-3-yl]-acrylic acid tart-butyl ester (compound D4) and 62 mg 3-pyridylboronic acid are dissolved in 10 ml DME. A catalytic amount of bis-(triphenylphosphin-palladium (II)-chloride and 0.6 ml of an aqueous solution of sodium carbonate are added and the mixture is heated to reflux temperature overnight. The title compound is isolated by means of chromatography.

C11 (E)-3-[1-(Biphenyl-3-sulfonyl)-1H-pyrrol-3-yl]-acrylic acid tert-butyl ester Starting from (E)-3-(1H-pyrrol-3-yl)-acrylic acid tert-butyl ester (compound D1) and art-known 3-biphenylsulphonylchloride the title compound can be obtained analogously or similarly as described for compound C1.

C12 (E)-3-[1-(5-Pyridin-2-yl-thiophene-2-sulfonyl)-1H-pyrrol-3-yl]-acrylic acid tert-butyl ester Starting from (E)-3-(1H-pyrrol-3-yl)-acrylic acid tent-butyl ester (compound D1) and art-known 5-pyridin-2-yl-thiophene-2-sulfonylchloride the title compound can be obtained analogously or similarly as described for compound C1.

C13 (E)-3-[1-(4-Pyrazol-1-yl-benzenesulfonyl)-1H-pyrrol-3-yl]-acrylic acid led-butyl ester Starting from (E)-3-(1H-pyrrol-3-yl)-acrylic acid tert-butyl ester (compound D1) and art-known 4-pyrazol-1-yl-benzenesulfonylchloride the title compound can be obtained analogously or similarly as described for compound C1.

C14 (E)-3-{1-[4-(Morpholin-4-yl-methyl)-benzenesulfonyl]-1H-pyrrol-3yl}-acrylic acid tert-butyl ester Starting from compound D2 and morpholine the title compound can be obtained analogously as described for compound C5.

C15 (E)-3-{1-[4-({[2-(tert-Butyl-dimethyl-silanyloxy)-ethyl]-[2-(1H-indol-3-yl)-ethyl]-amino}-methyl)-benzenesulfonyl]-1H-pyrrol-3-yl}-acrylic acid (E)-3-{3-[4-({[2-(tert-Butyl-dimethyl-silanyloxy)-ethyl]-2-(1H-indol-3-yl)-ethyl]-amino}-methyl)-benzenesulfonyl]-1H-pyrrol-3-yl}-acrylic acid tert-butyl ester (compound D5) is dissolved in dichloromethane (50 ml). Then it is added TFA and the mixture is stirred for 26 hours. After evaporation, the residue is washed with toluene.

D1 (E)-3-(1H-Pyrrol-3-yl)-acrylic acid tert-butyl ester 5.29 g of sodium hydride 60% is suspended in 100 ml of tetrahydrofurane under nitrogen at −30° C. 27.81 g of tert-butyl diphosphono acetate are added to the suspension and warmed slowly to room temperature and stirred for 30 minutes. Afterwards the mixture is recooled at −30° C. and it is added 5.24 g of 1H-pyrrol-3-carbaldehyde (compound E1) and stirred at −30° C. for 30 minutes. The suspension is warmed slowly to room temperature and 200 ml of aqueous ammonia solution are added. Then it is extracted with ethyl acetate. The combined organic phase is dried over Na$_2$SO$_4$, filtered and evaporated under vacuo. The crude product is purified by silica gel flash chromatography using a gradient of n-hexane-ethyl acetate from 2:1 to 1:1 to give 9.68 g of the title compound as a pale yellow solid.

MS (EI): 193.1 (M+); 137.1 (M+−C$_4$H$_8$, 100%)
$^1$H-NMR (DMSO-d6): 1.45 (s, 9H); 5.96 (d, J=15.7 Hz, 1H); 6.40 (m, 1H); 6.78 (m, 1H); 7.19 (m, 1H); 7.47 (d, J=15.7 Hz, 1H); 11.11 (bs, exchangeable, 1H)

D2 (E)-3-[1-(4-Bromomethyl-benzenesulfonyl)-1H-pyrrol-3-yl]-acrylic acid tert-butyl ester 4.25 g of sodium hydride (60% strength) are suspended in 300 ml of THF under nitrogen at −30° C. 9.78 g of (E)-3-(1H-pyrrol-3-yl)-acrylic acid tert-butyl ester (compound D1) are added to the suspension and warmed slowly to room temperature during 55 min. Afterwards it is recooled to −30° C. and it is added 13.98 g of 4-(bromomethyl)-benzenesulphonylchloride and stirred for 45 min. Then it is warmed to room temperature and stirred for 2 hour. After cooling to 0-5° C. water is added. Then the mixture is extracted with ethyl acetate and the organic phase is dried over sodium sulfate. The organic phase is evaporated under vacuum. The crude product is purified by silica gel flash chromatography using a gradient of hexane and ethyl acetate from 9:1-7:1.
Yield: 17.21 g, pale yellow solid

D3 (E)-3-{1-[4-(1,3-Dioxo-1,3-dihydro-isoindol-2-ylmethyl)-benzenesulfonyl]-1H-pyrrol-3-yl}-acrylic acid tert-butyl ester 10 g (E)-3-[1-(4-bromomethyl-benzenesulfonyl)-1H-pyrrol-3-yl]-acrylic acid tert-butyl ester (compound D2) is dissolved in acetone and 6.5 g potassium phthalimide is added and the mixture is stirred for 17.5 h. The suspension is filtered and the product is purified by crystallization.

D4 (E)-3-[1-(4-Bromo-benzenesulfonyl)-1H-pyrrol-3-yl]-acrylic acid tert-butyl ester Starting from compound D1 and 4-bromo-benzenesulfonyl chloride the title compound can be obtained analogously as described for compound D2.

D5 (E)-3-{1-[4-({[2-(tert-Butyl-dimethyl-silanyloxy)-ethyl]-[2-(1H-indol-3-yl)-ethyl]-amino}-methyl)-benzenesulfonyl]-1H-pyrrol-3-yl}-acrylic acid tert-butyl ester

[2-(tert-Butyl-dimethyl-silanyloxy)-ethyl]-[2-(1H-indol-3-yl)-ethyl]-amine (compound E2) (830 mg, 2.60 mmol) is dissolved in ethanol (200 ml). (E)-3-[1-(4-bromomethyl-benzenesulfonyl)-1H-pyrrol-3yl]-acrylic acid tert-butyl ester (compound D4) (1.01 g, 2.37 mmol) is added and the mixture is stirred for 43 hours and evaporated. The residue is purified by a silica gel flash chromatograph using petrol ether-ether eluent.

(E)-3-[1-(3-Bromo-benzenesulfonyl)-1H-pyrrol-3-yl]-acrylic acid tert-butyl ester Starting from compound D1 and 3-bromo-benzenesulfonyl chloride the title compound can be obtained analogously as described for compound D4.

E1 1H-Pyrrol-3-carbaldehyde 4.70 g of dimethyl-(1H-pyrrol-3-ylmethylene)-ammonium chlorid (compound F1) are dissolved in 500 ml of 5.0% aqueous sodium hydroxide solution and stirred for 4 hours at ambient temperature. Afterwards the reaction mixture is extracted exhaustively with CH$_2$Cl$_2$. The combined organic phase is dried over Na$_2$SO$_4$. Then it is filtered and evaporated under vacuo. The crude product is purified by a silica gel flash chromatography using petroleum ether/diethylether 1:1 eluent to yield 3.01 g of the title compound as a pale yellow solid.
MS (EI): 95.1 (M+, 100%)
$^1$H-NMR (DMSO-d6): 6.42 (dd, J$_1$=1.5 Hz, J$_2$=6.5 Hz, 1H); 6.90 (m, 1H), 7.69 (dd, J$_1$=1.5 Hz, J$_2$=6.4 Hz, 1H); 9.68 (s, 1H); 11.59 (bs, exchangeable, 1H)

E2 [2-(tert-Butyl-dimethyl-silanyloxy)-ethyl]-[2-(1H-indol-3-yl)-ethyl]-amine Tryptamine (3.34 g, 20.85 mmol) and t-butyldimethylsilyloxyacetaldehyde (2.44 g, 13.99 mmol) is dissolved in dichloromethane (200 ml) for 10 minutes. The mixture is cooled to 0° C. and it is added sodium triacetoxyborohydride (5.38 g, 25.38 mmol). The mixture is warmed slowly to room temperature and stirred for 18 hours. Then water is added and the mixture is extracted with dichloromethane. The organic phase is dried over sodium sulfate, filtered and evaporated. The crude product is purified by a silica gel flash chromatograph using dichloromethane-methanol eluent.

F1 Dimethyl-(1H-pyrrol-3-ylmethylene)-ammonium chlorid 10.60 g of (chloromethylene)dimethylammonium chloride and 6.25 g of N-(triisopropylsilyl)-pyrrole are suspended in 200 ml of CH$_2$Cl$_2$ under nitrogen at 0-5° C. The suspension is warmed to 60° C. and stirred for 30 minutes. Afterwards the mixture is cooled to ambient temperature. The suspension is filtered and washed with diethylether to give 5.67 g of the title compound as grey solid.
MS (ESI): 123.3 (MH+, 100%)
$^1$H-NMR (DMSO-d6): 3.55 (s, 3H); 3.63 (s, 3H); 6.82 (m, J$_1$=1.4 Hz, J$_2$=1.5 Hz, J$_3$=J$_4$=4.8 Hz, 1H); 7.22 (dd, J$_1$=4.7 Hz, J$_2$=4.9, 1H), 8.00 (dd, J$_1$=1.6 Hz, J$_2$=1.7 Hz, 1H); 8.78 (s, 1H); 12.94 (bs, exchangeable, 1H)

Commercial Utility

The N-sulphonylpyrrole derivatives of formula I or the salts of these compounds have valuable pharmacological properties by inhibiting histone deacetylase activity and function.

Histone deacetylase (HDAC) means an enzyme with an activity towards the δ-acetyl group of lysine residues within a substrate protein. HDAC substrates are histone H2A, H$_2$B, H3 or H4 proteins and isoforms but substrate proteins different to histones like, but not limited to, heat shock protein 90 (Hsp90), tubulin or the tumor suppressor protein p53 exist. In particular histone deacetylases catalyse the hydrolysis the ε-acetyl group of lysine residues within these substrate proteins, forming the free amino group of lysine.

Inhibition of histone deacetylase by compounds according to this invention means inhibiting the activity and function of one or more HDAC isoenzymes, in particular isoenzymes selected from the so far known histone deacetylases, namely HDAC 1, 2, 3 and 8 (class I) and HDAC 4, 5, 6, 7, 10 (class II); HDAC 11 as well as the NAD+ dependent class III (Slr2 homologues). In some preferred embodiment this inhibition is at least about 50%, more preferable at least 75% and still more preferable above 90%. Preferably, this inhibition is specific to a specific histone deacetylase class (e.g. HDAC class I enzymes), a selection of isoenzymes of highest pathophysiological relevance (e.g. HDAC1, 2, 3 enzymes) or a single isoenzyme (e.g. the HDAC 1 enzyme). The term histone deacetylase inhibitor is used to identify a compound capable of interacting with a histone deacetylase and inhibiting its activity, in particular its enzymatic activity. In this context "head group" defines the residues within an histone deacetylase inhibitor responsible for interacting with the active site of the enzyme, e.g. the $Zn^{2+}$ ion.

The inhibition of histone deacetylases is determined in biochemical assays of various formats and sources of enzymatic activity. HDAC activity is used either derived from nuclear or cellular extracts or by heterologous expression of a defined HDAG isoenzymes in E. coli, insect cells or mammalian cells. Since HDAC are active in multiprotein complexes and form homo- and heterodimeres, nuclear extracts derived from human cancer cells, for example the human cervical carcinoma cell line HeLa, are preferred. These nuclear extracts contain class I and class II enzymes, but are enriched in class 1 enzymes. For expression of recombinant HDAC isoenzymes, mammalian expression systems like HEK293 cells are preferred. The HDAC isoenzyme is expressed as a fusion protein with an affinity tag, like the FLAG epitope. By affinity chromatography, the tagged protein is purified alone or in complex with endogenous proteins (e.g. other HDAC isoenzmyes and coactivators/platform proteins).

The biochemical assays are well described and well known to persons skilled in the art. As substrates, histone proteins, peptides derived from histone proteins or other HDAG substrates as well as acetylated lysine mimetics are used. One preferred promiscous HDAC substrate is the tripeptide Ac-NH-GGK(Ac), coupled with the fluorophore 7-aminomethylcoumarin (AMC).

The invention further relates to the use of the compounds according to this invention for inhibiting histone deacetylase activity in cells and tissues, causing hyperacetylation of substrate proteins and as functional consequence for example the induction or repression of gene expression, induction of protein degration, cell cycle arrest, induction of differentiation and/or induction of apoptosis.

Cellular activity of a histone deacetylase inhibitor means any cellular effect related to histone deacetylase inhibition, in particular protein hyperacetylation, transcriptional repression and activation, induction of apoptosis, differentiation and/or cytotoxicity.

The term "induction of apoptosis" and analogous terms are used to identify a compound which executes programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily coupled with inhibition of cell proliferation or cell differentiation. Preferably, the inhibition of proliferation, induction of differentiation and/or induction of apoptosis is specific to cells with aberrant cell growth.

"Cytotoxicity" in general means arresting proliferation and/or inducing apoptotic cell death in vitro in mammalian cells, in particular human cancer cells.

"Induction of differentiation" is defined as a process of cellular reprogramming leading to a reversible or irreversible cell cycle arrest in G0 and re-expression of a subset of genes typical for a certain specialized normal cell type or tissue (e.g. re-expression of milk fat proteins and fat in mammary carcinoma cells).

Assays for quantification of cell proliferation, apoptosis or differentiation are well known to experts and state of the art. For example, metabolic activity which is linked to cellular proliferation is quantified using the Alamar Blue/Resazurin assay (O'Brian et al. Eur j Biochem 267, 5421-5426, 2000) and induction of apoptosis is quantified by measurement of chromatin fragmentation with the cell death detection ELISA commercialized by Roche. Examples for cellular assays for the determination of hyperacetylation of HDAC substrates are given by measuring core histone acetylation using specific antibodies by Western blotting, reporter gene assays using respective responsive promoters or promoter elements (e.g. the p21 promoter or the sp1 site as responsive element) or finally by image analysis again using acetylation specific antibodies for core histone proteins.

Compounds according to this invention can be commercially applicable due to their HDAC inhibitory, anti-proliferative and/or apoptosis inducing activity, which may be beneficial in the therapy of diseases responsive thereto, such as e.g. any of those diseases mentioned herein.

The invention further relates to a method for inhibiting or treating cellular neoplasia by administration of an effective amount of a compound according to this invention to a mammal, in particular a human in need of such treatment. A "neoplasia" is defined by cells displaying aberrant cell proliferation and/or survival and/or a block in differentiation. The term neoplasia includes "benign neoplasia" which is described by hyperproliferation of cells, incapable of forming an aggressive, metastasizing tumor in-vivo, and, in contrast, "malignant neoplasia" which is described by cells with multiple cellular and biochemical abnormalities, capable of forming a systemic disease, for example forming tumor metastasis in distant organs.

The N-sulphonylpyrrole derivatives of the present invention are preferably used for the treatment of malignant neoplasia, also described as cancer, characterized by tumor cells finally metastasizing into distinct organs or tissues. Examples of malignant neoplasia treated with the N-sulphonylpyrrole derivatives of the present invention include solid and haematological tumors. Solid tumors are exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small Intestine, soft tissue, testis, stomach, skin, ureter, vagina and vulva. Malignant neoplasia include Inherited cancers exemplified by Retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

Neoplastic cell proliferation might also effect normal cell behaviour and organ function. For example the formation of new blood vessels, a process described as neovascularization, is induced by tumors or tumor metastases. N-sulphonylpyrrole derivatives as described herein can be commercially applicable for treatment of pathophysiological relevant processes caused by benign or neoplastic cell proliferation, such as but not limited to neovasoularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps, mutation within the cellular target protein or fusion proteins formed by chromosomal translocations. The commercial applicability of N-sulphonylpyrrole derivatives according to the present invention is not limited to $1^{st}$ line treatment of patients. Patients with resistance to cancer chemotherapeutics or target specific anticancer drugs can be also amenable for treatment with these compounds for e.g. $2^{nd}$ or $3^{rd}$ line treatment cycles. A prominent example is given by acute promyelocytic leukemia patients with the PML-RARα fusion protein, resistant to standard therapy with retinoids. These patients can be resensitized towards retinoids by treatment with HDAC inhibitory drugs like the N-sulphonylpyrrole derivatives according to the present invention.

The invention further provides to a method for treating a mammal, in particular a human, bearing a disease different to cellular neoplasia, sensitive to histone deacetylase inhibitor therapy comprising administering to said mammal a pharmacologically active and therapeutically effective and tolerable amount of a compound according to this invention. These non malignant diseases include
(i) arthropathies and osteopathological conditions such as rheumatoid arthritis, osteoarthrtis, gout, polyarthritis, and psoriatic arthritis,
(ii) systemic lupus erythematosus,
(iii) smooth muscle cell proliferation including vascular proliferative disorders, atherosclerosis and restenosis
(iv) inflammatory conditions and dermal conditions such as ulcerative colitis, Chrons disease, allergic rhinitis, allergic dermatitis, cystic fibrosis, chronic bronchitis and asthma
(v) endometriosis, uterine fibroids, endometrial hyperplasia and benign prostate hyperplasia
(vi) cardiac dysfunction
(vii) inhibiting immunosuppressive conditions like HIV infections
(viii) neuropathological disorders like Parkinson disease, Alzheimer disease or polyglutamine related disorders
(ix) pathological conditions amenable to treatment by potentiating of endogenous gene expression as well as enhancing transgene expression in gene therapy.

The present invention further includes a method for the treatment of mammals, including humans, which are suffering from one of the abovementioned conditions, illnesses, disorders or diseases. The method is characterized in that a pharmacologically active and therapeutically effective and tolerable amount of one or more of the N-sulphonylpyrrole derivatives mentioned above, or a salt of said compounds of formula which function by inhibiting histone deacetylases and, by modulating protein acetylation, induce various cellular effects, in particular induction or repression of gene expression, arresting cell proliferation and/or inducing apoptosis, is administered to the subject in need of such treatment.

The invention further includes a method for treating diseases and/or disorders responsive or sensitive to the inhibition of histone deacetylases, particularly those diseases mentioned above, such as e.g. cellular neoplasia or diseases different to cellular neoplasia as indicated above, in mammals, including humans, suffering therefrom comprising administering to said mammals in need thereof a pharmacologically active and therapeutically effective and tolerable amount of one or more of the compounds according to the present invention.

The present invention further includes a therapeutic method useful to modulate protein acetylation, gene expression, cell proliferation, cell differentiation and/or apoptosis in vivo in diseases mentioned above, in particular cancer, comprising administering to a subject in need of such therapy a pharmacologically active and therapeutically effective and tolerable amount of one or more of the abovementioned N-sulphonylpyrrole derivates, or the salts of said compounds of formula I, which function by inhibiting histone deacetylases.

The present invention further provides a method for regulating endogenous or heterologous promotor activity by contacting a cell with a compound of formula I as mentioned above.

The invention further includes a method for treating diseases, particularly those diseases mentioned above, in mammals, including humans, suffering therefrom comprising administering to said mammals in need thereof a therapeutically effective and tolerable amount of one or more of the compounds according to the present invention, optionally, simultaneously, sequentially or separately with one or more further therapeutic agents, such as e.g. those mentioned below.

The invention further relates to the use of the compounds according to the present invention for the production of pharmaceutical compositions which are employed for the treatment and/or prophylaxis of the diseases, disorders, illnesses and/or conditions as mentioned herein.

The invention further relates to the use of the compounds according to the present invention for the production of pharmaceutical compositions which are employed for the treatment and/or prophylaxis of diseases and/or disorders responsive or sensitive to the inhibition of histone deacetylases, particularly those diseases mentioned above, such as e.g. cellular neoplasia or diseases different to cellular neoplasia as indicated above.

The invention further relates to the use of the compounds according to the present invention for the production of pharmaceutical compositions having histone deacetylases inhibitory activity.

The invention further relates to the use of the compounds according to the present invention for the production of pharmaceutical compositions for inhibiting or treating cellular neoplasia, such as e.g. benign or malignant neoplasia, e.g. cancer.

The invention further relates to the use of the compounds according to the present invention for the production of pharmaceutical compositions for the treatment of a disease different to a cellular neoplasia and sensitive to histone deacetylase inhibitor therapy, such as the non-malignant diseases mentioned before.

The invention further relates to the use of the compounds according to the present invention for the production of pharmaceutical compositions for inhibiting histone deacetylase activity in the treatment of diseases responsive to said inhibition or to the functional consequences thereof.

The invention further relates to a method for treating, preventing or ameliorating the diseases, disorders, illnesses and/or conditions mentioned herein in a mammal, in particular a human patient, comprising administering a pharmacologically active and therapeutically effective and tolerable amount of one or more compounds according to the present invention to said mammal in need thereof.

The invention further relates to the compounds according to this invention for use in the treatment and/or prophylaxis of diseases, especially the diseases mentioned.

The invention further relates to pharmaceutical compositions comprising one or more of the compounds according to this invention and a pharmaceutically acceptable carrier or diluent.

The invention further relates to pharmaceutical compositions according to this invention having histone deacetylases inhibitory activity.

The invention further relates to pharmaceutical compositions according to this invention having apoptosis inducing activity.

The invention further relates to pharmaceutical compositions according to this invention antiproliferative activity.

The invention further relates to the use of a pharmaceutical composition comprising one or more of the compounds according to this invention and a pharmaceutically acceptable carrier or diluent in the manufacture of a pharmaceutical product, such as e.g. a commercial package, for use in the treatment and/or prophylaxis of the diseases as mentioned.

Additionally, the invention relates to an article of manufacture, which comprises packaging material and a pharmaceutical agent contained within said packaging material, wherein the pharmaceutical agent is therapeutically effective for inhibiting the effects of histone deacetylases, ameliorating the symptoms of an histone deacetylase mediated disorder, and wherein the packaging material comprises a label or package insert which indicates that the pharmaceutical agent is useful for preventing or treating histone deacetylase mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

Depending upon the particular disease, to be treated or prevented, additional therapeutic active agents, which are normally administered to treat or prevent that disease, may optionally be coadministered with the compounds according to the present invention. As used herein, additional therapeutic agents that are normally administered to treat or prevent a particular disease are known as appropriate for the disease being treated.

In a further aspect of the present invention, the N-sulphonylpyrrole derivatives according to this invention or the salts of said compounds of formula I, which function by inhibiting histone deacetylases, may be combined with standard therapeutic agents used for treatment of the diseases as mentioned before. In one particular embodiment the N-sulphonylpyrrole derivatives may be combined with one or more art-known anti-cancer agents, such as e.g. art-known chemotherapeutic and/or target specific anti-cancer agents.

Examples of known chemotherapeutic anti-cancer agents used in cancer therapy include, but not are limited to (i) alkylating/carbamylating agents such as Cyclophosphamid (Endoxan®), Ifosfamid (Holoxan®), Thiotepa (Thiotehpa Lederle®), Melphalan (Alkerane), or chloroethylnitrosourea (BCNU); (i) platinum derivatives like cis-platin (Platinex® BMS), oxaliplatin or carboplatin (Cabroplat® BMS); (iii) antimitotic agents/tubulin inhibitors such as vinca alkaloids (vincristine, vinblastine, vinorelbine), taxanes such as Taxol (Paclitaxel®), Taxotere (Docetaxel®) and analogs as well as new formulations and conjugates thereof; (iv) topoisomerase inhibitors such as anthracyclines (exemplified by Doxorubicin/Adriblastin®), epipodophyllotoxines (exemplified by Etoposide/Etopophos®) and camptothecin analogs (exemplified by Topotecan/Hycamtin®); (v) pyrimidine antagonists such as 5-fluorouracil (5-FU), Capecitabine (Xeloda®), Arabinosylcytosine/Gytarabin (Alexan®) or Gemcitabine (Gemzar®); (vi) burin antagonists such as 6-mercaptopurine (Puri-Nethol®), 6-thioguanine or fludarabine (Fludara®) and finally (vii) folic acid antagonists such as methotrexate (Farmitrexat®).

Examples of target specific anti-cancer drug classes used in experimental or standard cancer therapy include but are not limited to (i) kinase inhibitors such as e.g. Glivec (Imatinib®), ZD-1839/Iressa (Gelitinib®), Bay43-9006 (Sorafenib®), SW 1248 (Sutent®) or OSI-774/Tarceva (Erlotinib®); (ii) proteasome inhibitors such as PS-341 (Velcade®); (iii) heat shock protein 90 inhibitors like 17-allylaminogeldanamycin (17-AAG); (iv) vascular targeting agents (VTAs) and anti-angiogenic drugs like the VEGF antibody Avastin (Bevacizumab®) or the KDR tyrosine kinase inhibitor PTK787/ZK222584 (Vatalanib®); (v) monoclonal antibodies such as Herceptin (Trastuzumab®) or MabThera/Rituxan (Rituximab®), mutants as well as conjugates of monoclonal antibodies and antibody fragments; (vi) oligonucleotide based therapeutics like G-3139/Genasense (Oblimersen®); (vii) protease inhibitors (viii) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors.

Other known anti-cancer agents which can be used for combination therapy include bleomycin, retinoids such as all-trans retinoic acid (ATRA), DNA methyltransferase inhibitors such as the 2-deoxycytidine derivative Decitabine (Decagon®), alanosine, cytokines such as interleukin-2, interferons such as interferon α2 or interferon-γ, TRAIL, DR4/5 agonistic antibodies, FasL and TNF-R agonists and finally histone deacetylase inhibitors different to sulphonylpyrrole derivatives as described in the present invention such as SAHA, PXD101, MS275, MGCD0103, Depsipeptide/FK228, NVP-LBH589, valproic acid (VPA) and butyrates.

As exemplary anti-cancer agents for use in combination with the compounds according to this invention in the cotherapies mentioned herein the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BICALUTAMIDE, BLEOMYCIN, BROXURIDINE, BUSULFAN, CAPECITABINE, CARBOPLATIN, GARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, LANREOTIDE, LETROZOLE, LEUPRORELIN, LOBAPLATIN, LOMUSTINE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PEGASPARGASE, PEGFILGRASTIM, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALTITREXED, RANIMUSTINE, RANPIRNASE, RASBURICASE, RAZOXANE, RITUXIMAB, RIFAMPICIN, FIITROSULFAN, ROMURTIDE, RUBOXISTAURIN, SARGRAMOSTIM, SATRAPLATIN, SIROLIMUS, SOBUZOXANE, SPIROMUSTINE, STREPTOZOCIN, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRASTUZUMAB, TREOSULFAN, TRIAZIQUONE, TRIMETREXATE, TRIPTORELIN, TROFOSFAMIDE, UREDEPA, VALRUBICIN, VERTEPORFIN, VINBLASTINE, VINCRISTINE, VINDESINE, VINORELBINE and VOROZOLE.

The person skilled in the art is aware on the base of his/her expert knowledge of the total daily dosage(s) and administration form(s) of the additional therapeutic agent(s) coadministered. Said total daily dosage(s) can vary within a wide range.

In practicing the present invention and depending on the details, characteristics or purposes of their uses mentioned above, the compounds according to the present invention may be administered in combination therapy separately, sequentially, simultaneously or chronologically staggered (e.g. as combined unit dosage forms, as separate unit dosage forms or a adjacent discrete unit dosage forms, as fixed or non-fixed combinations, as kit-of-parts or as admixtures) with one or more standard therapeutics, in particular art-known chemotherapeutic or target specific anti-cancer agents, such as those mentioned above.

Thus, a further aspect of the present invention is a combination or pharmaceutical composition comprising a first active ingredient, which is a N-sulphonylpyrrole derivative according to this invention or a salt thereof, a second active ingredient, which is an art-known standard therapeutic, in particular art-known chemotherapeutic or target specific anti-cancer agent, such as one of those mentioned above, and optionally a pharmacologically acceptable carrier, diluent and/or excipient for sequential, separate, simultaneous or chronologically staggered use in therapy in any order, e.g. to treat, prevent or ameliorate in a patient diseases responsive to HDAC inhibitor treatment, such as the diseases, disorders or Illnesses mentioned, in particular cancer.

In this context, the present invention further relates to a combination comprising a first active ingredient, which is at least one compound according to this invention, and a second active ingredient, which is at least one art-known standard therapeutic, for example an art-known anti-cancer agent, such as e.g. one or more of those mentioned herein above, for separate, sequential, simultaneous or chronologically staggered use in therapy, such as e.g. in therapy of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a disease responsive or sensitive the inhibition of histone deacetylases, particularly one of those diseases mentioned herein.

A further aspect of the present invention is a combination comprising, in non-fixed form, one or more N-sulphonylpyrrole derivatives according to this invention or the salts thereof, and one or more art-known standard therapeutic, in particular art-known chemotherapeutic or target specific anti-cancer agents, such as those mentioned above, for sequential, separate, simultaneous or chronologically staggered use in therapy in any order, e.g. to treat, prevent or ameliorate in a patient diseases responsive to HDAC inhibitor treatment, such as the diseases, disorders or illnesses mentioned, in particular cancer. Optionally said combination comprises instructions for its use in therapy.

A further aspect of the present invention is a combined preparation, such as e.g. a kit of parts, comprising a preparation of a first active ingredient, which is a compound according to this invention and a pharmaceutically acceptable carrier or diluent; a preparation of a second active ingredient, which is an art-known therapeutic agent, in particular an anti-cancer agent, such as e.g. one of those mentioned above, and a pharmaceutically acceptable carrier or diluent; and optionally instructions for simultaneous, sequential, separate or chronologically staggered use in therapy, e.g. to treat benign and malignant neoplasia or diseases different to cellular neoplasia responsive or sensitive to the inhibition of histone deacetylases.

A further aspect of the present invention is a kit of parts comprising a dosage unit of a first active ingredient, which is a sulphonylpyrrole derivative mentioned in above or a salt thereof, a dosage unit of a second active ingredient, which is an art-known standard therapeutic, in particular an anti-cancer agent such as e.g. one of those mentioned above, and optionally instructions for simultaneous, sequential or separate use in therapy, e.g. to treat disorders responsive or sensitive to the inhibition of histone deacetylases, such as, for example, benign or malignant neoplasia, e.g. cancer.

A further aspect of the present invention is a pharmaceutical product comprising one or more compounds according to this invention, or one or more pharmaceutical compositions comprising said compounds; and one or more art-known therapeutic agents, in particular art-known anti-cancer agents, or one or more pharmaceutical compositions comprising said therapeutic agents, such as e.g. those mentioned above, for simultaneous, sequential or separate use in therapy, e.g. to treat diseases as mentioned before, in particular cancer. Optionally this pharmaceutical product comprises instructions for use in said therapy. In this connection, the present invention further relates to combinations, compositions, formulations, preparations or kits according to the present invention having histone deacetylases inhibitory activity.

A further aspect of the present invention is a pharmaceutical composition as unitary dosage form comprising, in admixture, a first active ingredient, which is a N-sulphonylpyrrole derivative according to this invention or a salt thereof, a second active ingredient, which is an art-known standard therapeutic, in particular art-known chemotherapeutic or target specific anti-cancer agent, such as one of those mentioned above, and optionally a pharmacologically acceptable carrier, diluent or excipient.

A further aspect of the present invention is a commercial package comprising one or more compounds according to the present invention together with instructions for simultaneous, sequential or separate use with one or more art-known standard therapeutic, in particular anti-cancer, agents such as those mentioned above.

The pharmaceutical compositions, combinations, preparations, formulations, kits, products or packages mentioned above may also include more than one of the compounds according to this invention and/or more than one of the art-known standard therapeutics, in particular anti-cancer agents as mentioned.

Furthermore, also an aspect of the present invention is a method for treating diseases and/or disorders responsive or sensitive to the inhibition of histone deacetylases, such as e.g. cancer, in combination therapy in a patient comprising administering a pharmacologically active and therapeutically effective and tolerable amount of a pharmaceutical combination, composition, formulation, preparation or kit as described above to said patient in need thereof.

A further aspect of the present invention is a method for treating cotherapeutically diseases responsive or sensitive to inhibiting histone deacetylases, such as e.g. those diseases as mentioned before, in a patient in need of such treatment comprising administering separately, sequentially, simultaneously, fixed or non-fixed a pharmacologically active and therapeutically effective and tolerable amount of one or more of the compounds according to the present invention and a pharmacologically active and therapeutically effective and tolerable amount of one or more art-known therapeutic agents, in particular anti-cancer agents, such as those mentioned above, to said patient.

In addition, compounds according to the present invention can be used in the pre- or post-surgical treatment of cancer.

In further addition, compounds according to the present invention can be used in combination with radiation therapy. In particular in sensitization of cancer patients towards standard radiation therapy.

The administration of the compounds according to this invention, the combinations and pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the N-sulphonylpyrrole derivatives of the invention are in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for histone deacetylases inhibitors. Topical application forms (such as ointments) for the treatment of dermatoses thus contain the active compounds in a concentration of, for example, 0.1-99%. The customary dose in the case of systemic therapy (p.o.) is between 0.3 and 30 mg/kg per day, (i.v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Biological Investigations
Isolation of HDAC Activity from HeLa Cell Nuclei:

HDAC activity was isolated from nuclear HeLa extracts according to a method original described by Dignam et al. (Nucl. Acids Res. 11, pp 1475, 1983). Briefly, nuclei isolated from HeLa cells (CIL SA, Seneffe, Belgium) were resuspended in buffer C (20 mM Hepes pH 7.9, 25% v:v glycerol, 0.42M NaCl, 1.5 mM $MgCl_2$, 0.2 mM EDTA, 0.5 mM PefaBloc and 0.5 mM DTT) and stirred for 30 min on ice. After centrifugation, the supernatant was dialysed against buffer D (40 mM Iris HCl pH 7.4, 100 mM KCl, 0.2 mM EDTA, 0.5 mM DTT and 25% v:v glycerol) for 5 h at 4° C.

After dialysis and centrifugation, the supernatant was stored in aliquots at −80° C. and used for Western blot analysis as well as the enzymatic assay as described in the following.

Isolation of rHDAC1

Human HDAC1 fused with the flag epitope is stably expressed in Hek293 cells. After mass cultivation in DMEM with supplements and 2% fetal calf serum, cells are lysed and flag-HDAC1 purified by M2-agarose affinity chromatography as described (Sigma Art. No. A-2220). Fractions from the purification are analysed by Western blot as well as for enzymatic activity as described below.

Fluorimetric HDAC Activity Assay:

The HDAC enzyme activity assay was done as described by Wegener et al. (Chem. & Biol. 10, 61-68, 2003). Briefly 40 µl of a 1:100 dilution (=0.4 µl) nuclear HeLa extract (mixture of class I and II HDACs), 29 µl enzyme buffer (15 mM Tris HCl pH 8.1, 0.25 mM EDTA, 250 mM NaCl, 10% v:v glycerol) and 1 µl test compound were added to a well of a 96 well microtiter plate and reaction started by addition of 30 µl substrate (Ac-NH-GGK(Ac)-AMC; final concentration 25 µM and final volume 100 µl). After incubation for 90 min at 30° C., reaction was terminated by the addition of 25 µl stop solution (50 mM Tris HCl pH 8, 100 mM NaCl, 0.5 mg/ml trypsine and 2 µM TSA). After incubation at room temperature for further 40 min, fluorescence was measured using a Wallac Victor 1420 multilabel counter (Ex 355 nm, Em 460 nm) for quantification of AMC (7-amino-4-methylcoumarin) generated by trypsine cleavage of the deacetylated peptide. For the calculation of $IC_{50}$ values the fluorescence in wells without test compound (1% DMSO, negative control was set as 100% enzymatic activity and the fluorescence in wells with 2 µM TSA (positive control) were set at 0% enzymatic activity. The corresponding $IC_{50}$ values of the compounds for HDAC inhibitory activity were determined from the concentration-effect curves by means of non-linear regression.

The HDAC inhibitory activity expressed by $IC_{50}$ values for selected compounds according to the present invention is shown in the following table 1, in which the numbers of the compounds correspond to the numbers of the examples.

TABLE 1

HDAC inhibitory activity (HDAC activity isolated from HeLa nuclear extract)

| Compound | $IC_{50}$ (µM) |
|---|---|
| 1 | The $IC_{50}$ values of these |
| 2 | listed compounds are in |
| 3 | the range from 0.0036 to 2.74 |
| 4 | |
| 7 | |
| 8 | |
| 9 to 28 | The $IC_{50}$ values of these listed compounds are in the range from 0.002 to 40 |

The HDAC1 enzymatic assay is done with slight modifications with recombinant flag-HDAC1 protein isolated from HEK293 cell lysates. About 14 ng/well flag-HDAC1 are incubated with 6 µM Ac-NH-GGK(Ac)-AMC substrate for 3 h at 30° C. Termination of the reaction and all further steps are done as described for HeLa cell nuclear extracts as a source for HDAC enzymatic activity.

Recombinant human HDAC1 expressed in Hek293 cells is inhibited by Examples 4, 5, 8 to 11, 25 and 28 with an $IC_{50}$=0.95 nM.

Cellular Histone H3 Hyperacetylation Assay:

To assess the cellular efficacy of an histone deacetylase inhibitor in vitro, an assay was set up in black clear-bottom 96-well plates and optimized for use on the Cellomics "Array-Scan II" platform for a quantitative calculation of histone acetylation. The protocol uses a polyclonal rabbit antibody, specifically binding to acetylated lysine 23 of human histone H3 on fixed cells with an Alexa Fluor 488 labeled goat anti rabbit-IgG used for counterstaining (Braunger et al. AACR annual conference 2003, Abstract 4556). $5 \times 10^3$ HeLa cervical carcinoma cells/well (ATCC CCL-2) in 200 µl Dulbecco's modified Eagle's medium (DMEM) containing 10% fetal calf serum were seeded at day 1 in Packard view plates and incubated for 24 h under standard cell culture conditions. On day 2, 2 µl test compound (100× final concentration) was added and incubation continued for further 24 h. On day 3, the culture medium was discarded and attached cells fixed for 15 min at room temperature by addition of 100 µl fixation buffer (3.7% v:v formaldehyde in phosphate buffered saline/PBS). After discarding the fixation buffer and one wash with PBS, cells were permeabilized at room temperature by addition of 100 µl/well permeabilization buffer (30.8 mM NaCl, 0.54 mM $Na_2HPO_4$, 0.31 mM $KH_2PO_4$, 5% v:v Triton X-100) for 15 min at room temperature. After discarding the permeabilization buffer and addition of 100 µl/well blocking solution (PBS with 0.05% v:v Tween 20 and 5% w:v milk powder) for 30 min at room temperature, the $1^{st}$ antibody (anti-K23 histone H3 antibody, Cell Signaling No. 9674) in blocking solution (50 µl/well) was added. After incubation for 1 h at 37° C., the wells were washed 5 times for 5 min at room temperature with wash buffer (PBS with 0.05% v:v Tween 20) before addition of the $2^{nd}$ antibody (goat-anti-rabbit Alexa Fluor 488; MoBiTec No. A-11008) in blocking solution (50 µl/well). After further incubation for 30 min at 37° C., wells were washed 5 times for 5 min at RT with 100 µl wash buffer at room temperature. Finally, 100 µl/well PBS were added and image analysis performed on the Cellomics "ArrayScan II" platform. For calculation of $EC_{50}$ values, the nuclear fluorescence in cells treated with and without a reference HDAC inhibitor like SAHA or NVP-LBH-589 were taken as a positive and negative control, respectively. For $EC_{50}$ determination, the percentage of positive cells was determined and $EC_{50}$ calculation done from concentration-effect curves by means of non-linear regression.

The histone hyperacetylating cellular potency expressed by $EC_{50}$ values for selected compounds according to the present invention is shown in the following table 2, in which the numbers of the compounds correspond to the numbers of the examples.

TABLE 2

Induction of histone $H3K^{23}$ hyperacetylation in HeLa cervical carcinoma cells

| Compound | $EC_{50}$ (µM) |
|---|---|
| 1 | The $EC_{50}$ values of these |
| 2 | listed compounds are in |
| 3 | the range from 2.15 to 51.3 |
| 4 | |
| 7 | |
| 8 | |
| 9, 10 and 27 | |

Cellular Cytotoxicity Assay:

The anti-proliferative activity of the histone deacetylase inhibitory compounds as described herein, was evaluated with the HeLa cervical carcinoma cell line (ATCC CCL2) using the Alamar Blue (Resazurin) cell viability assay (O'Brien at al. Eur J Biochem 267, 5421-5426, 2000). Resazurin is reduced to the fluorescent resorufin by cellular dehydrogenase activity, correlating with viable, proliferating cells. Test compounds were dissolved as 10 mM solutions in dimethylsulfoxide (DMSO) and subsequently diluted in semi-logarithmic steps. HeLa cells were seeded into 96 well flat bottom plates at a density of 3000 cells per well in a volume of 200 µl per well. 24 hours after seeding 1 µl each of the compound dilutions were added into each well of the 96 Well plate. Each compound dilution was tested as quadruplicates. Wells containing untreated control cells were filled with 200 µl OMEM medium containing 0.5% v:v DMSO. The cells were then incubated with the substances for 48 hours at 37° C. in a humidified atmosphere containing 5% carbon dioxide. To determine the viability of the cells, 20 µl of an Resazurin solution (Sigma; 90 mg/l) were added. After 4 hours incubation at 37° C. the fluorescence was measured at an extinction of 544 nm and an emission of 590 nm. For the calculation of the cell viability the emission value from untreated cells was set as 100% viability and the emission rates of treated cells were set in relation to the values of untreated cells. Viabilities were expressed as % values. The corresponding $IC_{50}$ values of the compounds for cytotoxic activity are determined from the concentration-effect curves by means of non-linear regression.

The anti-proliferative/cytotoxic potency expressed by $IC_{50}$ values for selected compounds according to the present invention is shown in the following table 3, in which the numbers of the compounds correspond to the numbers of the examples.

TABLE 3

| Cytotoxicity in HeLa cervical carcinoma cells | |
|---|---|
| Compound | $IC_{50}$ (µM) |
| 1 | The $IC_{50}$ values of these |
| 2 | listed compounds are in |
| 3 | the range from 0.8 to 21.6 |
| 4 | |
| 7 | |
| 8 | |
| 9 to 28 | The $IC_{50}$ values of these listed compounds are in the range from 0.07 to 5 |

Apoptosis Induction

The induction of apoptosis is measured by using the cell death detection ELISA (Art. No. 1774425, Roche Biochemicals, Mannheim, Germany). A549 NSCLC cells are seeded into 96 well flat bottom plates at a density of 3×10 E3 cells/well in a total volume of 100 µl/well. 24 hours after seeding, 1 µl each of the compound dilutions in DMEM are added in a total volume of 100 µl into each well Final volume 200 µl/well). Each compound dilution is tested at least as triplicates. Wells containing untreated control cells are filled with 200 µl DMEM containing 0.5 vol % DMSO. The cells are incubated with test compound for 48 hours at 37° C. in a humidified atmosphere containing 5% carbon dioxide. As a positive control for the induction of apoptosis, cells are treated with 50 µM Cisplatin (Gry Pharmaceuticals, Kirchzarten, Germany). Medium is then removed and the cells lysed in 200 µl lysis buffer. After centrifugation as described by the manufacturer, 10 µl of cell lysate is processed as described in the protocol. The degree of apoptosis is calculated as follows: The absorbance at 405 nm obtained with lysates from cells treated with 50 µM cisplatin is set as 100 cpu (cisplatin units), while an absorbance at 405 nm of 0.0 is set as 0.0 cpu. The degree of apoptosis is expressed as cpu in relation to the value of 100 cpu reached with the lysates obtained from cells treated with 50 µM cisplatin.

The compounds according to this invention tested in the assays above are expected to have an apoptosis inducing effect when tested in this assay.

The invention claimed is:

1. A method for treating a tumor of the cervix or kidney comprising administering to said patient a therapeutically effective and tolerable amount of a compound of formula I or a pharmaceutically acceptable salt thereof

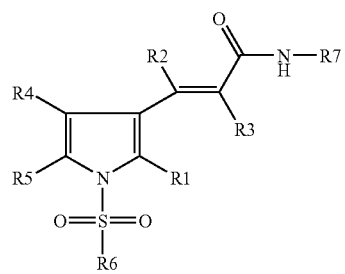

in which
R1 is hydrogen,
R2 is hydrogen,
R3 is hydrogen,
R4 is hydrogen,
R5 is hydrogen,
R6 is -T1-Q1, in which
T1 is a bond, or 1-2C-alkylene,
Q1 is Ar1, in which
Ar1 is phenyl, or R61 -substituted phenyl, in which
R61 is 1-4C-alkyl, or -T2-N(R611)R612, in which
either
T2 is a bond,
R611 is hydrogen, 1-4C-alkyl, phenyl-1-2C-alkyl, or Har1-1-2C-alkyl, in which
Har1 is pyridinyl, benzimidazolyl, benzoxazolyl, benzofuranyl, benzothiophenyl or indolyl, and
R612 is hydrogen, 1-4C-alkyl, or hydroxy-2-3C-alkyl,
or R611 and R612 together and with inclusion of the nitrogen atom, to which they are bonded, form a heterocyclic ring Het1, in which
Het1 is morpholino,
or
T2 is 1-2C-alkylene,
R611 is hydrogen, 1-4C-alkyl, phenyl-1-2C-alkyl, or Har1-1-2C-alkyl, in which
Har1 is pyridinyl, benzimidazolyl, benzoxazolyl, benzofuranyl, benzothiophenyl or indolyl, and
R612 is hydrogen, 1-4C-alkyl, or hydroxy-2-3C-alkyl,
or R611 and R612 together and with inclusion of the nitrogen atom, to which they are bonded, form a heterocyclic ring Het1, in which
Het1 is morpholino, and
R7 is hydroxyl, or 2-aminophenyl.

2. A method according to claim 1, wherein in the compound of formula I
R1 is hydrogen,
R2 is hydrogen,
R3 is hydrogen,
R4 is hydrogen,
R5 is hydrogen,
R6 is -T1-Q1, or benzyl, in which
T1 is a bond,
Q1 is Ar1, in which
Ar1 is phenyl, or R61-substituted phenyl, in which
R61 is 1-4C-alkyl, or -T2-N(R611)R612, in which
either
T2 is a bond,
R611 is 1-4C-alkyl, and
R612 is 1-4C-alkyl,
or
T2 is 1-2C-alkylene,
R611 is hydrogen, 1-4C-alkyl, phenyl-1-2C-alkyl, or Har1-1-2C-alkyl, in which
Har1 is pyridinyl, or indolyl, and
R612 is hydrogen, 1-4C-alkyl, or hydroxy-2-3C-alkyl,
or R611 and R612 together and with inclusion of the nitrogen atom, to which they are bonded, form a heterocyclic ring Het1, in which
Het1 is morpholino,
R7 is hydroxyl, or 2-aminophenyl,
or a pharmaceutically acceptable salt thereof.

3. A method according to claim 1, wherein in the compound of formula I
R1 is hydrogen,
R2 is hydrogen,
R3 is hydrogen,
R4 is hydrogen,
R5 is hydrogen,
R6 is -T1-Q1, or benzyl, in which
T1 is a bond,
Q1 is Ar1, in which
Ar1 is phenyl, 3-(R61)-phenyl, or 4-(R61)-phenyl, in which
R61 is methyl, or -T2-N(R611)R612, in which
either
T2 is a bond,
R611 is methyl, and
R612 is methyl,
or
T2 is methylene,
R611 is hydrogen, methyl, isobutyl, benzyl, Har1-methyl, or 2-(Har1)-ethyl in which
Har1 is pyridinyl or indolyl, and
R612 is hydrogen, methyl, or 2-hydroxy-ethyl,
or R611 and R612 together and with inclusion of the nitrogen atom, to which they are bonded, form a heterocyclic ring Het1, in which
Het1 is morpholino,
R7 is hydroxyl, or 2-aminophenyl,
or a pharmaceutically acceptable salt thereof.

4. A method according to claim 1, wherein in the compound of formula I
R1 is hydrogen,
R2 is hydrogen,
R3 is hydrogen,
R4 is hydrogen,
R5 is hydrogen,
R6 is -T1-Q1, or benzyl, in which
T1 is a bond,
Q1 is Ar1, in which
Ar1 is phenyl, 3-(R61)-phenyl, or 4-(R61)-phenyl, in which
R61 is methyl, or -T2-N(R611)R612, in which
either
T2 is a bond,
R611 is methyl, and
R612 is methyl,
or
T2 is methylene,
R611 is hydrogen, methyl, isobutyl, benzyl, Har1-methyl, or 2-(Har1)-ethyl in which
Har1 is pyridin-3-yl, pyridin-4-yl, indol-2-yl, indol-3-yl or indol-5-yl, and
R612 is hydrogen, methyl, or 2-hydroxy-ethyl,
or R611 and R612 together and with inclusion of the nitrogen atom, to which they are bonded, form a heterocyclic ring Het1, in which
Het1 is morpholino,
R7 is hydroxyl, or 2-aminophenyl,
or a pharmaceutically acceptable salt thereof.

5. A method according to claim 1, wherein in the compound of formula I
R1 is hydrogen,
R2 is hydrogen,
R3 is hydrogen,
R4 is hydrogen,
R5 is hydrogen,
R6 is -T1-Q1, or benzyl, in which
T1 is a bond,
1 is Ar1, in which
Ar1 is phenyl, 3-(R61)-phenyl, or 4-(R61)-phenyl, in which
R61 is methyl, or -T2-N(R611)R612, in which
either
T2 is a bond,
R611 is methyl, and
R612 is methyl,
or
T2 is methylene,
R611 is hydrogen, isobutyl, benzyl, Har1-methyl, or 2-(Har1)-ethyl, in which
Har1 is pyridin-3-yl, pyridin-4-yl, indol-2-yl, indol-3-yl or indol-5-yl, and
R612 is hydrogen,
or
T2 is methylene,
R611 is methyl, or 2-(Har1)-ethyl, in which
Har1 is indol-2-yl, and
R612 is methyl,
or
T2 is methylene,
R611 is 2-(Har1)-ethyl, in which
Har1 is indol-2-yl, and
R612 is 2-hydroxy-ethyl,
or
T2 is methylene, and
R611 and R612 together and with inclusion of the nitrogen atom, to which they are bonded, form a heterocyclic ring Het1, in which
Het1 is morpholino,
R7 is hydroxyl,
or a pharmaceutically acceptable salt thereof.

6. A method according to claim 1, wherein in the compound of formula I
R1 is hydrogen,
R2 is hydrogen,
R3 is hydrogen, R4 is hydrogen,
R5 is hydrogen,
R6 is -T1-Q1, or benzyl, in which
T1 is a bond,
Q1 is Ar1, in which
Ar1 is phenyl, 3-(R61)-phenyl, or 4-(R61)-phenyl, in which
R61 is methyl, or -T2-N(R611)R612, in which
either
T2 is a bond,
R611 is methyl, and
R612 is methyl,
or
T2 is methylene,
R611 is hydrogen, isobutyl, benzyl, Har1-methyl, or 2-(Har1)-ethyl, in which
Har1 is pyridin-3-yl, pyridin-4-yl, indol-3-yl, or indol-5-yl, and
R612 is hydrogen,
or
T2 is methylene,
R611 is methyl, or 2-(Har1)-ethyl, in which
Har1 is indol-2-yl, and
R612 is methyl,
or
T2 is methylene,
R611 is 2-(Har1)-ethyl, in which
Har1 is indol-2-yl, and
R612 is 2-hydroxy-ethyl,
or
T2 is methylene, and
R611 and R612 together and with inclusion of the nitrogen atom, to which they are bonded, form a heterocyclic ring Het1, in which
Het1 is morpholino,
R7 is 2-aminophenyl,
or a pharmaceutically acceptable salt thereof.

7. A method according to claim 1, wherein in the compound of formula I
R1 is hydrogen,
R2 is hydrogen,
R3 is hydrogen,
R4 is hydrogen,
R5 is hydrogen,
R6 is -T1-Q1, in which
T1 is a bond, or 1-2C-alkylene,
Q1 is Ar1, in which
Ar1 is phenyl, or R61-substituted phenyl, in which
R61 is 1-4C-alkyl, or -T2-N(R611)R612, in which
T2 is a bond, or 1-2C-alkylene,
R611 is 1-4C-alkyl, or Har1-1-2C-alkyl, in which
Har1 is benzimidazolyl, or indolyl,
R612 is 1-4C-alkyl,
R7 is hydroxyl, or 2-aminophenyl,
or a pharmaceutically acceptable salt thereof.

8. A method according to claim 1, wherein in the compound of formula I
R1 is hydrogen,
R2 is hydrogen,
R3 is hydrogen,
R4 is hydrogen,
R5 is hydrogen,
R6 is -T1-Q1, or benzyl, in which
T1 is a bond,
Q1 is Ar1, in which
Ar1 is R61-substituted phenyl, in which
R61 is methyl, dimethylamino, or -T2-N(R611)R612, in which
T2 is methylene,
R611 is methyl, or 2-(indol-2-yl)ethyl,
R612 is methyl,
R7 is hydroxyl, or 2-aminophenyl
or a pharmaceutically acceptable salt thereof.

9. A method according to claim 1, wherein the compound of formula I is selected from the group consisting of
(E)-N-Hydroxy-3-[1-(toluene-4-sulfonyl)-1-H-pyrrol-3-yl]-acrylamide,
N-Hydroxy-3-(1-phenylmethanesulfonyl-1H-pyrrol-3-yl)-acrylamide,
(E)-3-[1-(4-Dimethylamino-benzenesulfonyl)-1H-pyrrol-3-yl]-N-hydroxy-acrylamide,
(E)-N-(2-Amino-phenyl)-3-[1-(toluene-4-sulfonyl)-1H-pyrrol-3-yl]-acrylamide,
(E)-N-(2-Amino-phenyl)-3-(1-phenylmethanesulfonyl-1H-pyrrol-3-yl)-acrylamide,
(E)-N-(2-Amino-phenyl)-3-[1-(4-dimethylamino-benzenesulfonyl)-1H-pyrrol-3-yl]-acrylamide,
(E)-N-Hydroxy-3-(1-[4-(([2-(1H-indol-2-yl)-ethyl]-methyl-amino)-methyl)-benzene sulfonyl]-1H-pyrrol-3-yl)-acrylamide,
(E)-3-[1-(4-Dimethylaminomethyl-benzenesulfonyl)-1H-pyrrol-3-yl]-N-hydroxy-acrylamide,
(E)-N-Hydroxy-3-[1-(4-{[(pyridin-3-ylmethyl)-amino]-methyl}-benzenesulfonyl)-1H-pyrrol-3-yl]-acrylamide,
(E)-N-Hydroxy-3-[1-(4-{[(1H-indol-3-ylmethyl)-amino]-methyl}-benzenesulfonyl)-1H-pyrrol-3-yl]-acrylamide,
(E)-3-{1-[4-(Benzylamino-methyl)-benzenesulfonyl]-1H-pyrrol-3-yl}-N-hydroxy-acrylamide,
(E)-N-Hydroxy-3-{1-[4-(isobutylamino-methyl)-benzenesulfonyl]-1H-pyrrol-3-yl}-acrylamide,
(E)-N-Hydroxy-3-[1-(4-{[(1H-indol-5-ylmethyl)-amino]-methyl}-benzenesulfonyl)-1H-pyrrol-3-yl]-acrylamide,
(E)-N-Hydroxy-3-[1-(4-{[(pyridin-4-ylmethyl)-amino]-methyl}-benzenesulfonyl)-1H-pyrrol-3-yl]-acrylamide,
(E)-3-[1-(4-Aminomethyl-benzenesulfonyl)-1H-pyrrol-3-yl]-N-hydroxy-acrylamide,
(E)-N-Hydroxy-3-[1-(4-morpholin-4-ylmethyl-benzenesulfonyl)-1H-pyrrol-3-yl]-acrylamide,
(E)-N-Hydroxy-3-{1-[4-({(2-hydroxy-ethyl)-[2-(1H-indol-2-yl)-ethyl]-amino}-methyl)-benzenesulfonyl]-1H-pyrrol-3-yl}-acrylamide,
and a pharmaceutically acceptable salt thereof.

10. A method according to claim 1, wherein the compound of formula I is selected from the group consisting of
(E)-N-Hydroxy-3-[1-(toluene-4-sulfonyl)-1-H-pyrrol-3-yl]-acrylamide
N-Hydroxy-3-(1-phenylmethanesulfonyl-1H-pyrrol-3-yl)-acrylamide
(E)-3-[1-(4-Dimethylamino-benzenesulfonyl)-1H-pyrrol-3-yl]-N-hydroxy-acrylamide
(E)-N-(2-Amino-phenyl)-3-[1-(4-dimethylamino-benzenesulfonyl)-1H-pyrrol-3-yl]-acrylamide
and a pharmaceutically acceptable salt thereof.

11. A method according to claim 1, wherein the compound of formula I is selected from the group consisting of
(E)-N-Hydroxy-3-(1-[4-(([2-(1H-indol-2-yl)-ethyl]-methyl-amino)methyl)-benzene sulfonyl]-1H-pyrrol-3-yl)-acrylamide (E)-3-[1-(4-Dimethylaminomethyl-benzenesulfonyl)-1H-pyrrol-3-yl]-N-hydroxy-acrylamide
(E)-N-Hydroxy-3-[1-(4-{[(pyridin-3-ylmethyl)-amino]-methyl}-benzenesulfonyl)-1H-pyrrol-3-yl]-acrylamide
(E)-N-Hydroxy-3-[1-(4-{[(1H-indol-3-ylmethyl)-amino]-methyl}-benzenesulfonyl)-1H-pyrrol-3-yl]-acrylamide
(E)-N-Hydroxy-3-[1-(4-{[(pyridin-4-ylmethyl)-amino]-methyl}-benzenesulfonyl)-1H-pyrrol-3-yl]-acrylamide
(E)-3-{1-[4-(Benzylamino-methyl)-benzenesulfonyl]-1H-pyrrol-3-yl}-N-hydroxy-acrylamide
(E)-N-Hydroxy-3-{1-[4-(isobutylamino-methyl)-benzenesulfonyl]-1H-pyrrol-3-yl}-acrylamide
(E)-N-Hydroxy-3-[1-(4-{[(1H-indol-5-ylmethyl)-amino]-methyl}-benzenesulfonyl)-1H-pyrrol-3-yl]-acrylamide
(E)-N-Hydroxy-3-[1-(4-{[(pyridin-4-ylmethyl)-amino]-methyl}-benzenesulfonyl)-1H-pyrrol-3-yl]-acrylamide
E)-3-[1-(4-Aminomethyl-benzenesulfonyl)-1H-pyrrol-3-yl]-N-hydroxy-acrylamide
(E)-N-Hydroxy-3-[1-(4-morpholin-4-ylmethyl-benzenesulfonyl)-1H-pyrrol-3-yl]-acrylamide
(E)-N-Hydroxy-3-{1-[4-({(2-hydroxy-ethyl)-[2-(1H-indol-2-yl)-ethyl]-amino}-methyl)-benzenesulfonyl]-1H-pyrrol-3-yl}-acrylamide
and a pharmaceutically acceptable salt thereof.

12. The method according to claim 1, wherein the compound of formula I is administered simultaneously, sequentially or separately with one or more further therapeutic agents.

13. The method according to claim 1, wherein the disease treated is atumor of the kidney.

14. The method according to claim 1, wherein the disease treated is a tumor of the cervix.

15. A method according to claim 14, wherein the compound of formula I is selected from the group consisting of
(E)-N-Hydroxy-3-[1-(toluene-4-sulfonyl)-1-H-pyrrol-3-yl]-acrylamide,
N-Hydroxy-3-(1-phenylmethanesulfonyl-1H-pyrrol-3-yl)-acrylamide,
(E)-3-[1-(4-Dimethylamino-benzenesulfonyl)-1H-pyrrol-3-yl]-N-hydroxy-acrylamide,
(E)-N-(2-Amino-phenyl)-3-[1-(toluene-4-sulfonyl)-1H-pyrrol-3-yl]-acrylamide,
(E)-N-(2-Amino-phenyl)-3-(1-phenylmethanesulfonyl-1H-pyrrol-3-yl)-acrylamide,
(E)-N-(2-Amino-phenyl)-3-[1-(4-dimethylamino-benzenesulfonyl)-1H-pyrrol-3-yl]-acrylamide,
(E)-N-Hydroxy-3-(1-[4-(([2-(1H-indol1-2-yl)-ethyl]-methyl-amino)-methyl)-benzene sulfonyl]-1H-pyrrol-3-yl)-acrylamide,
(E)-3-[1-(4-Dimethylaminomethyl-benzenesulfonyl)-1H-pyrrol-3-yl]-N-hydroxy-acrylamide,
(E)-N-Hydroxy-3-[1-(4-{[(pyridin-3-ylmethyl)-amino]-methyl}-benzenesulfonyl)-1H-pyrrol-3-yl]-acrylamide,
(E)-N-Hydroxy-3-[1-(4-{[(1H-indol-3-ylmethyl)-amino]-methyl}-benzenesulfonyl)-1H-pyrrol-3-yl]-acrylamide,
(E)-3-{1-[4-(Benzylamino-methyl)-benzenesulfonyl]-1H-pyrrol-3-yl}-hydroxy-acrylamide,
(E)-N-Hydroxy-3-{1-[4-(isobutylamino-methyl)-benzenesulfonyl]-1H-pyrrol-3-yl}-acrylamide,
(E)-N-Hydroxy-3-[1-(4-{[(1H-indol-5-ylmethyl)-amino]-methyl}-benzenesulfonyl)-1H-pyrrol-3-yl]-acrylamide,
(E)-N-Hydroxy-3-[1-(4-{[(pyridin-4-ylmethyl)-amino]-methyl}-benzenesulfonyl)-1H-pyrrol-3-yl]-acrylamide,
(E)-3-[1-(4-Aminomethyl-benzenesulfonyl)-1H-pyrrol-3-yl]-N-hydroxy-acrylamide,
(E)-N-Hydroxy-3-[1-(4-morpholin-4-ylmethyl-benzenesulfonyl)-1H-pyrrol-3-yl]-acrylamide,
(E)-N-Hydroxy-3-{1-[4-({(2-hydroxy-ethyl)-[2-(1H-indol-2-yl)-ethyl]-amino}-methyl)-benzenesulfonyl]-1H-pyrrol-3-yl}-acrylamide,
and a pharmaceutically acceptable salt thereof.

16. The method according to claim 15, wherein the disease treated is a tumor of the cervix.

17. The method according to claim 15, wherein the disease treated is a tumor of the kidney.

18. The method according to claim 10, wherein the disease treated is a tumor of the kidney.

19. The method according to claim 10, wherein the disease treated is a tumor of the cervix.

20. The method according to claim 11, wherein the disease treated is a tumor of the cervix.

21. The method according to claim 11, wherein the disease treated is a tumor of the kidney.

22. The method according to claim 9, wherein the disease treated is a tumor of the cervix.

23. The method according to claim 9, wherein the disease treated is a tumor of the kidney.

24. A method for inhibiting HDAC, comprising administering to a patient in need thereof a therapeutically effective and tolerable amount of a compound of formula I or a pharmaceutically acceptable salt thereof

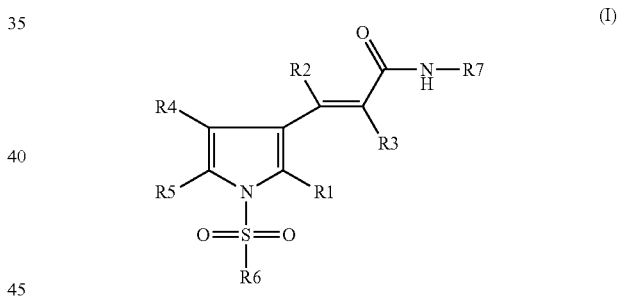

(I)

in which
R1 is hydrogen,
R2 is hydrogen,
R3 is hydrogen,
R4 is hydrogen,
R5 is hydrogen,
R6 is -T1-Q1, in which
T1 is a bond, or 1-2C-alkylene,
Q1 is Ar1, in which
Ar1 is phenyl, or R61 -substituted phenyl, in which
R61 is 1-4C-alkyl, or -T2-N(R611)R612, in which
either
T2 is a bond,
R611 is hydrogen, 1-4C-alkyl, phenyl-1-2C-alkyl, or Har1-1-2C-alkyl, in which
Har1 is pyridinyl, benzimidazolyl, benzoxazolyl, benzofuranyl, benzothiophenyl or indolyl, and
R612 is hydrogen, 1-4C-alkyl, or hydroxy-2-3C-alkyl,
or R611 and R612 together and with inclusion of the nitrogen atom, to which they are bonded, form a heterocyclic ring Het1, in which Het1 is morpholino,
or
T2 is 1-2C-alkylene,
R611 is hydrogen, 1-4C-alkyl, phenyl-1-2C-alkyl, or Har1-1-2C-alkyl, in which
Har1 is pyridinyl, benzimidazolyl, benzoxazolyl, benzofuranyl, benzothiophenyl or indolyl, and
R612 is hydrogen, 1-4C-alkyl, or hydroxy-2-3C-alkyl,
or R611 and R612 together and with inclusion of the nitrogen atom, to which they are bonded, form a heterocyclic ring Het1, in which
Het1 is morpholino, and
R7 is hydroxyl, or 2-aminophenyl.

* * * * *

UNITED STATES PATENT AND TRADEMARK OFFICE
CERTIFICATE OF CORRECTION

PATENT NO.       : 8,399,505 B2
APPLICATION NO.  : 12/822606
DATED            : March 19, 2013
INVENTOR(S)      : Maier et al.

It is certified that error appears in the above-identified patent and that said Letters Patent is hereby corrected as shown below:

In the Claims:

Column 66, line 30 reads "1 is Arl, in which" should read -- Q1 is Arl, in which --

Column 69, line 33 reads "treated is atumor of the kidney." should read -- treated is a tumor of the kidney. --

Column 69, line 50 reads "(E)-N-Hydroxy-3-(1-[4-(([2-(1H-indoll-2-yl)-ethyl]-me-" should read -- "(E)-N-Hydroxy-3-(1-[4-(([2-(1H-indol-2-yl)-ethyl]-me- --

Column 69, line 62 reads "1H-pyrrol-3-yl}-hydroxy-acrylamide," should read -- 1H-pyrrol-3-yl}N-hydroxy-acrylamide, --

Signed and Sealed this
Twenty-first Day of May, 2013

Teresa Stanek Rea
*Acting Director of the United States Patent and Trademark Office*